(12) United States Patent
Collins et al.

(10) Patent No.: US 8,618,121 B2
(45) Date of Patent: Dec. 31, 2013

(54) 9H-PYRIMIDO[4,5-B]INDOLES, 9H-PYRIDO[4',3':4,5]PYRROLO[2,3-D]PYRIDINES, AND 9H 1,3,6,9 TETRAAZA-FLUORENES AS CHK1 KINASE FUNCTION INHIBITORS

(75) Inventors: Ian Collins, Sutton (GB); John Charles Reader, Cambridge (GB); Suki Klair, Cambridge (GB); Jane Scanlon, Cambridge (GB); Glynn Addison, Cambridge (GB); Michael Cherry, Cambridge (GB)

(73) Assignee: Cancer Research Technology Limited, London (GB)

( * ) Notice: Subject to any disclaimer, the term of this patent is extended or adjusted under 35 U.S.C. 154(b) by 614 days.

(21) Appl. No.: 12/665,961

(22) PCT Filed: Jul. 1, 2008

(86) PCT No.: PCT/GB2008/002259
§ 371 (c)(1),
(2), (4) Date: Apr. 26, 2010

(87) PCT Pub. No.: WO2009/004329
PCT Pub. Date: Jan. 8, 2009

(65) Prior Publication Data
US 2010/0210639 A1   Aug. 19, 2010

Related U.S. Application Data

(60) Provisional application No. 60/947,540, filed on Jul. 2, 2007.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl.
USPC .......................................... 514/267; 544/251

(58) Field of Classification Search
USPC .......................................... 514/267; 544/251
See application file for complete search history.

(56) References Cited

U.S. PATENT DOCUMENTS 3,773,778 A   11/1973  Hoehn et al.

FOREIGN PATENT DOCUMENTS

| WO | WO 95/19970  A1 | 7/1995 | |
| WO | WO 97/02266  A1 | 1/1997 | |
| WO | WO 03/037898 * | 5/2003 | ........... C07D 487/04 |
| WO | WO 03/037898  A1 | 5/2003 | |
| WO | WO 2005/037825 A2 | 4/2005 | |
| WO | WO 2006/116733 | 11/2006 | |
| WO | WO 2007/041712 | 4/2007 | |
| WO | WO 2007/044779 A1 | 4/2007 | |

OTHER PUBLICATIONS

West, Anthony R., Solid State Chemistry and Its Applications, Wiley, New York, 1988, 358.*
Tse, et al CHIR-124, A Novel Potent Inhibitor of Chk1, Potentiates the Cytotoxicity of Topoisomerase I Poisons In vitro and In vivo, Clin. Cancer Res. 13(2) (2007).*
Balaint and Vousden, 2001, "Activation and activities of the p53 tumour suppressor protein," *Br. J. Cancer*, vol. 85, pp. 1813-1823.
Bartek and Lukas, 2003, "Chk1 and Chk2 kinases in checkpoint control and cancer," *Cancer Cell*, vol. 3, pp. 421-429.
Carson and Lois, 1995, "Cancer progression and p53," *Lancet*, vol. 346, pp. 1009-1011.
Dixon and Norbury, 2002, "Therapeutic exploitation of checkpoint defects in cancer cells lacking p53 function," *Cell Cycle*, vol. 1, pp. 362-368.
Greenblatt et al., 1994, "Mutations in the p53 tumor suppressor gene: clues to cancer etiology and molecular pathogenesis," *Cancer Res.*, vol. 54, pp. 4855-4878.
Liu et al., 2000, "Chk1 is an essential kinase that is regulated by Atr and required for the G(2)/M DNA damage checkpoint," *Genes Dev.*, vol. 14, pp. 1448-1459.
Sanchez et al., 1997, "Conservation of the Chk1 checkpoint pathway in mammals: linkage of DNA damage to Cdk regulation through Cdc25," *Science*, vol. 277, pp. 1497-1501.
Sorensen et al., 2005, "Cell-cycle checkpoint kinase Chk1 is required for mammalian homologous recombination repair," *Nat. Cell Biol.*, vol. 7, pp. 195-201.
Tao and Lin, 2006, "Chk1 inhibitors for novel cancer treatment," *Anti-Cancer Agents in Medicinal Chemistry*, vol. 6, pp. 377-388.
Ugarkar et al., 2000, "Adenosine Kinase Inhibitors. 1. Synthesis, Enzyme Inhibition and Antiseizure Activity of 5-Iodotubercidin Analogues," *Journal of Medicinal Chemistry*, vol. 43, pp. 3883-2893.

(Continued)

*Primary Examiner* — Erich A Leeser
(74) *Attorney, Agent, or Firm* — Swanson & Bratschun, L.L.C.

(57) ABSTRACT

The present invention pertains generally to the field of therapeutic compounds, and more specifically to certain tricyclic compounds (referred to herein as TC compounds), and especially certain 9H-pyrimido[4,5-b]indole, 9H-pyrido[4',3':4, 5]pyrrolo[2,3-d]pyridine, and 9H-1,3,6,9-tetraaza-fluorene compounds, which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

18 Claims, No Drawings

(56) References Cited

OTHER PUBLICATIONS

Wang et al., 1996, "UCN-01: a potent abrogator of G2 checkpoint function in cancer cells with disrupted p53," *J. Natl. Cancer Inst.*, vol. 8, pp. 956-965.

Weinert and Hartwell, 1989, "Control of G2 delay by the rad9 gene of *Saccharomyces cerevisiae*," *J. Cell Sci. Suppl.*, vol. 12, pp. 145-148.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer Ther.*, vol. 5, pp. 1935-1943.

Zachos et al., 2003, "Chk1-deficient tumour cells are viable but exhibit multiple checkpoint and survival defects," *EMBO J.*, vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, vol. 99, pp. 14795-14800.

International Search Report (ISR) and Written Opinion of International Searching Authority (WOISA) for PCT/GB2008/002259.

International Preliminary Report on Patentability (IPRP) for PCT/GB2008/002259.

\* cited by examiner

9H-PYRIMIDO[4,5-B]INDOLES, 9H-PYRIDO[4',3':4,5]PYRROLO[2,3-D]PYRIDINES, AND 9H 1,3,6,9 TETRAAZA-FLUORENES AS CHK1 KINASE FUNCTION INHIBITORS

RELATED APPLICATION

This application is related to U.S. provisional patent application No. 60/947,540 filed 2 Jul. 2007, the contents of which are incorporated herein by reference in their entirety.

TECHNICAL FIELD

The present invention pertains generally to the field of therapeutic compounds, and more specifically to certain tricyclic compounds (referred to herein as TC compounds), and especially certain 9H-pyrimido[4,5-b]indole, 9H-pyrido[4',3':4,5]pyrrolo[2,3-d]pyridine, and 9H-1,3,6,9-tetraaza-fluorene compounds, which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Checkpoint Kinase 1 (CHK1)

Progression through the cell division cycle is a tightly regulated process and is monitored at several positions known as cell cycle checkpoints (see, e.g., Weinert and Hartwell, 1989; Bartek and Lukas, 2003). These checkpoints are found in all four stages of the cell cycle; G1, S (DNA replication), G2 and M (Mitosis) and they ensure that key events which control the fidelity of DNA replication and cell division are completed correctly. Cell cycle checkpoints are activated by a number of stimuli, including DNA damage and DNA errors caused by defective replication. When this occurs, the cell cycle will arrest, allowing time for either DNA repair to occur or, if the damage is too severe, for activation of cellular processes leading to controlled cell death.

All cancers, by definition, have some form of aberrant cell division cycle. Frequently, the cancer cells possess one or more defective cell cycle checkpoints, or harbour defects in a particular DNA repair pathway. These cells are therefore often more dependent on the remaining cell cycle checkpoints and repair pathways, compared to non-cancerous cells (where all checkpoints and DNA repair pathways are intact). The response of cancer cells to DNA damage is frequently a critical determinant of whether they continue to proliferate or activate cell death processes and die. For example, tumour cells that contain a mutant form(s) of the tumour suppressor p53 are defective in the G1 DNA damage checkpoint. Thus inhibitors of the G2 or S-phase checkpoints are expected to further impair the ability of the tumour cell to repair damaged DNA.

Many known cancer treatments cause DNA damage by either physically modifying the cell's DNA or disrupting vital cellular processes that can affect the fidelity of DNA replication and cell division, such as DNA metabolism, DNA synthesis, DNA transcription and microtubule spindle formation. Such treatments include for example, radiotherapy, which causes DNA strand breaks, and a variety of chemotherapeutic agents including topoisomerase inhibitors, antimetabolites, DNA-alkylating agents, and platinum-containing cytotoxic drugs. A significant limitation to these genotoxic treatments is drug resistance. One of the most important mechanisms leading to this resistance is attributed to activation of cell cycle checkpoints, giving the tumour cell time to repair damaged DNA. By abrogating a particular cell cycle checkpoint, or inhibiting a particular form of DNA repair, it may therefore be possible to circumvent tumour cell resistance to the genotoxic agents and augment tumour cell death induced by DNA damage, thus increasing the therapeutic index of these cancer treatments.

CHK1 is a serine/threonine kinase involved in regulating cell cycle checkpoint signals that are activated in response to DNA damage and errors in DNA caused by defective replication (see, e.g., Bartek and Lukas, 2003). CHK1 transduces these signals through phosphorylation of substrates involved in a number of cellular activities including cell cycle arrest and DNA repair. Two key substrates of CHK1 are the Cdc25A and Cdc25C phosphatases that dephosphorylate CDK1 leading to its activation, which is a requirement for exit from G2 into mitosis (M phase) (see, e.g., Sanchez et al., 1997). Phosphorylation of Cdc25C and the related Cdc25A by CHK1 blocks their ability to activate CDK1, thus preventing the cell from exiting G2 into M phase. The role of CHK1 in the DNA damage-induced G2 cell cycle checkpoint has been demonstrated in a number of studies where CHK1 function has been knocked out (see, e.g., Liu et al., 2000; Zhao et al., 2002; Zachos et al., 2003).

The reliance of the DNA damage-induced G2 checkpoint upon CHK1 provides one example of a therapeutic strategy for cancer treatment, involving targeted inhibition of CHK1. Upon DNA damage, the p53 tumour suppressor protein is stabilised and activated to give a p53-dependent G1 arrest, leading to apoptosis or DNA repair (Balaint and Vousden, 2001). Over half of all cancers are functionally defective for p53, which can make them resistant to genotoxic cancer treatments such as ionising radiation (IR) and certain forms of chemotherapy (see, e.g., Greenblatt et al., 1994; Carson and Lois, 1995). These p53 deficient cells fail to arrest at the G1 checkpoint or undergo apoptosis or DNA repair, and consequently may be more reliant on the G2 checkpoint for viability and replication fidelity. Therefore abrogation of the G2 checkpoint through inhibition of the CHK1 kinase function may selectively sensitise p53 deficient cancer cells to genotoxic cancer therapies, and this has been demonstrated (see, e.g., Wang et al., 1996; Dixon and Norbury, 2002).

In addition, CHK1 has also been shown to be involved in S phase cell cycle checkpoints and DNA repair by homologous recombination. Thus, inhibition of CHK1 kinase in those cancers that are reliant on these processes after DNA damage, may provide additional therapeutic strategies for the treatment of cancers using CHK1 inhibitors (see, e.g., Sorensen et al., 2005). Recent data using CHK1 selective siRNA supports the selective inhibition of CHK1 as a relevant therapeutic approach, and suggests that combined inhibition with certain other checkpoint kinases provides no additional benefit and may be non-productive (see, e.g., Xiao et al., 2006). Small-molecule selective inhibitors of CHK1 kinase function from various chemical classes have been described (see, e.g., Tao and Lin, 2006).

SUMMARY OF THE INVENTION

One aspect of the invention pertains to certain tricyclic compounds (referred to herein as TC compounds), as described herein.

Another aspect of the invention pertains to a composition (e.g., a pharmaceutical composition) comprising a TC compound, as described herein, and a pharmaceutically acceptable carrier or diluent.

Another aspect of the invention pertains to method of preparing a composition (e.g., a pharmaceutical composition) comprising the step of admixing a TC compound, as described herein, and a pharmaceutically acceptable carrier or diluent.

Another aspect of the present invention pertains to a method of inhibiting CHK1 kinase function in a cell, in vitro or in vivo, comprising contacting the cell with an effective amount of a TC compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a TC compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of treatment comprising administering to a subject in need of treatment a therapeutically-effective amount of a TC compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a TC compound as described herein for use in a method of treatment of the human or animal body by therapy.

In one embodiment, the method of treatment comprises treatment with both (i) a TC compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of a TC compound, as described herein, in the manufacture of a medicament for use in treatment.

In one embodiment, the treatment comprises treatment with both (i) a medicament comprising a TC compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the treatment is treatment of a disease or condition that is mediated by CHK1.

In one embodiment, the treatment is treatment of a disease or condition that is ameliorated by the inhibition of CHK1 kinase function.

In one embodiment, the treatment is treatment of a proliferative condition.

In one embodiment, the treatment is treatment of cancer.

In one embodiment, the treatment is treatment of: p53 negative cancer.

In one embodiment, the treatment is treatment of: lung cancer, breast cancer, ovarian cancer, colorectal cancer, melanoma, or glioma.

Another aspect of the present invention pertains to a kit comprising (a) a TC compound, as described herein, preferably provided as a pharmaceutical composition and in a suitable container and/or with suitable packaging; and (b) instructions for use, for example, written instructions on how to administer the compound.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

Another aspect of the present invention pertains to a TC compound obtainable by a method of synthesis as described herein, or a method comprising a method of synthesis as described herein.

Another aspect of the present invention pertains to a TC compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain tricyclic compounds (for convenience, collectively referred to herein as "tricyclic compounds" or "TC compounds") which are 9H-pyrimido[4,5-b]indoles, 9H-pyrido[4',3':4,5]pyrrolo[2,3-d]pyridines, or 9H-1,3,6,9-tetraaza-fluorenes.

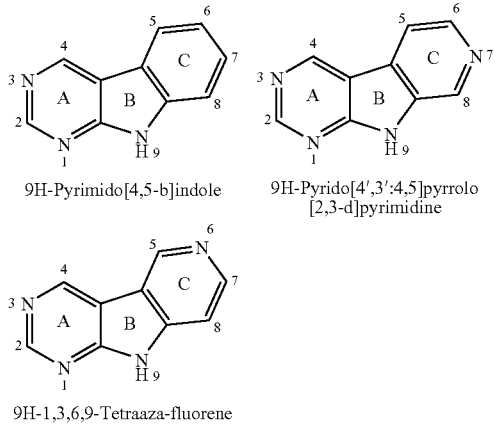

9H-Pyrimido[4,5-b]indole

9H-Pyrido[4',3':4,5]pyrrolo[2,3-d]pyrimidine 9H-1,3,6,9-Tetraaza-fluorene

Note that all of the compounds of the present invention have, inter alia, a nitrogen atom attached to the 4-position, for example, as part of an optionally substituted amino group, a piperidino group, a morpholino group, etc. Consequently, each of the groups $-Q^1$, $-Q^2$, $-Q^3$, $-Q^4$, and $-Q^5$ (discussed below) has a "leading nitrogen atom".

Class 1

In one embodiment, the compounds are selected from compounds of the following formula, and pharmaceutically acceptable salts and solvates thereof:

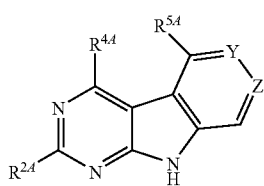

wherein:
either: Y is $CR^{6A}$ and Z is N;
or: Y is N and Z is $CR^{7A}$;
—$R^{4A}$ is independently $-Q^1$, $-Q^2$, $-Q^3$, or $-Q^4$;
—$R^{2A}$ is independently —H or $-G^1$;
—$R^{5A}$ is independently —H or $-G^2$;
—$R^{6A}$, if present, is independently —H or $-G^3$; and
—$R^{7A}$, if present, is independently —H or $-G^3$.

These compounds may conveniently be characterised by the nitrogen atom in Ring C and the presence of a nitrogen atom attached to the 4-position.

Class 2

In one embodiment, the compounds are selected from compounds of the following formula, and pharmaceutically acceptable salts and solvates thereof:

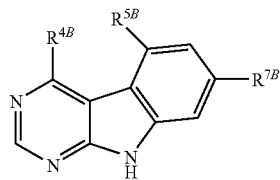

wherein:
—$R^{4B}$ is independently $-Q^1$, $-Q^2$, $-Q^3$, or $-Q^4$;
—$R^{5B}$ is independently —H or $-G^2$; and
—$R^{7B}$ is independently $-G^4$.

These compounds may conveniently be characterised by the 9H-pyrimido[4,5-b]indole scaffold, the presence of a substituent at the 7-position (i.e., a group other than —H), and the presence of a nitrogen atom attached to the 4-position.

Class 3

In one embodiment, the compounds are selected from compounds of the following formula, and pharmaceutically acceptable salts and solvates thereof:

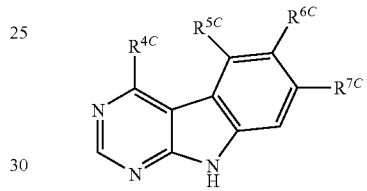

wherein:
—$R^{4C}$ is independently $-Q^5$;
—$R^{5C}$ is independently —H or $-G^2$;
—$R^{6C}$ is independently —H or $-G^3$; and
—$R^{7C}$ is independently —H or $-G^3$.

These compounds may conveniently be characterised by the 9H-pyrimido[4,5-b]indole scaffold and the presence of a substituted morpholino group at the 4-position.

The Groups Y and Z

In one embodiment, either: Y is $CR^{6A}$ and Z is N, or: Y is N and Z is $CR^{7A}$.
In one embodiment, Y is $CR^{6A}$ and Z is N.
In one embodiment, Y is N and Z is $CR^{7A}$.

The Group $R^{2A}$

In one embodiment, —$R^{2A}$ is independently —H or $-G^1$.
In one embodiment, —$R^{2A}$ is independently —H.
In one embodiment, —$R^{2A}$ is independently $-G^1$.

The Group $R^{4A}$

In one embodiment, —$R^{4A}$ is independently $-Q^1$, $-Q^2$, $-Q^3$, or $-Q^4$.
In one embodiment, —$R^{4A}$ is independently $-Q^1$.
In one embodiment, —$R^{4A}$ is independently $-Q^2$.
In one embodiment, —$R^{4A}$ is independently $-Q^3$.
In one embodiment, —$R^{4A}$ is independently $-Q^4$.

The Group $R^{5A}$

In one embodiment, —$R^{5A}$ is independently —H or $-G^2$.
In one embodiment, —$R^{5A}$ is independently —H.
In one embodiment, —$R^{5A}$ is independently $-G^2$.

The Group $R^{6A}$

In one embodiment, —$R^{6A}$, if present, is independently —H or $-G^3$.
In one embodiment, —$R^{6A}$, if present, is independently —H.
In one embodiment, —$R^{6A}$, if present, is independently $-G^3$.

The Group $R^{7A}$

In one embodiment, $-R^{7A}$, if present, is independently $-H$ or $-G^3$.

In one embodiment, $-R^{7A}$, if present, is independently $-H$.

In one embodiment, $-R^{7A}$, if present, is independently $-G^3$.

The Group $R^{4B}$

In one embodiment, $-R^{4B}$ is independently $-Q^1$, $-Q^2$, $-Q^3$, or $-Q^4$.

In one embodiment, $-R^{4B}$ is independently $-Q^1$.
In one embodiment, $-R^{4B}$ is independently $-Q^2$.
In one embodiment, $-R^{4B}$ is independently $-Q^3$.
In one embodiment, $-R^{4B}$ is independently $-Q^4$.

The Group $R^{5B}$

In one embodiment, $-R^{5B}$ is independently $-H$ or $-G^2$.
In one embodiment, $-R^{5B}$ is independently $-H$.
In one embodiment, $-R^{5B}$ is independently $-G^2$.

The Group $R^{7B}$

In one embodiment, $-R^{7B}$ is independently $-G^4$.

The Group $R^{4C}$

In one embodiment, $-R^{4C}$ is independently $-Q^5$.

The Group $R^{5C}$

In one embodiment, $-R^{5C}$ is independently $-H$ or $-G^2$.
In one embodiment, $-R^{5C}$ is independently $-H$.
In one embodiment, $-R^{5C}$ is independently $-G^2$.

The Group $R^{6C}$

In one embodiment, $-R^{6C}$ is independently $-H$ or $-G^3$.
In one embodiment, $-R^{6C}$ is independently $-H$.
In one embodiment, $-R^{6C}$ is independently $-G^3$.

The Group $R^{7C}$

In one embodiment, $-R^{7C}$ is independently $-H$ or $-G^3$.
In one embodiment, $-R^{7C}$ is independently $-H$.
In one embodiment, $-R^{7C}$ is independently $-G^3$.

The Group $Q^1$

In one embodiment, $-Q^1$ is independently $-NH_2$, $-NHR^{W1}$, or $-NR^{W1}_2$;
wherein:
each $-R^{W1}$ is independently:
$-R^{X1}$, $-R^{X2}$, $-R^{X3}$, $-R^{X4}$, $-R^{X5}$, $-R^{X6}$, $-R^{X7}$, $-R^{X8}$,
$-L^X-R^{X4}$, $-L^X-R^{X5}$, $-L^X-R^{X6}$, $-L^X-R^{X7}$, $-L^X-R^{X8}$;
wherein:
each $-R^{X1}$ is independently saturated aliphatic $C_{1-6}$alkyl;
each $-R^{X2}$ is independently aliphatic $C_{2-6}$alkenyl;
each $-R^{X3}$ is independently aliphatic $C_{2-6}$alkynyl;
each $-R^{X4}$ is independently saturated $C_{3-6}$cycloalkyl;
each $-R^{X5}$ is independently $C_{3-6}$cycloalkenyl;
each $-R^{X6}$ is independently non-aromatic $C_{3-7}$heterocyclyl;
each $-R^{X7}$ is independently $C_{6-10}$carboaryl;
each $-R^{X8}$ is independently $C_{5-10}$heteroaryl;
each $-L^X-$ is independently saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{5-10}$heteroaryl, and $C_{1-3}$alkylene is optionally substituted, for example, with one or more substituents $-R^{X9}$, wherein each $-R^{X9}$, if present, is independently:
$-F$, $-Cl$, $-Br$, $-I$,
$-R^{Y1}$,
$-CF_3$,
$-OH$,
$-OR^{Y1}$,
$-OCF_3$,
$-SH$,
$-SR^{Y1}$,
$-CN$,
$-NO_2$,
$-NH_2$, $-NHR^{Y1}$, $-NR^{Y1}_2$, $-NR^{Y2}R^{Y3}$,
$-C(=O)OH$,
$-C(=O)OR^{Y1}$,
$-C(=O)NH_2$, $-C(=O)NHR^{Y1}$, $-C(=O)NR^{Y1}_2$, $-C(=O)NR^{Y2}R^{Y3}$,
$-L^Y-OH$, $-L^Y-OR^{Y1}$,
$-L^Y-NH_2$, $-L^Y-NHR^{Y1}$, $-L^Y-NR^{Y1}_2$, or $-L^Y-NR^{Y2}R^{Y3}$;
wherein:
each $-R^{Y1}$ is independently saturated aliphatic $C_{1-4}$alkyl, phenyl, or benzyl;
each $-L^Y-$ is independently saturated aliphatic $C_{1-5}$alkylene; and
in each group $-NR^{Y2}R^{Y3}$, $R^{Y2}$ and $R^{Y3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, $-Q^1$ is independently $-NHR^{W1}$ or $-NR^{W1}_2$.

In one embodiment, each $-R^{W1}$, if present, is independently:
$-R^{X1}$, $-R^{X4}$, $-R^{X7}$, $-R^{X8}$,
$-L^X-R^{X4}$, $-L^X-R^{X7}$, or $-L^X-R^{X8}$.

In one embodiment, each $-R^{W1}$, if present, is independently:
$-R^{X1}$, $-R^{X4}$, $-R^{X8}$,
$-L^X-R^{X4}$, or $-L^X-R^{X8}$.

In one embodiment, each $-L^X-$, if present, is independently $-CH_2-$.

In one embodiment, each $-R^{X6}$, if present, is independently pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each $-R^{X6}$, if present, is independently pyrrolidinyl, piperidinyl, or morpholinyl, and is optionally substituted.

In one embodiment, each $-R^{X7}$, if present, is independently phenyl, and is optionally substituted.

In one embodiment, each $-R^{X8}$, if present, is independently $C_{5-6}$heteroaryl, and is optionally substituted.

In one embodiment, each $-R^{X8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each $-L^Y-$, if present, is independently saturated aliphatic $C_{1-3}$alkylene.

In one embodiment, each $-R^{Y1}$, if present, is independently $C_{1-4}$alkyl.

In one embodiment, each $-NR^{Y2}R^{Y3}$, if present, is independently pyrrolidino, imidazolidino, pyrazolidino, piperidino, piperizino, morpholino, azepino, or diazepino, and is optionally substituted, for example, with one or more groups selected from $C_{1-3}$alkyl and $-CF_3$.

In one embodiment, each $-NR^{Y2}R^{Y3}$, if present, is independently pyrrolidino, piperidino, piperizino, or morpholino, and is optionally substituted, for example, with one or more groups selected from $C_{1-3}$alkyl and $-CF_3$.

In one embodiment, each $-R^{X9}$, if present, is independently $-F$, $-Cl$, $-Br$, $-I$, -Me, -Et, $-CF_3$, $-OH$, $-OMe$, $-OEt$, $-OCF_3$, $-NH_2$, $-NHMe$, or $-NMe_2$.

The Group $Q^2$

In one embodiment, $-Q^2$ is independently $-NR^{W2}R^{W3}$, wherein $R^{W2}$ and $R^{W3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, $-NR^{W2}R^{W3}$, if present, is independently pyrrolidino, imidazolidino, pyrazolidino, piperidino, piperizino, morpholino, azepino, or diazepino, and is optionally substituted, for example, with one or more substituents $-R^{X10}$.

In one embodiment, $-NR^{W2}R^{W3}$, if present, is independently pyrrolidino, piperidino, piperizino, or morpholino, and is optionally substituted, for example, with one or more substituents $-R^{X10}$.

In one embodiment, $-NR^{W2}R^{W3}$, if present, is independently pyrrolidino or piperidino, and is optionally substituted, for example, with one or more substituents $-R^{X10}$.

In one embodiment, each $-R^{X10}$, if present, is independently:
- $-F$, $-Cl$, $-Br$, $-I$,
- $-R^{Z1}$,
- $-CF_3$,
- $-OH$,
- $-OR^{Z1}$,
- $-OCF_3$,
- $-SH$,
- $-SR^{Z1}$,
- $-CN$,
- $-NO_2$,
- $-NH_2$, $-NHR^{Z1}$, $-NR^{Z1}{}_2$, $-NR^{Z2}R^{Z3}$,
- $-C(=O)OH$,
- $-C(=O)OR^{Z1}$,
- $-C(=O)NH_2$, $-C(=O)NHR^{Z1}$, $-C(=O)NR^{Z1}{}_2$, $-C(=O)NR^{Z2}R^{Z3}$,
- $-NHC(=O)R^{Z1}$, $-NR^{Z1}C(=O)R^{Z1}$,
- $-OC(=O)R^{Z1}$,
- $-L^Z$-$OH$,
- $-L^Z$-$NH_2$, $-L^Z$-$NHR^{Z1}$, $-L^Z$-$NR^{Z1}{}_2$, or $-L^Z$-$NR^{Z2}R^{Z3}$;

wherein:
each $-R^{Z1}$ is independently saturated aliphatic $C_{1-4}$alkyl, phenyl, or benzyl;
each $-L^Z$- is independently saturated aliphatic $C_{1-5}$alkylene; and
in each group $-NR^{Z2}R^{Z3}$, $R^{Z2}$ and $R^{Z3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each $-NR^{Z2}R^{Z3}$, if present, is independently pyrrolidino, imidazolidino, pyrazolidino, piperidino, piperizino, morpholino, azepino, or diazepino; and is optionally substituted, for example, with one or more groups selected from $C_{1-3}$alkyl and $-CF_3$.

In one embodiment, each $-R^{X10}$, if present, is independently:
- $-R^{Z1}$
- $-CF_3$,
- $-NH_2$, $-NHR^{Z1}$, $-NR^{Z1}{}_2$,
- $-C(=O)NH_2$, $-C(=O)NHR^{Z1}$, $-C(=O)NR^{Z1}{}_2$,
- $-NHC(=O)R^{Z1}$, $-NR^{Z1}C(=O)R^{Z1}$,
- $-L^Z$-$NH_2$, $-L^Z$-$NHR^{Z1}$, or $-L^Z$-$NR^{Z1}{}_2$.

In one embodiment, each $-L^Z$-, if present, is independently saturated aliphatic $C_{1-3}$alkylene.

In one embodiment, each $-R^{Z1}$, if present, is independently saturated aliphatic $C_{1-4}$alkyl.

The Group $Q^3$

In one embodiment, $-Q^3$ is independently:

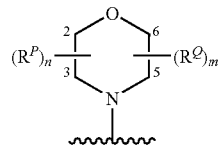

wherein:
m is independently 0 or 1;
n is independently 0, 1 or 2;
each $-R^P$, if present, is independently saturated aliphatic $C_{1-3}$alkyl or $-CF_3$;
$-R^Q$, if present, is independently:
- $-L^R$-$NH_2$, $-L^R$-$NHR^R$, $-L^R$-$NR^R{}_2$,
- $-L^R$-$OH$, $-L^R$-$OR^R$,
- $-C(=O)OH$, $-C(=O)OR^R$,
- $-C(=O)NH_2$, $-C(=O)NHR^R$, $-C(=O)NR^R{}_2$,
- $-L^R$-$C(=O)OH$, $-L^R$-$C(=O)OR^R$,
- $-L^R$-$C(=O)NH_2$, $-L^R$-$C(=O)NHR^R$, $-L^R$-$C(=O)NR^R{}_2$, or
- $-L^R$-$CN$;

wherein:
each $-L^R$- is independently saturated aliphatic $C_{1-3}$alkylene; and
each $-R^R$ is independently saturated aliphatic $C_{1-3}$alkyl.

In one embodiment, m is 0 or 1.
In one embodiment, m is 0.
In one embodiment, m is 1.
In one embodiment, $-R^Q$, if present, is attached at the 2- or 6-position of the morpholino group.
In one embodiment, $-R^Q$, if present, is attached at the 3- or 5-position of the morpholino group.

The Group $Q^3$: Chirality

If $-R^Q$ is present, then at least the ring carbon atom to which $-R^Q$ is attached is a chiral centre, and such compounds are expected to be optically active. Some examples of the stereoisomers are shown below.

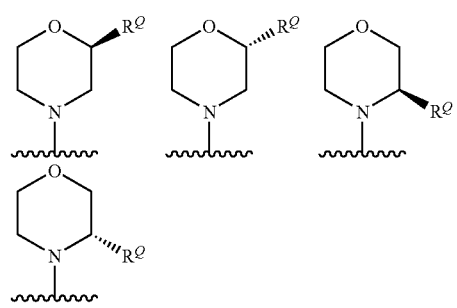

If one or more additional substitutents, $-R^P$, are also present, then the ring carbon atoms to which they are attached will also be chiral centres. Some examples of the stereoisomers are shown below.

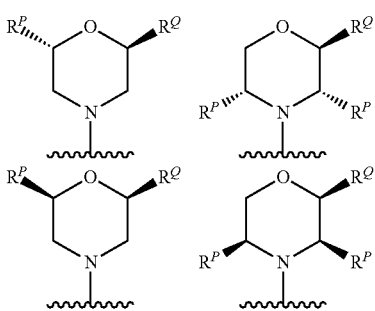

Each chiral centre, if present, is independently in the R-configuration or the S-configuration.

If no configuration is indicated, then both configurations are encompassed.

In one embodiment, —R$^Q$ is present (i.e., m is 1) and the ring carbon atom to which a group —R$^Q$ is attached is in the R-configuration.

In one embodiment, —R$^Q$ is present (i.e., m is 1) and the ring carbon atom to which a group —R$^Q$ is attached is in the S-configuration.

The Group -Q$^3$: —R$^Q$

In one embodiment, —R$^Q$, if present, is independently:
-L$^R$-NH$_2$, -L$^R$-NHR$^R$, -L$^R$-NR$^R_2$,
—C(=O)OH, —C(=O)OR$^R$,
—C(=O)NH$_2$, —C(=O)NHR$^R$, —C(=O)NR$^R_2$,
-L$^R$-C(=O)OH, -L$^R$-C(=O)OR$^R$,
-L$^R$-C(=O)NH$_2$, -L$^R$-C(=O)NHR$^R$, -L$^R$-C(=O)NR$^R_2$, or
-L$^R$-CN.

In one embodiment, —R$^Q$, if present, is independently:
-L$^R$-NH$_2$, -L$^R$-NHR$^R$, -L$^R$-NR$^R_2$,
—C(=O)NH$_2$, —C(=O)NHR$^R$, —C(=O)NR$^R_2$,
-L$^R$-C(=O)NH$_2$, -L$^R$-C(=O)NHR$^R$, or -L$^R$-C(=O)NR$^R_2$.

In one embodiment, —R$^Q$, if present, is independently:
-L$^R$-NH$_2$, -L$^R$-NHR$^R$, or -L$^R$-NR$^R_2$.

In one embodiment, —R$^Q$, if present, is independently:
—C(=O)NH$_2$, —C(=O)NHR$^R$, —C(=O)NR$^R_2$,
-L$^R$-C(=O)NH$_2$, -L$^R$-C(=O)NHR$^R$, or -L$^R$-C(=O)NR$^R_2$.

In one embodiment, —R$^Q$, if present, is independently -L$^R$-CN.

In one embodiment, each -L$^R$-, if present, is independently —(CH$_2$)—, —(CH$_2$)$_2$—, or —(CH$_2$)$_3$—.

In one embodiment, each -L$^R$-, if present, is independently —(CH$_2$)—.

In one embodiment, each -L$^R$-, if present, is independently —(CH$_2$)$_2$—.

In one embodiment, each -L$^R$-, if present, is independently —(CH$_2$)$_3$—.

In one embodiment, each —R$^R$, if present, is independently -Me or -Et.

In one embodiment, —R$^Q$, if present, is independently:
—(CH$_2$)—NH$_2$, —(CH$_2$)$_2$—NH$_2$, —(CH$_2$)$_3$—NH$_2$,
—(CH$_2$)—NHMe, —(CH$_2$)$_2$—NHMe, —(CH$_2$)$_3$—NHMe,
—(CH$_2$)—NHEt, —(CH$_2$)$_2$—NHEt, —(CH$_2$)$_3$—NHEt,
—(CH$_2$)—NMe$_2$, —(CH$_2$)$_2$—NMe$_2$, —(CH$_2$)$_3$—NMe$_2$,
—(CH$_2$)—NEt$_2$, —(CH$_2$)$_2$—NEt$_2$, —(CH$_2$)$_3$—NEt$_2$,
—(CH$_2$)—OH, —(CH$_2$)$_2$—OH, —(CH$_2$)$_3$—OH,
—(CH$_2$)—OMe, —(CH$_2$)$_2$—OMe, —(CH$_2$)$_3$—OMe,
—(CH$_2$)—OEt, —(CH$_2$)$_2$—OEt, —(CH$_2$)$_3$—OEt,
—COOH,
—COOMe, —COOEt,
—CONH$_2$,
—CONHMe, —CONHEt,
—CONMe$_2$, —CONEt$_2$,
—(CH$_2$)—COOH, —(CH$_2$)$_2$—COOH, —(CH$_2$)$_3$—COOH,
—(CH$_2$)—COOMe, —(CH$_2$)$_2$—COOMe, —(CH$_2$)$_3$—COOMe,
—(CH$_2$)—COOEt, —(CH$_2$)$_2$—COOEt, —(CH$_2$)$_3$—COOEt,
—(CH$_2$)—CONH$_2$, —(CH$_2$)$_2$—CONH$_2$, —(CH$_2$)$_3$—CONH$_2$,
—(CH$_2$)—CONHMe, —(CH$_2$)$_2$—CONHMe, —(CH$_2$)$_3$—CONHMe,
—(CH$_2$)—CONHEt, —(CH$_2$)$_2$—CONHEt, —(CH$_2$)$_3$—CONHEt,
—(CH$_2$)—CONMe$_2$, —(CH$_2$)$_2$—CONMe$_2$, —(CH$_2$)$_3$—CONMe$_2$,
—(CH$_2$)—CONEt$_2$, —(CH$_2$)$_2$—CONEt$_2$, —(CH$_2$)$_3$—CONEt$_2$,
—(CH$_2$)—CN, —(CH$_2$)$_2$—CN, or —(CH$_2$)$_3$—CN.

In one embodiment, —R$^Q$, if present, is independently:
—(CH$_2$)—NH$_2$, —(CH$_2$)$_2$—NH$_2$, —(CH$_2$)$_3$—NH$_2$,
—(CH$_2$)—NHMe, —(CH$_2$)$_2$—NHMe, —(CH$_2$)$_3$—NHMe,
—(CH$_2$)—NHEt, —(CH$_2$)$_2$—NHEt, —(CH$_2$)$_3$—NHEt,
—(CH$_2$)—NMe$_2$, —(CH$_2$)$_2$—NMe$_2$, —(CH$_2$)$_3$—NMe$_2$,
—(CH$_2$)—NEt$_2$, —(CH$_2$)$_2$—NEt$_2$, or —(CH$_2$)$_3$—NEt$_2$.

In one embodiment, —R$^Q$, if present, is independently:
—(CH$_2$)—NH$_2$, —(CH$_2$)—NHMe, —(CH$_2$)—NHEt, —(CH$_2$)—NMe$_2$, or —(CH$_2$)—NEt$_2$.

In one embodiment, —R$^Q$, if present, is independently —(CH$_2$)—NH$_2$.

In one embodiment, —R$^Q$, if present, is —(CH$_2$)$_p$—NH$_2$ (wherein p is independently 1, 2, or 3); —R$^Q$ is attached at the 2- or 6-position; and n is 0, as in, for example, the following group:

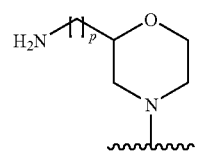

In one embodiment, —R$^Q$, if present, is —CH$_2$—NH$_2$; —R$^Q$ is attached at the 2- or 6-position; and n is 0, as in, for example, the following group:

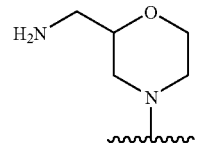

The Group Q$^3$: —R$^P$

In one embodiment, n is independently 0, 1, or 2.
In one embodiment, n is independently 0 or 1.
In one embodiment, n is independently 0.
A group, —R$^P$, if present, may be attached at the same position as a group —R$^Q$ (if present), or at a different position than the group —R$^Q$ (if present).

In one embodiment, a group —R$^P$ is attached at the same position as a group —R$^Q$, as in, for example, the following groups:

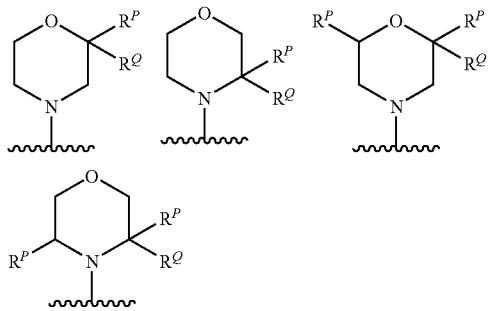

In one embodiment, any groups —R$^P$ are attached at different positions than a group —R$^Q$ (i.e., are not attached at the same position as a group —R$^Q$), as in, for example, the following groups:

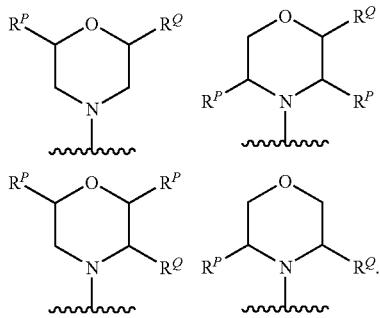

In one embodiment, each —R$^P$, if present, is independently saturated aliphatic C$_{1-3}$alkyl or —CF$_3$.

In one embodiment, each —R$^P$, if present, is independently saturated aliphatic C$_{1-3}$alkyl.

In one embodiment, each —R$^P$, if present, is independently -Me, -Et, or —CF$_3$.

In one embodiment, each —R$^P$, if present, is independently -Me.

In one embodiment, -Q$^3$, if present, is selected from the following groups (which are examples of cases where n is 1 or 2 and each R$^P$ is -Me):

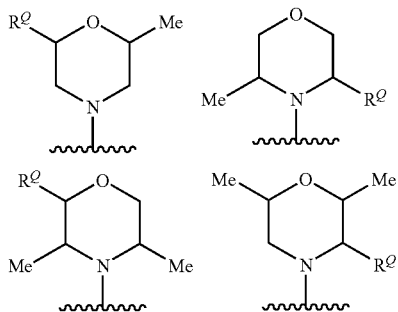

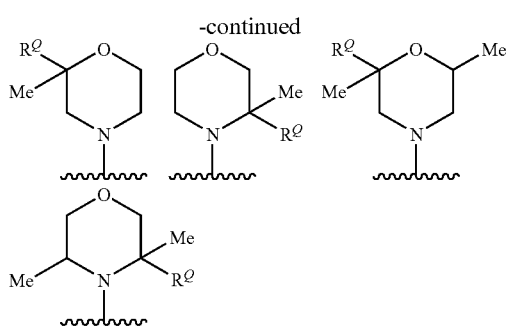

In one embodiment, -Q$^3$, if present, is selected from the following groups (which are examples of cases where n is 1 or 2, each R$^P$ is -Me, and R$^Q$ is —CH$_2$—NH$_2$):

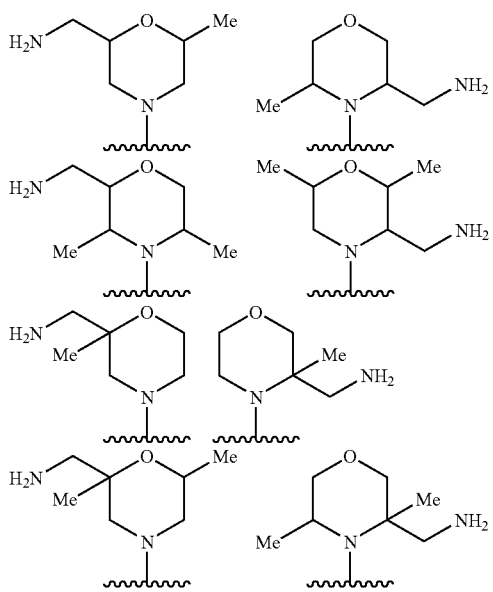

The Group -Q$^4$

In one embodiment, -Q$^4$ is independently:
—NH-L$^T$-NH$_2$, —NH-L$^T$-NHR$^{T1}$, —NH-L$^T$-NR$^{T1}$$_2$, —NH-L$^T$-NR$^{T2}$R$^{T3}$,
—NR$^{T1}$-L$^T$-NH$_2$, —NR$^{T1}$-L$^T$-NHR$^{T1}$, —NR$^{T1}$-L$^T$-NR$^{T1}$$_2$, —NR$^{T1}$-L$^T$-NR$^{T2}$R$^{T3}$;
—NH-L$^T$-NHC(=O)R$^{T1}$, —NH-L$^T$-N(R$^{T1}$)C(=O)R$^{T1}$, —N(R$^{T1}$)-L$^T$-NHC(=O)R$^{T1}$, or —N(R$^{T1}$)-L$^T$-N(R$^{T1}$)C(=O)R$^{T1}$, wherein:
each -L$^T$- is independently saturated aliphatic C$_{1-6}$alkylene;
in each group —NR$^{T2}$R$^{T3}$, R$^{T2}$ and R$^{T3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O; and
each —R$^{T1}$ is independently:
—R$^{U1}$, —R$^{U2}$, —R$^{U3}$, —R$^{U4}$, —R$^{U5}$, —R$^{U6}$, —R$^{U7}$, —R$^{U8}$,
-L$^U$-R$^{U4}$, -L$^U$-R$^{U5}$, -L$^U$-R$^{U6}$, -L$^U$-R$^{U7}$, or -L$^U$-R$^{U8}$;

wherein:
   each —$R^{U1}$ is independently saturated aliphatic $C_{1-6}$alkyl;
   each —$R^{U2}$ is independently aliphatic $C_{2-6}$alkenyl;
   each —$R^{U3}$ is independently aliphatic $C_{2-6}$alkynyl;
   each —$R^{U4}$ is independently saturated $C_{3-6}$cycloalkyl;
   each —$R^{U5}$ is independently $C_{3-6}$cycloalkenyl;
   each —$R^{U6}$ is independently non-aromatic $C_{3-7}$heterocyclyl;
   each —$R^{U7}$ is independently $C_{6-10}$carboaryl;
   each —$R^{U8}$ is independently $C_{5-10}$heteroaryl;
   each -$L^{U}$- is independently saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{5-10}$heteroaryl, and $C_{1-3}$alkylene is optionally substituted, for example, with one or more substituents —$R^{U9}$, wherein each —$R^{U9}$, if present, is independently:
   —F, —Cl, —Br, —I,
   —$R^{V1}$,
   —$CF_3$,
   —OH,
   —$OR^{V1}$,
   —$OCF_3$,
   —SH,
   —$SR^{V1}$,
   —CN,
   —$NO_2$,
   —$NH_2$, —$NHR^{V1}$, —$NR^{V1}_2$, —$NR^{V2}R^{V3}$,
   —C(=O)OH,
   —C(=O)$OR^{V1}$,
   —C(=O)$NH_2$, —C(=O)$NHR^{V1}$, —C(=O)$NR^{V1}_2$, —C(=O)$NR^{V2}R^{V3}$,
   -$L^{V}$-OH, -$L^{V}$-$OR^{V1}$,
   -$L^{V}$-$NH_2$, -$L^{V}$-$NHR^{V1}$, -$L^{V}$-$NR^{V1}_2$, or -$L^{V}$-$NR^{V2}R^{V3}$;
wherein:
   each —$R^{V1}$ is independently saturated aliphatic $C_{1-4}$alkyl, phenyl, or benzyl;
   each -$L^{V}$- is independently saturated aliphatic $C_{1-5}$alkylene; and
   in each group —$NR^{V2}R^{V3}$, $R^{V2}$ and $R^{V3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$Q^4$ is independently:
—NH-$L^T$-$NH_2$, —NH-$L^T$-$NHR^{T1}$, —NH-$L^T$-$NR^{T1}_2$, —NH-$L^T$-$NR^{T2}R^{T3}$,
—$NR^{T1}$-$L^T$-$NH_2$, —$NR^{T1}$-$L^T$-$NHR^{T1}$, —$NR^{T1}$-$L^T$-$NR^{T1}_2$, —$NR^{T1}$-$L^T$-$NR^{T2}R^{T3}$;
—NH-$L^T$-NHC(=O)$R^{T1}$, —NH-$L^T$-N($R^{T1}$)C(=O)$R^{T1}$, —N($R^{T1}$)-$L^T$-NHC(=O)$R^{T1}$, or —N($R^{T1}$)-$L^T$-N($R^{T1}$)C(=O)$R^{T1}$.

In one embodiment, -$Q^4$ is independently:
—NH-$L^T$-$NH_2$, —NH-$L^T$-$NHR^{T1}$, —NH-$L^T$-$NR^{T1}_2$, —NH-$L^T$-$NR^{T2}R^{T3}$,
—NH-$L^T$-NHC(=O)$R^{T1}$, or —NH-$L^T$-N($R^{T1}$)C(=O)$R^{T1}$.

In one embodiment, -$Q^4$ is independently:
—NH-$L^T$-$NH_2$, —NH-$L^T$-$NHR^{T1}$, —NH-$L^T$-$NR^{T1}_2$, or —NH-$L^T$-$NR^{T2}R^{T3}$.

In one embodiment, -$Q^4$ is independently:
—NH-$L^T$-NHC(=O)$R^{T1}$ or —NH-$L^T$-N($R^{T1}$)C(=O)$R^{T1}$.

In one embodiment, each -$L^T$- is independently saturated aliphatic $C_{1-6}$alkylene.
In one embodiment, each -$L^T$- is independently saturated aliphatic $C_{2-6}$alkylene.
In one embodiment, each -$L^T$- is independently saturated aliphatic $C_{3-6}$alkylene.
In one embodiment, each -$L^T$- is independently saturated aliphatic $C_{2-4}$alkylene.
In one embodiment, each -$L^T$- is independently saturated aliphatic $C_{2-3}$alkylene.
In one embodiment, each -$L^T$- is independently saturated linear $C_{1-6}$alkylene.
In one embodiment, each -$L^T$- is independently —$CH_2CH_2$— or —$CH_2CH_2CH_2$—.
In one embodiment, each —$NR^{T2}R^{T3}$, if present, is independently pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.
In one embodiment, each —$NR^{T2}R^{T3}$, if present, is independently pyrrolidino, piperidino, piperizino, or morpholino, and is optionally substituted, for example, with one or more groups selected from $C_{1-3}$alkyl and —$CF_3$.
In one embodiment, each —$R^{T1}$ is independently:
   —$R^{U1}$, —$R^{U4}$, —$R^{U7}$, —$R^{U8}$,
   -$L^U$-$R^{U4}$, or -$L^U$-$R^{U8}$.
In one embodiment, each —$R^{T1}$, if present, is independently —$R^{U1}$.
In one embodiment, each -$L^U$-, if present, is independently —$CH_2$—.
In one embodiment, each —$R^{U6}$, if present, is independently pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.
In one embodiment, each —$R^{U7}$, if present, is independently phenyl, and is optionally substituted.
In one embodiment, each —$R^{U8}$, if present, is independently $C_{5-6}$heteroaryl, and is optionally substituted.
In one embodiment, each —$R^{U8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.
In one embodiment, each —$R^{U9}$, if present, is independently:
   —F, —Cl, —Br, —I,
   —$R^{V1}$,
   —$CF_3$,
   —OH,
   —$OR^{V1}$,
   —$OCF_3$,
   —$NH_2$, —$NHR^{V1}$, —$NR^{V1}_2$, —$NR^{V2}R^{V3}$,
   —C(=O)OH,
   —C(=O)$OR^{V1}$,
   —C(=O)$NH_2$, —C(=O)$NHR^{V1}$, —C(=O)$NR^{V1}_2$, —C(=O)$NR^{V2}R^{V3}$,
   -$L^{V}$-$OR^{V1}$,
   -$L^{V}$-$NH_2$, -$L^{V}$-$NHR^{V1}$, -$L^{V}$-$NR^{V1}_2$, or -$L^{V}$-$NR^{V2}R^{V3}$.
In one embodiment, each -$L^V$-, if present, is independently saturated aliphatic $C_{1-3}$alkylene.
In one embodiment, each —$R^{V1}$, if present, is independently $C_{1-4}$alkyl.
In one embodiment, each —$NR^{V2}R^{V3}$, if present, is independently pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{V2}R^{V3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{U9}$, if present, is independently —F, —Cl, —Br, —I, -Me, -Et, —$CF_3$, —OH, —OMe, —OEt, —$OCF_3$, —$NH_2$, —NHMe, or —$NMe_2$ The Group -$Q^5$ In one embodiment, the group -$Q^5$ is as defined herein for -$Q^3$, but with the additional limitation that m is 1.

The Group $G^1$

In one embodiment, -$G^1$ is independently:
- —F, —Cl, —Br, —I,
- —$R^{A1}$,
- —$CF_3$,
- —OH,
- -$L^A$-OH,
- —$OR^{A1}$,
- -$L^A$-$OR^{A1}$,
- —$OCF_3$,
- —SH,
- —$SR^{A1}$,
- —CN,
- —$NO_2$,
- —$NH_2$, —$NHR^{A1}$, —$NR^{A1}{}_2$, —$NR^{A2}R^{A3}$,
- -$L^A$-$NH_2$, -$L^A$-$NHR^{A1}$, -$L^A$-$NR^{A1}{}_2$, -$L^A$-$NR^{A2}R^{A3}$,
- —C(=O)OH,
- —C(=O)$OR^{A1}$,
- —C(=O)$NH_2$, —C(=O)$NHR^{A1}$, —C(=O)$NR^{A1}{}_2$, —C(=O)$NR^{A2}R^{A3}$,
- —NHC(=O)$R^{A1}$, —$NR^{A1}$C(=O)$R^{A1}$,
- —NHC(=O)$OR^{A1}$, —$NR^{A1}$C(=O)$OR^{A1}$,
- —OC(=O)$NH_2$, —OC(=O)$NHR^{A1}$, —OC(=O)$NR^{A1}{}_2$,
- —OC(=O)$R^{A1}$,
- —C(=O)$R^{A1}$,
- —NHC(=O)$NH_2$, —NHC(=O)$NHR^{A1}$,
- —NHC(=O)$NR^{A1}{}_2$, —NHC(=O)$NR^{A2}R^{A3}$,
- —$NR^{A1}$C(=O)$NH_2$, —$NR^{A1}$C(=O)$NHR^{A1}$,
- —$NR^{A1}$C(=O)$NR^{A1}{}_2$, —$NR^{A1}$C(=O)$NR^{A2}R^{A3}$,
- —NHS(=O)$_2R^{A1}$, —$NR^{A1}$S(=O)$_2R^{A1}$,
- —S(=O)$_2NH_2$, —S(=O)$_2NHR^{A1}$, —S(=O)$_2NR^{A1}{}_2$,
- —S(=O)$_2NR^{A2}R^{A3}$,
- —S(=O)$R^{A1}$,
- —S(=O)$_2R^{A1}$,
- —OS(=O)$_2R^{A1}$, or
- —S(=O)$_2OR^{A1}$, wherein:
- each -$L^A$- is independently saturated aliphatic $C_{1-6}$alkylene;
- in each group —$NR^{A2}R^{A3}$, $R^{A2}$ and $R^{A3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
- each —$R^{A1}$ is independently:
  - —$R^{B1}$, —$R^{B2}$, —$R^{B3}$, —$R^{B4}$, —$R^{B5}$, —$R^{B6}$, —$R^{B7}$, —$R^{B8}$,
  - -$L^B$-$R^{B4}$, -$L^B$-$R^{B5}$, -$L^B$-$R^{B6}$, -$L^B$-$R^{B7}$, or -$L^B$-$R^{B8}$;
- wherein:
  - each —$R^{B1}$ is independently saturated aliphatic $C_{1-6}$alkyl;
  - each —$R^{B2}$ is independently aliphatic $C_{2-6}$alkenyl;
  - each —$R^{B3}$ is independently aliphatic $C_{2-6}$alkynyl;
  - each —$R^{B4}$ is independently saturated $C_{3-6}$cycloalkyl;
  - each —$R^{B5}$ is independently $C_{3-6}$cycloalkenyl;
  - each —$R^{B6}$ is independently non-aromatic $C_{3-7}$heterocyclyl;
  - each —$R^{B7}$ is independently $C_{6-10}$carboaryl;
  - each —$R^{B8}$ is independently $C_{6-10}$heteroaryl;
  - each -$L^B$- is independently saturated aliphatic $C_{1-3}$alkylene;

and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{6-10}$heteroaryl, and $C_{1-3}$alkylene is optionally substituted, for example, with one or more substituents —$R^{B9}$, wherein each —$R^{B9}$ is independently:
- —F, —Cl, —Br, —I,
- —$CF_3$,
- —OH,
- —$OR^{C1}$,
- $OR^{C1}$,
- —$OCF_3$,
- —SH,
- —$SR^{C1}$,
- —CN,
- —$NO_2$,
- —$NH_2$, —$NHR^{C1}$, —$NR^{C1}{}_2$, —$NR^{C2}R^{C3}$,
- —C(=O)OH,
- —C(=O)$OR^{C1}$,
- —C(=O)$NH_2$, —C(=O)$NHR^{C1}$, —C(=O)$NR^{C1}{}_2$, —C(=O)$NR^{C2}R^{C3}$,
- -$L^C$-OH, -$L^C$-$OR^{C1}$,
- -$L^C$-$NH_2$, -$L^C$-$NHR^{C1}$, -$L^C$-$NR^{C1}{}_2$, or -$L^C$-$NR^{C2}R^{C3}$;

wherein:
each —$R^{C1}$ is independently saturated aliphatic $C_{1-4}$alkyl, phenyl, or benzyl;
each -$L^C$- is independently saturated aliphatic $C_{1-5}$alkylene; and
in each group —$NR^{C2}R^{C3}$, $R^{C2}$ and $R^{C3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$G^1$, if present, is independently:
- —F, —Cl, —Br, —I,
- —$R^{A1}$,
- —$CF_3$,
- —OH,
- -$L^A$-OH,
- —$OR^{A1}$,
- -$L^A$-$OR^{A1}$,
- —$OCF_3$,
- —CN,
- —$NH_2$, —$NHR^{A1}$, —$NR^{A1}{}_2$, —$NR^{A2}R^{A3}$,
- -$L^A$-$NH_2$, -$L^A$-$NHR^{A1}$, -$L^A$-$NR^{A1}{}_2$, -$L^A$-$NR^{A2}R^{A3}$,
- —C(=O)OH,
- —C(=O)$OR^{A1}$,
- —C(=O)$NH_2$, —C(=O)$NHR^{A1}$, —C(=O)$NR^{A1}{}_2$, —C(=O)$NR^{A2}R^{A3}$,
- —NHC(=O)$R^{A1}$, —$NR^{A1}$C(=O)$R^{A1}$,
- —OC(=O)$R^{A1}$, or
- —C(=O)$R^{A1}$.

In one embodiment, -G$^1$, if present, is independently:
—F, —Cl, —Br, —I,
—R$^{A1}$,
—CF$_3$,
—OH,
-L$^A$-OH,
—OR$^{A1}$,
-L$^A$-OR$^{A1}$,
—OCF$_3$,
—CN,
—NH$_2$, —NHR$^{A1}$, —NR$^{A1}$$_2$, —NR$^{A2}$R$^{A3}$,
-L$^A$-NH$_2$, -L$^A$-NHR$^{A1}$, -L$^A$-NR$^{A1}$$_2$, -L$^A$-NR$^{A2}$R$^{A3}$,
—NHC(=O)R$^{A1}$, or —NR$^{A1}$C(=O)R$^{A1}$.

In one embodiment, -G$^1$, if present, is independently —NH$_2$, —NHR$^{A1}$, —NR$^{A1}$$_2$, or —NR$^{A2}$R$^{A3}$.

In one embodiment, -G$^1$, if present, is independently —NH$_2$ or —NHR$^{A1}$.

In one embodiment, -G$^1$, if present, is independently —NH$_2$.

In one embodiment, each -L$^A$-, if present, is independently saturated aliphatic C$_{1-3}$alkylene.

In one embodiment, each —NR$^{A2}$R$^{A3}$, if present, is independently pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{A2}$R$^{A3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{A1}$, if present, is independently:
—R$^{B1}$, —R$^{B4}$, —R$^{B7}$, —R$^{B8}$,
-L$^B$-R$^{B4}$, -L$^B$-R$^{B7}$, or -L$^B$-R$^{B8}$.

In one embodiment, each —R$^{A1}$, if present, is independently:
—R$^{B1}$, —R$^{B4}$, —R$^{B8}$,
-L$^B$-R$^{B4}$, or -L$^B$-R$^{B8}$.

In one embodiment, each —R$^{A1}$, if present, is independently —R$^{B1}$.

In one embodiment, each -L$^B$-, if present, is independently —CH$_2$—.

In one embodiment, each —R$^{B6}$, if present, is independently pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —R$^{B7}$, if present, is independently phenyl, and is optionally substituted.

In one embodiment, each —R$^{B8}$, if present, is independently C$_{5-6}$heteroaryl, and is optionally substituted.

In one embodiment, each —R$^{B8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —R$^{B9}$, if present, is independently:
—F, —Cl, —Br, —I,
—R$^{C1}$,
—CF$_3$,
—OH,
—OR$^{C1}$,
—OCF$_3$,
—NH$_2$, —NHR$^{C1}$, —NR$^{C1}$$_2$, —NR$^{C2}$R$^{C3}$,
—C(=O)OH,
—C(=O)OR$^{C1}$,
—C(=O)NH$_2$, —C(=O)NHR$^{C1}$, —C(=O)NR$^{C1}$$_2$,
—C(=O)NR$^{C2}$R$^{C3}$,
-L$^C$-OH, -L$^C$-OR$^{C1}$,
-L$^C$-NH$_2$, -L$^C$-NHR$^{C1}$, -L$^C$-NR$^{C1}$$_2$, or -L$^C$-NR$^{C2}$R$^{C3}$.

In one embodiment, each -L$^C$-, if present, is independently saturated aliphatic C$_{1-3}$alkylene.

In one embodiment, each —R$^{C1}$, if present, is independently C$_{1-4}$alkyl.

In one embodiment, each —NR$^{C2}$R$^{C3}$, if present, is independently pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{C2}$R$^{C3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{B9}$, if present, is independently —F, —Cl, —Br, —I, -Me, -Et, —CF$_3$, —OH, —OMe, —OEt, —OCF$_3$, —NH$_2$, —NHMe, or —NMe$_2$.

The Group G$^2$

In one embodiment, -G$^2$ is independently:
—F, —Cl, —Br, —I,
—R$^{E1}$,
—CF$_3$,
—OH,
-L$^E$-OH,
—OR$^{E1}$,
-L$^E$-OR$^{E1}$,
—OCF$_3$,
—SH,
—SR$^{E1}$,
—CN,
—NO$_2$,
—NH$_2$, —NHR$^{E1}$, —NR$^{E1}$$_2$, —NR$^{E2}$R$^{E3}$,
-L$^E$-NH$_2$, -L$^E$-NHR$^{E1}$, -L$^E$-NR$^{E1}$$_2$, -L$^E$-NR$^{E2}$R$^{E3}$,
—C(=O)OH,
—C(=O)OR$^{E1}$,
—C(=O)NH$_2$, —C(=O)NHR$^{E1}$, —C(=O)NR$^{E1}$$_2$,
—C(=O)NR$^{E2}$R$^{E3}$,
—NHC(=O)R$^{E1}$, —NR$^{E1}$C(=O)R$^{E1}$,
—NHC(=O)OR$^{E1}$, —NR$^{E1}$C(=O)OR$^{E1}$,
—OC(=O)NH$_2$, —OC(=O)NHR$^{E1}$, —OC(=O)NR$^{E1}$$_2$,
—OC(=O)R$^{E1}$,
—C(=O)R$^{E1}$,
—NHC(=O)NH$_2$, —NHC(=O)NHR$^{E1}$,
—NHC(=O)NR$^{E1}$$_2$, —NHC(=O)NR$^{E2}$R$^{E3}$,
—NR$^{E1}$C(=O)NH$_2$, —NR$^{E1}$C(=O)NHR$^{E1}$,
—NR$^{E1}$C(=O)NR$^{E1}$$_2$, —NR$^{E1}$C(=O)NR$^{E2}$R$^{E3}$,
—NHS(=O)$_2$R$^{E1}$, —NR$^{E1}$S(=O)$_2$R$^{E1}$,
—S(=O)$_2$NH$_2$, —S(=O)$_2$NHR$^{E1}$, —S(=O)$_2$NR$^{E1}$$_2$,
—S(=O)$_2$NR$^{E2}$R$^{E3}$,
—S(=O)R$^{E1}$,
—S(=O)$_2$R$^{E1}$,
—OS(=O)$_2$R$^{E1}$, or
—S(=O)$_2$OR$^{E1}$,
wherein:
each -L$^E$- is independently saturated aliphatic C$_{1-5}$alkylene;
in each group —NR$^{E2}$R$^{E3}$, R$^{E2}$ and R$^{E3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{E1}$ is independently:
 —$R^{F1}$, —$R^{F2}$, —$R^{F3}$, —$R^{F5}$, —$R^{F6}$, —$R^{F7}$, —$R^{F8}$,
 -$L^F$-$R^{F4}$, -$L^F$-$R^{F5}$, -$L^F$-$R^{F6}$, -$L^F$-$R^{F7}$, or -$L^F$-$R^{F8}$;
wherein:
 each —$R^{F1}$ is independently saturated aliphatic $C_{1-6}$alkyl;
 each —$R^{F2}$ is independently aliphatic $C_{2-6}$alkenyl;
 each —$R^{F3}$ is independently aliphatic $C_{2-6}$alkynyl;
 each —$R^{F4}$ is independently saturated $C_{3-6}$cycloalkyl;
 each —$R^{F5}$ is independently $C_{3-6}$cycloalkenyl;
 each —$R^{F6}$ is independently non-aromatic $C_{3-7}$heterocyclyl;
 each —$R^{F7}$ is independently $C_{6-10}$carboaryl;
 each —$R^{F8}$ is independently $C_{6-10}$heteroaryl;
 each -$L^F$- is independently saturated aliphatic $C_{1-3}$alkylene;
and wherein:
 each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{6-10}$heteroaryl, and $C_{1-3}$alkylene is optionally substituted, for example, with one or more substituents —$R^{F9}$, wherein each —$R^{F9}$, if present, is independently:
 —F, —Cl, —Br, —I,
 —$R^{G1}$,
 —$CF_3$,
 —OH,
 —$OR^{G1}$,
 —$OCF_3$,
 —SH,
 —$SR^{G1}$,
 —CN,
 —$NO_2$,
 —$NH_2$, —$NHR^{G1}$, —$NR^{G1}{}_2$, —$NR^{G2}R^{G3}$,
 —C(=O)OH,
 —C(=O)$OR^{G1}$,
 —C(=O)$NH_2$, —C(=O)$NHR^{G1}$, —C(=O)$NR^{G1}{}_2$, —C(=O)$NR^{G2}R^{G3}$,
 -$L^G$-OH, -$L^G$-$OR^{G1}$,
 -$L^G$-$NH_2$, -$L^G$-$NHR^{G1}$, -$L^G$-$NR^{G1}{}_2$, or -$L^G$-$NR^{G2}R^{G3}$;
wherein:
 each —$R^{G1}$ is independently saturated aliphatic $C_{1-4}$alkyl, phenyl, or benzyl;
 each -$L^G$- is independently saturated aliphatic $C_{1-5}$alkylene; and
 in each group —$NR^{G2}R^{G3}$, $R^{G2}$ and $R^{G3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.
In one embodiment, -$G^2$, if present, is independently:
 —F, —Cl, —Br, —I,
 —$R^{E1}$,
 —$CF_3$,
 —OH,
 -$L^E$-OH,
 —$OR^{E1}$,
 -$L^E$-$OR^{E1}$,
 —$OCF_3$,
 —CN,
 —$NH_2$, —$NHR^{E1}$, —$NR^{E1}{}_2$, —$NR^{E2}R^{E3}$,
 -$L^E$-$NH_2$, -$L^E$-$NHR^{E1}$, -$L^E$-$NR^{E1}{}_2$, -$L^E$-$NR^{E2}R^{E3}$,
 —C(=O)OH,
 —C(=O)$OR^{E1}$,
 —C(=O)$NH_2$, —C(=O)$NHR^{E1}$, —C(=O)$NR^{E1}{}_2$,
 —C(=O)$NR^{E2}R^{E3}$,
 —NHC(=O)$R^{E1}$, —$NR^{E1}$C(=O)$R^{E1}$,
 —OC(=O)$R^{E1}$, or
 —C(=O)$R^{E1}$.
In one embodiment, -$G^2$, if present, is independently:
 —F, —Cl, —Br, —I,
 —$R^{E1}$,
 —$CF_3$,
 —OH,
 -$L^E$-OH,
 —$OR^{E1}$,
 -$L^E$-$OR^{E1}$,
 —$OCF_3$,
 —CN,
 —$NH_2$, —$NHR^{E1}$, —$NR^{E1}{}_2$, —$NR^{E2}R^{E3}$,
 -$L^E$-$NH_2$, -$L^E$-$NHR^{E1}$, -$L^E$-$NR^{E1}{}_2$, -$L^E$-$NR^{E2}R^{E3}$,
 —NHC(=O)$R^{E1}$, or —$NR^{E1}$C(=O)$R^{E1}$.
In one embodiment, -$G^2$, if present, is independently —$R^{E1}$, —OH, or —$OR^{E1}$.
In one embodiment, -$G^2$, if present, is independently —$R^{E1}$ or —$OR^{E1}$.
In one embodiment, each -$L^E$-, if present, is independently saturated aliphatic $C_{1-3}$alkylene.
In one embodiment, each —$NR^{E2}R^{E3}$, if present, is independently pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.
In one embodiment, each —$NR^{E2}R^{E3}$, if present, is independently pyrrolidino, piperidino, piperizino, or morpholino, and is optionally substituted, for example, with one or more groups selected from $C_{1-3}$alkyl and —$CF_3$.
In one embodiment, each —$R^{E1}$, if present, is independently:
 —$R^{F1}$, —$R^{F4}$, —$R^{F7}$, —$R^{F8}$,
 -$L^F$-$R^{F4}$, -$L^F$-$R^{F7}$, or -$L^F$-$R^{F8}$.
In one embodiment, each —$R^{E1}$, if present, is independently:
 —$R^{F1}$, —$R^{F4}$, —$R^{F8}$,
 -$L^F$-$R^{F4}$, or -$L^F$-$R^{F8}$.
In one embodiment, each —$R^{E1}$, if present, is independently —$R^{F1}$.
In one embodiment, each -$L^F$-, if present, is independently —$CH_2$—.
In one embodiment, each —$R^{F6}$, if present, is independently pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.
In one embodiment, each —$R^{F7}$, if present, is independently phenyl, and is optionally substituted.
In one embodiment, each —$R^{F8}$, if present, is independently $C_{5-6}$heteroaryl, and is optionally substituted.
In one embodiment, each —$R^{F8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.
In one embodiment, each —$R^{F9}$, if present, is independently
 —F, —Cl, —Br, —I,
 —$R^{G1}$,
 —$CF_3$,
 —OH,
 —$OR^{G1}$,
 —$OCF_3$,
 —$NH_2$, —$NHR^{G1}$, —$NR^{G1}{}_2$, —$NR^{G2}R^{G3}$, —C(=O)OH,
—C(=O)OR$^{G1}$,
—C(=O)NH$_2$, —C(=O)NHR$^{G1}$, —C(=O)NR$^{G1}_2$,
—C(=O)NR$^{G2}$R$^{G3}$,
-L$^G$-OH, -L$^G$-OR$^{G1}$,
-L$^G$-NH$_2$, -L$^G$-NHR$^{G1}$, -L$^G$-NR$^{G1}_2$, or -L$^G$-NR$^{G2}$R$^{G3}$.

In one embodiment, each -L$^G$-, if present, is independently saturated aliphatic C$_{1-3}$alkylene.

In one embodiment, each —R$^{G1}$, if present, is independently C$_{1-4}$alkyl.

In one embodiment, each —NR$^{G2}$R$^{G3}$, if present, is independently pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{G2}$R$^{G3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{F9}$, if present, is independently —F, —Cl, —Br, —I, -Me, -Et, —CF$_3$, —OH, —OMe, —OEt, —OCF$_3$, —NH$_2$, —NHMe, or —NMe$_2$.

The Group G$^3$

In one embodiment, -G$^3$ is independently:
—F, —Cl, —Br, —I,
—R$^{H1}$,
—CF$_3$,
—OH,
-L$^H$-OH,
-L$^H$-OR$^{H1}$,
—OCF$_3$,
—SH,
—SR$^{H1}$,
—CN,
—NO$_2$,
—NH$_2$, —NHR$^{H1}$, —NR$^{H1}_2$, —NR$^{H2}$R$^{H3}$,
-L$^H$-NH$_2$, -L$^H$-NHR$^{H1}$, -L$^H$-NR$^{H1}_2$, -L$^H$-NR$^{H2}$R$^{H3}$,
—C(=O)OH,
—C(=O)OR$^{H1}$,
—C(=O)NH$_2$, —C(=O)NHR$^{H1}$, —C(=O)NR$^{H1}_2$,
—C(=O)NR$^{H2}$R$^{H3}$,
—NHC(=O)R$^{H1}$, —NR$^{H1}$C(=O)R$^{H1}$,
—NHC(=O)OR$^{H1}$, —NR$^{H1}$C(=O)OR$^{H1}$,
—OC(=O)NH$_2$, —OC(=O)NHR$^{H1}$, —OC(=O)NR$^{H1}_2$,
—OC(=O)R$^{H1}$,
—C(=O)R$^{H1}$,
—NHC(=O)NH$_2$, —NHC(=O)NHR$^{H1}$,
—NHC(=O)NR$^{H1}_2$, —NHC(=O)NR$^{H2}$R$^{H3}$,
—NR$^{H1}$C(=O)NH$_2$, —NR$^{H1}$C(=O)NHR$^{H1}$,
—NR$^{H1}$C(=O)NR$^{H1}_2$, —NR$^{H1}$C(=O)NR$^{H2}$R$^{H3}$,
—NHS(=O)$_2$R$^{H1}$, —NR$^{H1}$S(=O)$_2$R$^{H1}$,
—S(=O)$_2$NH$_2$, —S(=O)$_2$NHR$^{H1}$, —S(=O)$_2$NR$^{H1}_2$,
—S(=O)$_2$NR$^{H2}$R$^{H3}$,
—S(=O)R$^{H1}$,
—S(=O)$_2$R$^{H1}$,
—OS(=O)$_2$R$^{H1}$, or
S(=O)$_2$OR$^{H1}$,
wherein:
each -L$^H$- is independently saturated aliphatic C$_{1-6}$alkylene;
in each group —NR$^{H2}$R$^{H3}$, R$^{H2}$ and R$^{H3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —R$^{H1}$ is independently:
—R$^{J1}$, —R$^{J2}$, —R$^{J3}$, —R$^{J4}$, —R$^{J5}$, —R$^{J6}$, —R$^{J7}$,
—R$^{J8}$,
-L$^J$-R$^{J4}$, -L$^J$-R$^{J5}$, -L$^J$-R$^{J6}$, -L$^J$-R$^{J7}$, or -L$^J$-R$^{J8}$;
wherein:
each —R$^{J1}$ is independently saturated aliphatic C$_{1-6}$alkyl;
each —R$^{J2}$ is independently aliphatic C$_{2-6}$alkenyl;
each —R$^{J3}$ is independently aliphatic C$_{2-6}$alkynyl;
each —R$^{J4}$ is independently saturated C$_{3-6}$cycloalkyl;
each —R$^{J5}$ is independently C$_{3-6}$cycloalkenyl;
each —R$^{J6}$ is independently non-aromatic C$_{3-7}$heterocyclyl;
each —R$^{J7}$ is independently C$_{6-10}$carboaryl;
each —R$^{J8}$ is independently C$_{6-10}$heteroaryl;
each -L$^a$- is independently saturated aliphatic C$_{1-3}$alkylene;
and wherein:
each C$_{1-6}$alkyl, C$_{2-6}$alkenyl, C$_{2-6}$alkynyl, C$_{3-6}$cycloalkyl, C$_{3-6}$cycloalkenyl, non-aromatic C$_{3-7}$heterocyclyl, C$_{6-10}$carboaryl, C$_{5-10}$heteroaryl, and C$_{1-3}$alkylene is optionally substituted with one or more substituents —R$^{J9}$, wherein each —R$^{J9}$, if present, is independently:
—F, —Cl, —Br, —I,
R$^{K1}$,
—CF$_3$,
—OH,
—OR$^{K1}$,
—OCF$_3$,
—SH,
—SR$^{K1}$,
—CN,
—NO$_2$,
—NH$_2$, —NHR$^{K1}$, —NR$^{K1}_2$, —NR$^{K2}$R$^{K3}$,
—C(=O)OH,
—C(=O)OR$^{K1}$,
—C(=O)NH$_2$, —C(=O)NHR$^{K1}$, —C(=O)NR$^{K1}_2$,
—C(=O)NR$^{K2}$R$^{K3}$,
-L$^K$-OH, -L$^K$-OR$^{K1}$,
-L$^K$-NH$_2$, -L$^K$-NHR$^{K1}$, -L$^K$-NR$^{K1}_2$, or -L$^K$-NR$^{K2}$R$^{K3}$;
wherein:
each —R$^{K1}$ is independently saturated aliphatic C$_{1-4}$alkyl, phenyl, or benzyl;
each -L$^K$- is independently saturated aliphatic C$_{1-6}$alkylene; and
in each group —NR$^{K2}$R$^{K3}$, R$^{K2}$ and R$^{K3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -G$^3$, if present, is independently:
—F, —Cl, —Br, —I,
—R$^{H1}$,
—CF$_3$,
—OH,
-L$^H$-OH,
—OR$^{H1}$,
-L$^H$-OR$^{H1}$,
—OCF$_3$,
—CN,
—NH$_2$, —NHR$^{H1}$, —NR$^{H1}_2$, —NR$^{H2}$R$^{H3}$,
-L$^H$-NH$_2$, -L$^H$-NHR$^{H1}$, -L$^H$-NR$^{H1}_2$, -L$^H$-NR$^{H2}$R$^{H3}$,
—C(=O)OH,
—C(=O)OR$^{H1}$, —C(=O)NH$_2$, —C(=O)NHR$^{H1}$, —C(=O)NR$^{H1}$$_2$,
  —C(=O)NR$^{H2}$R$^{H3}$,
—NHC(=O)R$^{H1}$, or —NR$^{H1}$C(=O)R$^{H1}$.

In one embodiment, -G$^3$, if present, is independently:
  —R$^{H1}$,
  —CN,
  —C(=O)OH,
  —C(=O)OR$^{H1}$,
  —C(=O)NH$_2$, —C(=O)NHR$^{H1}$, —C(=O)NR$^{H1}$$_2$, or
    —C(=O)NR$^{H2}$R$^{H3}$.

In one embodiment, -G$^3$, if present, is independently —CN.

In one embodiment, -G$^3$, if present, is independently —R$^{H1}$.

In one embodiment, -G$^3$, if present, is independently:
  —C(=O)OH,
  —C(=O)OR$^{H1}$,
  —C(=O)NH$_2$, —C(=O)NHR$^{H1}$, —C(=O)NR$^{H1}$$_2$, or
    —C(=O)NR$^{H2}$R$^{H3}$.

In one embodiment, each -L$^H$-, if present, is independently saturated aliphatic C$_{1-3}$alkylene.

In one embodiment, each —NR$^{H2}$R$^{H3}$, if present, is independently pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{H2}$R$^{H3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{H1}$, if present, is independently:
  —R$^{J1}$, —R$^{J4}$, —R$^{J7}$, —R$^{J8}$,
  -L$^J$-R$^{J4}$, or -L$^J$-R$^{J7}$, or -L$^J$-R$^{J8}$.

In one embodiment, each —R$^{H1}$, if present, is independently:
  —R$^{J1}$, —R$^{J4}$, —R$^{J8}$,
  -L$^J$-R$^{J4}$, or -L$^J$-R$^{J8}$.

In one embodiment, each —R$^{H1}$, if present, is independently —R$^{J1}$ or —R$^{J8}$.

In one embodiment, each —R$^{H1}$, if present, is independently —R$^{J1}$.

In one embodiment, each —R$^{H1}$, if present, is independently —R$^{J8}$.

In one embodiment, each -L$^J$-, if present, is independently —CH$_2$—.

In one embodiment, each —R$^{J6}$, if present, is independently pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —R$^{J7}$, if present, is independently phenyl, and is optionally substituted.

In one embodiment, each —R$^{J8}$, if present, is independently C$_{5-6}$heteroaryl, and is optionally substituted.

In one embodiment, each —R$^{J8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —R$^{J8}$, if present, is independently C$_5$heteroaryl, and is optionally substituted.

In one embodiment, each —R$^{J8}$, if present, is independently furanyl, thienyl, pyrrolyl, imidazolyl, pyrazolyl, triazolyl, oxazolyl, isoxazolyl, thiazolyl, or isothiazolyl, and is optionally substituted.

In one embodiment, each —R$^{J9}$, if present, is independently:
  —F, —Cl, —Br, —I,
  —R$^{K1}$,
  —CF$_3$,
  —OH,
  —OR$^{K1}$,
  —OCF$_3$,
  —NH$_2$, —NHR$^{K1}$, —NR$^{K1}$$_2$, —NR$^{K2}$R$^{K3}$,
  —C(=O)OH,
  —C(=O)OR$^{K1}$,
  —C(=O)NH$_2$, —C(=O)NHR$^{K1}$, —C(=O)NR$^{K1}$$_2$,
    —C(=O)NR$^{K2}$R$^{K3}$,
  -L$^K$-OH, -L$^K$-OR$^{K1}$,
  -L$^K$-NH$_2$, -L$^K$-NHR$^{K1}$, -L$^K$-NR$^{K1}$$_2$, or -L$^K$-NR$^{K2}$R$^{K3}$.

In one embodiment, each -L$^K$-, if present, is independently saturated aliphatic C$_{1-3}$alkylene.

In one embodiment, each —R$^{K1}$, if present, is independently C$_{1-4}$alkyl.

In one embodiment, each —NR$^{K2}$R$^{K3}$, if present, is independently pyrrolidino, imidazolidino, pyrazolidino, piperidino, piperizino, morpholino, azepino, or diazepino, and is optionally substituted, for example, with one or more groups selected from C$_{1-3}$alkyl and —CF$_3$.

In one embodiment, each —NR$^{K2}$R$^{K3}$, if present, is independently pyrrolidino, piperidino, piperizino, or morpholino, and is optionally substituted, for example, with one or more groups selected from C$_{1-3}$alkyl and —CF$_3$.

In one embodiment, each —R$^{J9}$, if present, is independently —F, —Cl, —Br, —I, -Me, -Et, —CF$_3$, —OH, —OMe, —OEt, —OCF$_3$, —NH$_2$, —NHMe, or —NMe$_2$.

The Group -G$^4$

In one embodiment, -G$^4$ is independently:
  —CN,
  R$^{L1}$,
  —CF$_3$,
  —C(=O)OH,
  —C(=O)OR$^{L1}$,
  —C(=O)NH$_2$, —C(=O)NHR$^{L1}$, —C(=O)NR$^{L1}$$_2$, or
    —C(=O)NR$^{L2}$R$^{L3}$;

wherein:
  in each group —NR$^{L2}$R$^{L3}$, R$^{L2}$ and R$^{L3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
  each —R$^{L1}$ is independently:
    —R$^{M1}$, —R$^{M2}$, —R$^{M3}$, —R$^{M4}$—R$^{M5}$, —R$^{M6}$, —R$^{M7}$,
      —R$^{M8}$,
    -L$^M$-R$^{M4}$, -L$^M$-R$^{M5}$, -L$^M$-R$^{M6}$, -L$^M$-R$^{M7}$, or -L$^M$-R$^{M8}$;
  wherein:
    each —R$^{M1}$ is independently saturated aliphatic C$_{1-6}$alkyl;
    each —R$^{M2}$ is independently aliphatic C$_{2-6}$alkenyl;
    each —R$^{M3}$ is independently aliphatic C$_{2-6}$alkynyl;
    each —R$^{M4}$ is independently saturated C$_{3-6}$cycloalkyl;
    each —R$^{M5}$ is independently C$_{3-6}$cycloalkenyl;
    each —R$^{M6}$ is independently non-aromatic C$_{3-7}$heterocyclyl;
    each —R$^{M7}$ is independently C$_{6-10}$carboaryl;
    each —R$^{M8}$ is independently C$_{5-10}$heteroaryl;
    each -L$^M$- is independently saturated aliphatic C$_{1-3}$alkylene;
  and wherein:
    each C$_{1-6}$alkyl, C$_{2-6}$alkenyl, C$_{2-6}$alkynyl, C$_{3-6}$cycloalkyl, C$_{3-6}$cycloalkenyl, non-aromatic C$_{3-7}$heterocyclyl, C$_{6-10}$carboaryl, C$_{6-10}$heteroaryl, and C$_{1-3}$alkylene is optionally substituted, for example, with one or more substituents —$R^{M9}$, wherein each —$R^{M9}$ is independently:
—F, —Cl, —Br, —I,
$R^{N1}$,
—$CF_3$,
—OH,
—$OR^{N1}$,
—$OCF_3$,
—SH,
—$SR^{N1}$,
—CN,
—$NO_2$,
—$NH_2$, —$NHR^{N1}$, —$NR^{N1}{}_2$, —$NR^{N2}R^{N3}$,
—C(=O)OH,
—C(=O)$OR^{N1}$,
—C(=O)$NH_2$, —C(=O)$NHR^{N1}$, —C(=O)$NR^{N1}{}_2$, —C(=O)$NR^{N2}R^{N3}$,
-$L^N$-OH, -$L^N$-$OR^{N1}$,
-$L^N$-$NH_2$, -$L^N$-$NHR^{N1}$, -$L^N$-$NR^{N1}{}_2$, or -$L^N$-$NR^{N2}R^{N3}$;
wherein:
each —$R^{N1}$ is independently saturated aliphatic $C_{1-4}$alkyl, phenyl, or benzyl;
each -$L^N$- is independently saturated aliphatic $C_{1-5}$alkylene; and
in each group —$NR^{N2}R^{N3}$, $R^{N2}$ and $R^{N3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$G^4$ is independently —CN.
In one embodiment, -$G^4$ is independently —$R^{L1}$.
In one embodiment, -$G^4$ is independently:
—C(=O)OH,
—C(=O)$OR^{L1}$,
—C(=O)$NH_2$, —C(=O)$NHR^{L1}$, —C(=O)$NR^{L1}{}_2$, or —C(=O)$NR^{L2}R^{L3}$.

In one embodiment, each —$NR^{L2}R^{L3}$, if present, is independently pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{L2}R^{L3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{L1}$, if present, is independently:
—$R^{M1}$, —$R^{M4}$, —$R^{M7}$, —$R^{M8}$,
-$L^M$-$R^{M4}$, -$L^M$-$R^{M7}$, or -$L^M$-$R^{M8}$.

In one embodiment, each —$R^B$, if present, is independently:
—$R^{M1}$, —$R^{M7}$, —$R^{M8}$,
-$L^M$-$R^{M7}$, or -$L^M$-$R^{M8}$.

In one embodiment, each —$R^{L1}$, if present, is independently —$R^{M1}$ or —$R^{M8}$.

In one embodiment, each —$R^{L1}$, if present, is independently —$R^{M1}$.

In one embodiment, each —$R^{L1}$, if present, is independently —$R^{M8}$.

In one embodiment, each -$L^M$-, if present, is independently —$CH_2$—.

In one embodiment, each —$R^{M6}$, if present, is independently pyrrolidinyl, imidazolidinyl, pyrazolidinyl, piperidinyl, piperizinyl, morpholinyl, azepinyl, diazepinyl, tetrahydrofuranyl, tetrahydropyranyl, or dioxanyl, and is optionally substituted.

In one embodiment, each —$R^{M7}$, if present, is independently phenyl, and is optionally substituted.

In one embodiment, each —$R^{M8}$, if present, is independently $C_{5-6}$heteroaryl, and is optionally substituted.

In one embodiment, each —$R^{M8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{M8}$, if present, is independently $C_5$heteroaryl, and is optionally substituted.

In one embodiment, each —$R^{M8}$, if present, is independently furanyl, thienyl, pyrrolyl, imidazolyl, pyrazolyl, triazolyl, oxazolyl, isoxazolyl, thiazolyl, or isothiazolyl, and is optionally substituted.

In one embodiment, each —$R^{M9}$, if present, is independently:
—F, —Cl, —Br, —I,
—$R^{N1}$,
—$CF_3$,
—OH,
—$OR^{N1}$,
—$OCF_3$,
—$NH_2$, —$NHR^{N1}$, —$NR^{N1}{}_2$, —$NR^{N2}R^{N3}$,
—C(=O)OH,
—C(=O)$OR^{N1}$,
—C(=O)$NH_2$, —C(=O)$NHR^{N1}$, —C(=O)$NR^{N1}{}_2$, —C(=O)$NR^{N2}R^{N3}$,
-$L^N$-OH, -$L^N$-$OR^{N1}$,
$L^N$-$NR^{N1}{}_2$, or -$L^N$-$NR^{N2}R^{N3}$.

In one embodiment, each -$L^N$-, if present, is independently saturated aliphatic $C_{1-3}$alkylene.

In one embodiment, each —$R^{N1}$, if present, is independently $C_{1-4}$alkyl.

In one embodiment, each —$NR^{N2}R^{N3}$, if present, is independently pyrrolidino, imidazolidino, pyrazolidino, piperidino, piperizino, morpholino, azepino, or diazepino, and is optionally substituted, for example, with one or more groups selected from $C_{1-3}$alkyl and —$CF_3$.

In one embodiment, each —$NR^{N2}R^{N3}$, if present, is independently pyrrolidino, piperidino, piperizino, or morpholino, and is optionally substituted, for example, with one or more groups selected from $C_{1-3}$alkyl and —$CF_3$.

In one embodiment, each —$R^{M9}$, if present, is independently —F, —Cl, —Br, —I, -Me, -Et, —$CF_3$, —OH, —OMe, —OEt, —$OCF_3$, —$NH_2$, —NHMe, or —$NMe_2$.

Molecular Weight

In one embodiment, the TC compound has a molecular weight of from 184 to 1200.

In one embodiment, the bottom of range is from 190, 200, 225, 250, 275, 300, or 350.

In one embodiment, the top of range is 1100, 1000, 900, 800, 700, or 600.

In one embodiment, the range is 190 to 600.

Combinations

Each and every compatible combination of the embodiments described above is explicitly disclosed herein, as if each and every combination was individually and explicitly recited.

EXAMPLES OF SPECIFIC EMBODIMENTS

In one embodiment, the compounds are selected from compounds of the following formulae and pharmaceutically acceptable salts and solvates thereof:

| Compound No. | Structure |
|---|---|
| 4-1 | 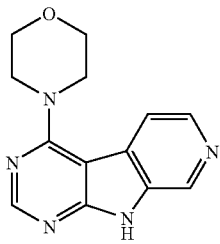 [SMILES: c1cc2c(cn1)[nH]c1ncnc(N3CCOCC3)c12] |
| 4-2 | 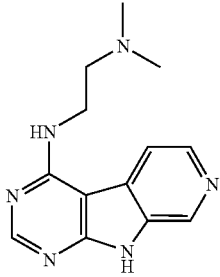 [SMILES: CN(C)CCNc1ncnc2[nH]c3cnccc3c12] |
| 4-3 | 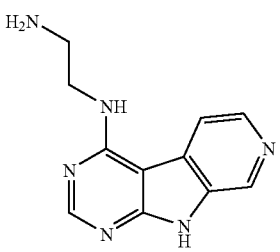 [SMILES: NCCNc1ncnc2[nH]c3cnccc3c12] |
| 4-4 | 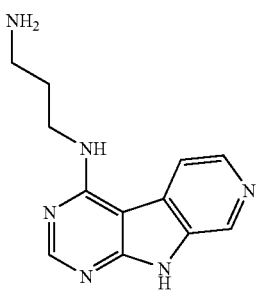 [SMILES: NCCCNc1ncnc2[nH]c3cnccc3c12] |
| 4-5 | 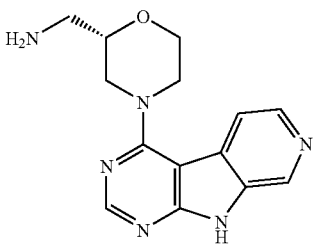 [SMILES: NC[C@H]1CN(c2ncnc3[nH]c4cnccc4c23)CCO1] |
| 4-6 | 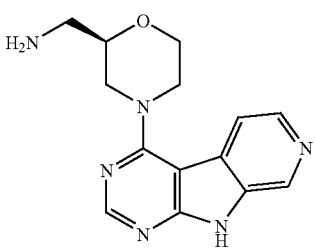 [SMILES: NC[C@@H]1CN(c2ncnc3[nH]c4cnccc4c23)CCO1] |
-continued
| Compound No. | Structure |
|---|---|
| 4-7 | 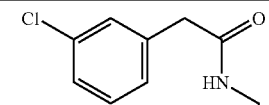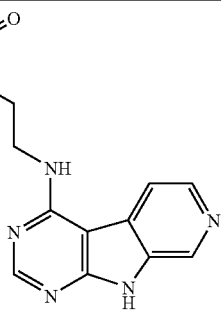 |
| 4-8 | 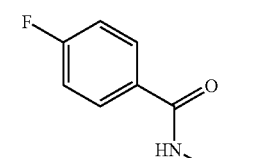 |
| 4-9 | 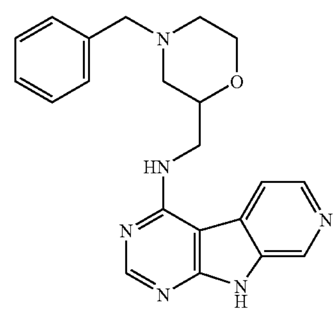 [SMILES: c1ccc(CN2CCOC(CNc3ncnc4[nH]c5cnccc5c34)C2)cc1] |
| 4-10 | 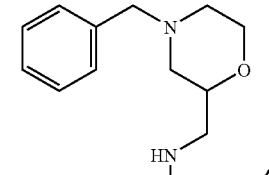 |
| 4-11 | 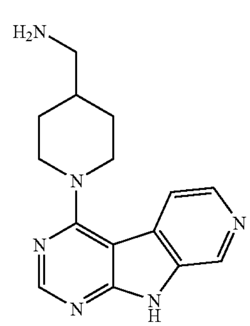 [SMILES: NCC1CCN(c2ncnc3[nH]c4cnccc4c23)CC1] |

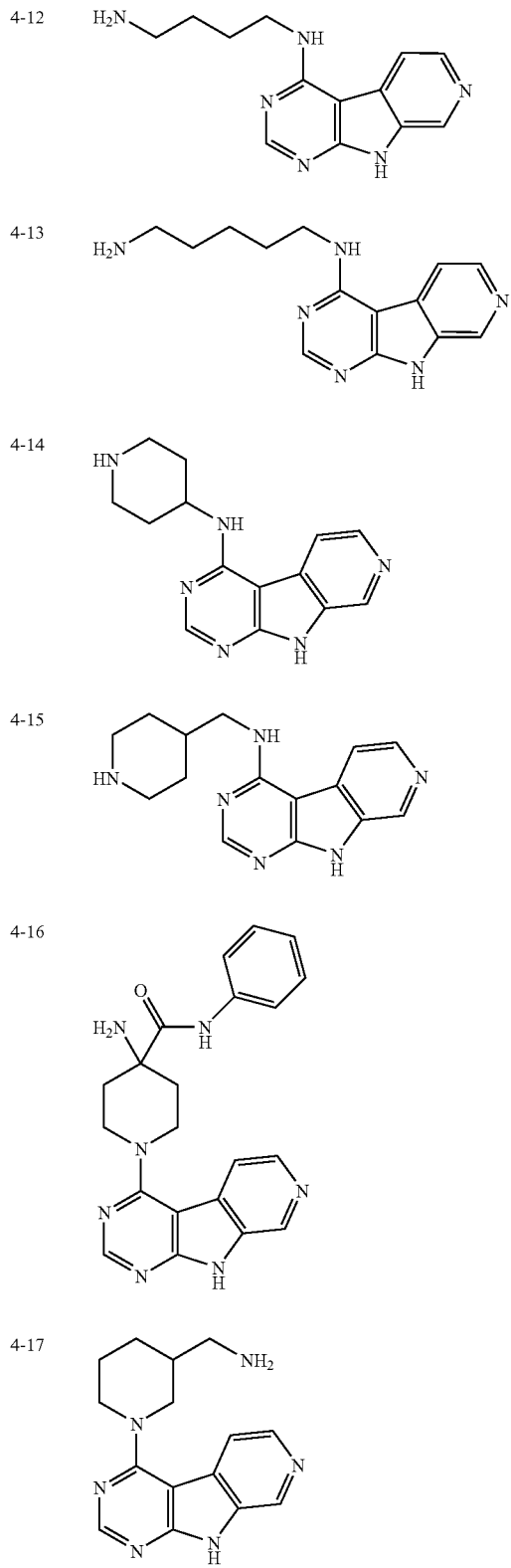
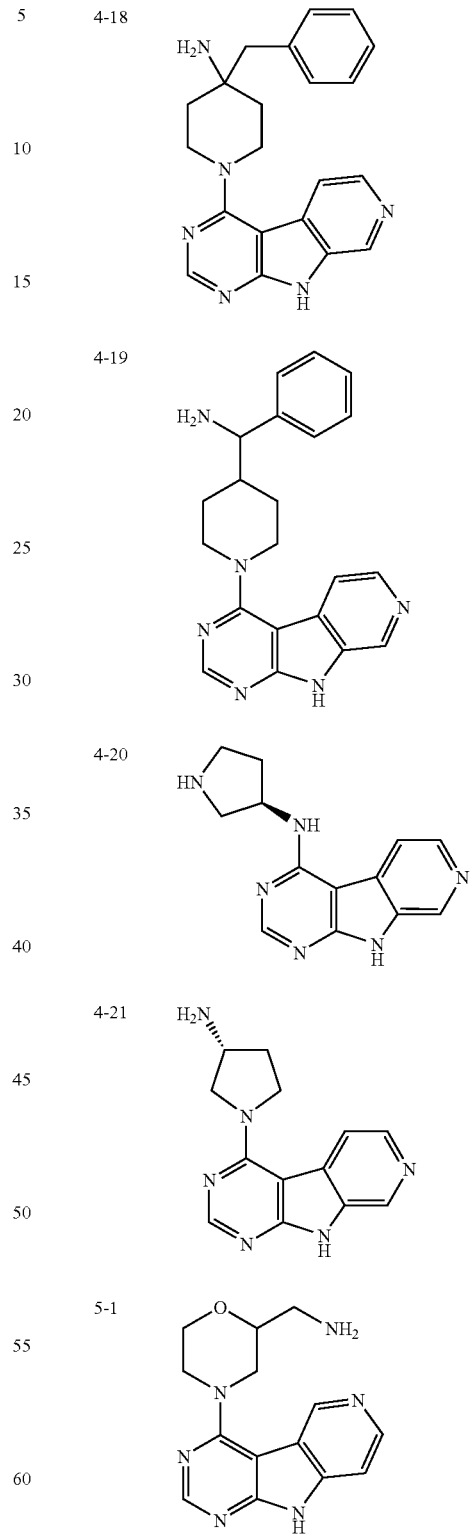
In one embodiment, the compounds are selected from compounds of the following formulae and pharmaceutically acceptable salts and solvates thereof:

| Compound No. | Structure |
|---|---|
| 2-1 | 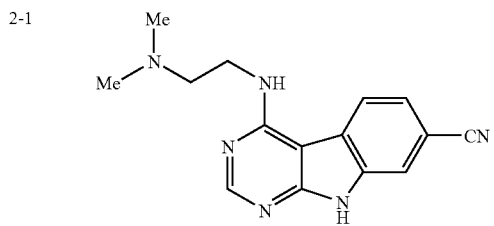 |
| 2-2 | 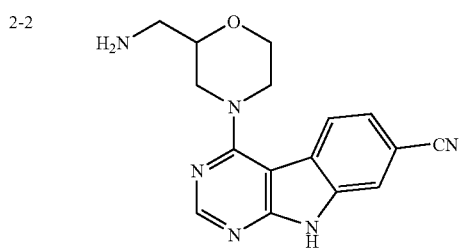 |
| 2-3 | 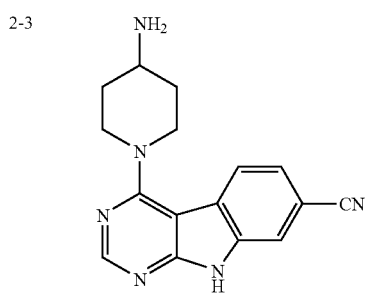 |
| 2-4 | 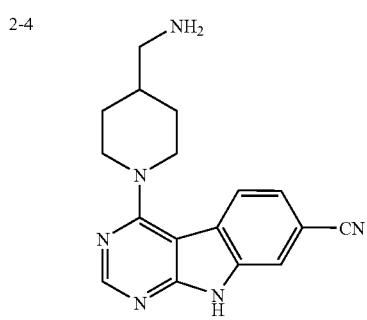 |
| 2-5 | 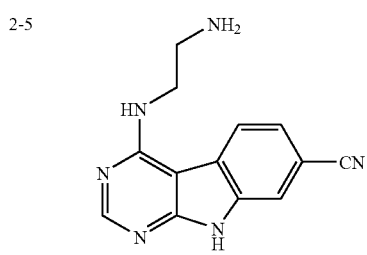 |

-continued

| Compound No. | Structure |
|---|---|
| 2-6 | 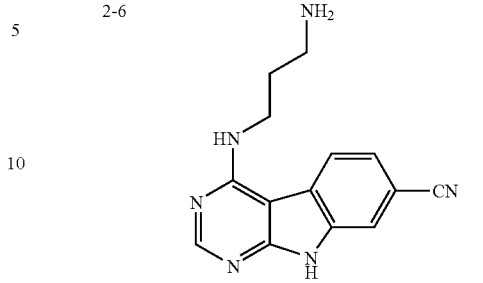 |
| 3-1 | 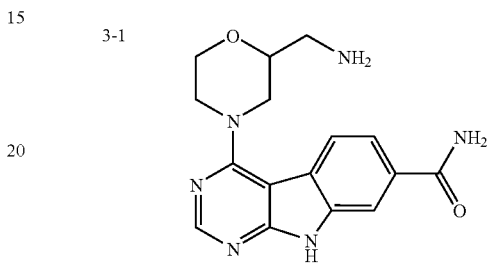 |
| 6-1 | 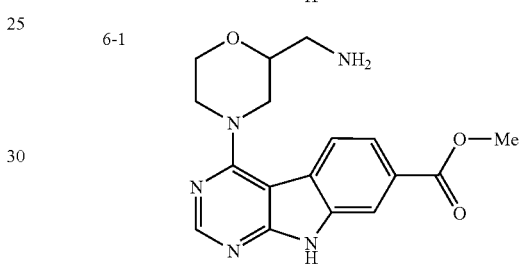 |

In one embodiment, the compounds are selected from compounds of the following formulae and pharmaceutically acceptable salts and solvates thereof:

| Compound No. | Structure |
|---|---|
| 1-1 | 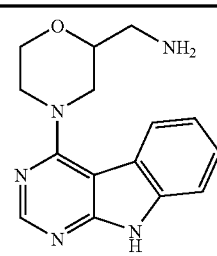 |

Substantially Purified Forms

One aspect of the present invention pertains to TC compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

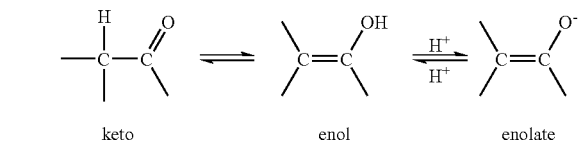

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^−$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of TC compounds of the present invention are described herein. These and/or other well known methods may be modified and/or adapted in known ways in order to facilitate the synthesis of additional compounds within the scope of the present invention.

In one approach (General Method A), compounds of type (iii) are prepared by a method as illustrated in the following scheme. Commercially available compound (i) is treated with phosphorous oxychloride, typically with heating, to give the corresponding chloro derivative, compound (ii). The chloride is then displaced with a suitable amine, for example, in the presence of a tertiary base such as triethylamine at elevated temperatures in NMP using oil bath or microwave heating, to give the corresponding compound (iii). If necessary, any protecting groups that might be present on the amine component may then be removed.

Scheme 1

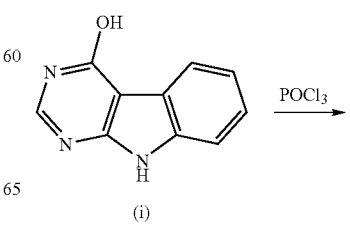

(i)

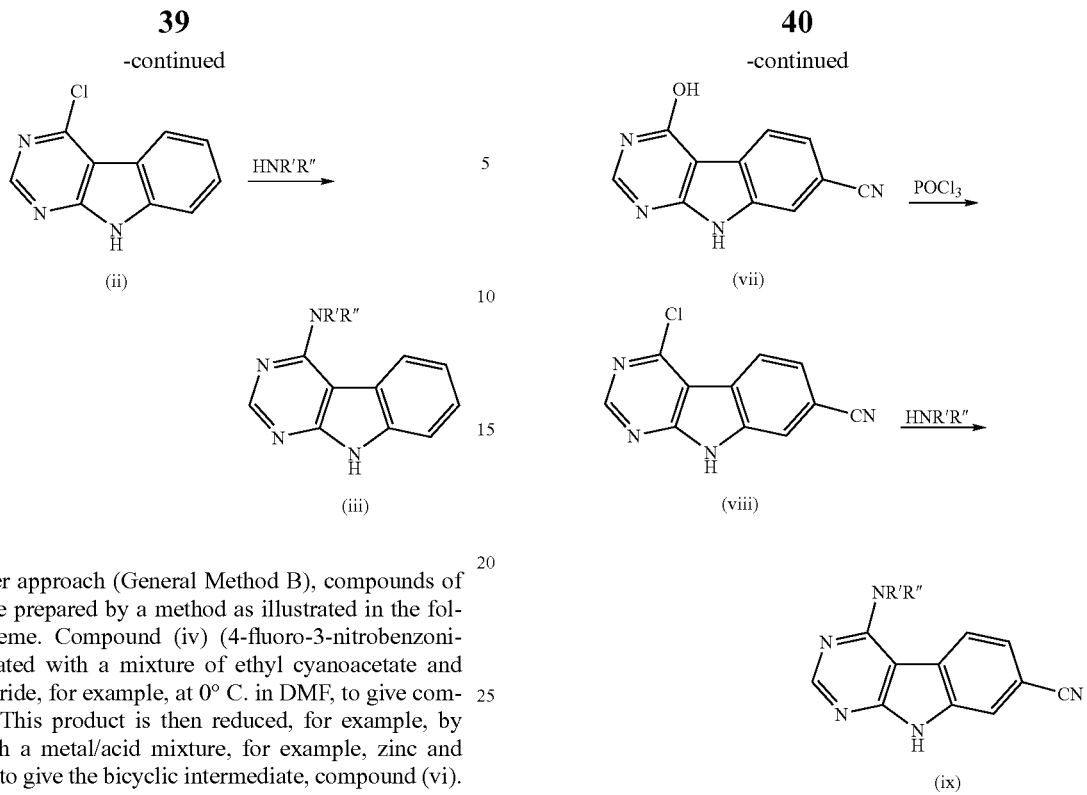

In another approach (General Method B), compounds of type (ix) are prepared by a method as illustrated in the following scheme. Compound (iv) (4-fluoro-3-nitrobenzonitrile) is treated with a mixture of ethyl cyanoacetate and sodium hydride, for example, at 0° C. in DMF, to give compound (v). This product is then reduced, for example, by heating with a metal/acid mixture, for example, zinc and acetic acid, to give the bicyclic intermediate, compound (vi). Treatment of this bicyclic intermediate with formamide and ammonium formate, for example, at elevated temperature, gives the tricyclic hydroxyl derivative, compound (vii), which is then treated with phosphorous oxychloride, for example, with heating, to give the chloro derivative, compound (viii). The chloride is then displaced with a suitable amine, for example, in the presence of a tertiary base such as ethyldiisopropylamine at elevated temperatures in NMP using oil bath or microwave heating, to give the corresponding compound (ix). If necessary, any protecting groups that might be present on the amine component may then be removed.

In another approach (General Method C), compounds of type (xvii) are prepared by a method as illustrated in the following scheme. Compound (x) (4-fluoro-3-nitrobenzoic acid) is esterified in acidic methanol and then treated with a mixture of ethyl cyanoacetate and sodium hydride, for example, at 0° C. in DMF, to give compound (xi). This compound is then reduced, for example, by heating with a metal/acid mixture, for example, zinc and acetic acid, to give the bicyclic intermediate, compound (xii). Treatment of this bicyclic intermediate with formamide and ammonium formate, for example, at elevated temperature, gives the tricyclic hydroxyl derivative, compound (xiii), which is then treated with phosphorous oxychloride, for example, with heating, to give the chloro derivative, compound (xiv). The chloride is then displaced with a suitable amine, for example, in the presence of a tertiary base such as triethylamine at elevated temperatures in NMP using oil bath or microwave heating, to give compound (xv). The ester is then hydrolysed to give the corresponding acid, compound (xvi), for example, using a base such as sodium hydroxide. The acid is then treated with a suitable amide coupling agent, for example, carbonyldiimidazole in the presence of ammonia, to give the corresponding primary amide, compound (xvii). If necessary, any protecting groups that might be present on the amine component may then be removed.

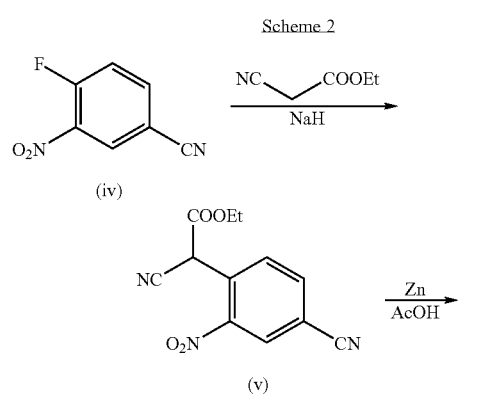

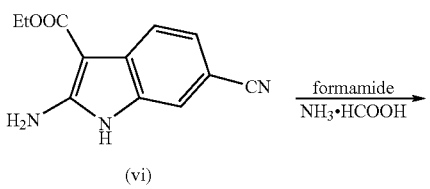

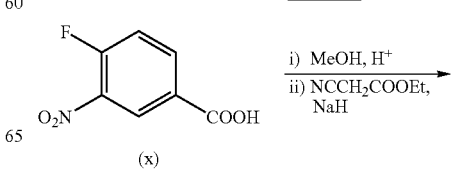

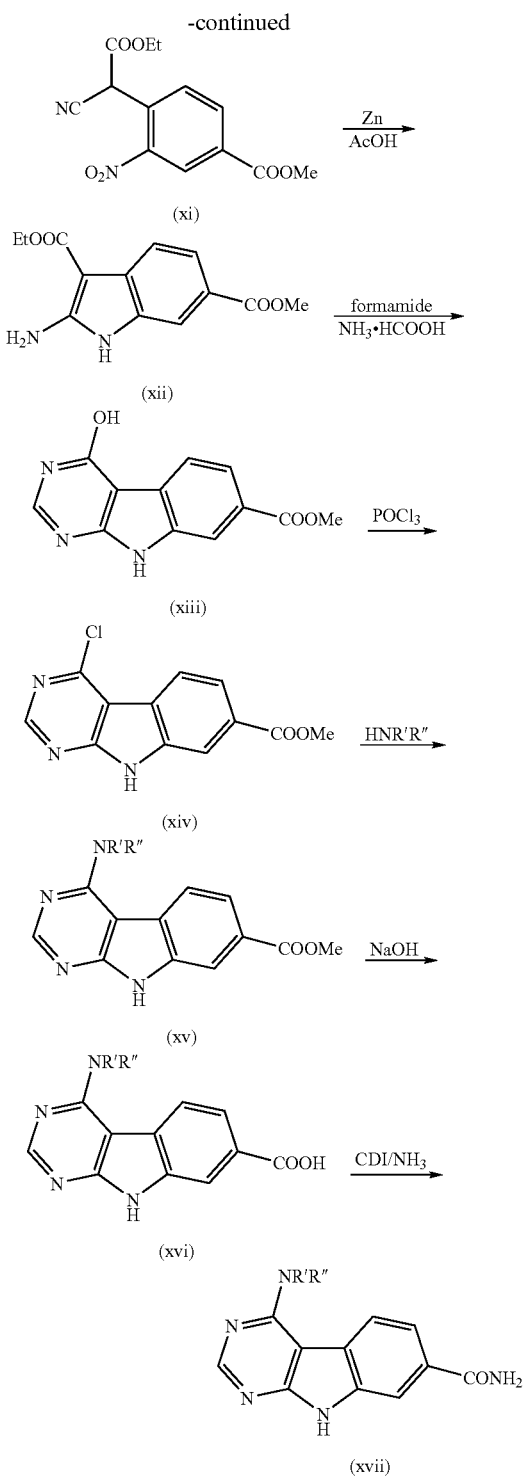

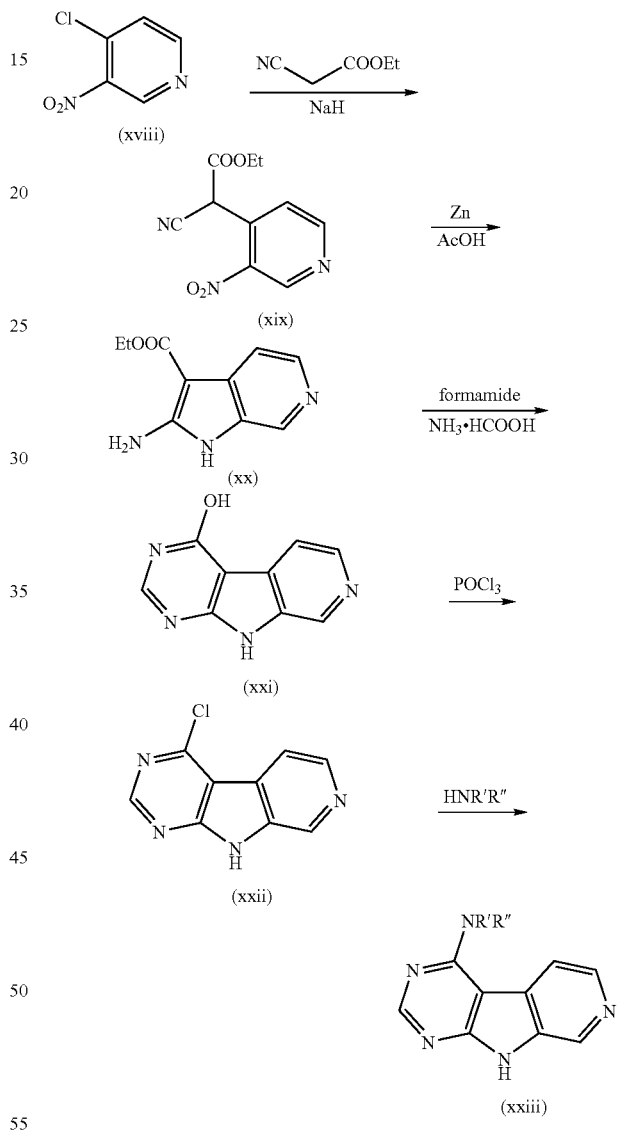

cyclic hydroxyl derivative, compound (xxi), which is then treated with phosphorous oxychloride, for example, with heating, to give the chloro derivative, compound (xx). The chloride is then displaced with a suitable amine, for example, in the presence of a tertiary base such as ethyldiisopropylamine at elevated temperatures in NMP using oil bath or microwave heating, to give the corresponding compound (xxiii). If necessary, any protecting groups that might be present on the amine component may then be removed.

In another approach (General Method D), compounds of type (xxiii) are prepared by a method as illustrated in the following scheme. Compound (xviii) (3-nitro-4-chloropyridine) is treated with a mixture of ethyl cyanoacetate and sodium hydride, for example, at 0° C. in DMF, to give compound (xix). This is then reduced, for example, by heating with a metal/acid mixture, for example, zinc and acetic acid, to give the bicyclic intermediate, compound (a). Treatment of this bicyclic intermediate with formamide and ammonium formate, for example, at elevated temperature, gives the tri- In another approach (General Method E), compounds of type (xxix) are prepared by a method as illustrated in the following scheme. Compound (xxiv) (3-bromo-4-nitropyridine N-oxide) is treated with a mixture of ethyl cyanoacetate and sodium hydride, for example, at 0° C. in THF, to give compound (xxv). This is then reduced, for example, by heating with a metal/acid mixture, for example, iron and acetic acid, to give the bicyclic intermediate, compound (xxvi). Treatment of this bicyclic intermediate with formamide and ammonium formate, for example, at elevated temperature, gives the tricyclic hydroxyl derivative, compound (xxvii), which is then treated with phosphorous oxychloride, for example, with heating, to give the chloro derivative, compound (xxviii). The chloride is then displaced with a suitable amine, for example, in the presence of a tertiary base such as ethyldiisopropylamine at elevated temperatures in NMP using oil bath or microwave heating, to give the corresponding compound (xxix). If necessary, any protecting groups that might be present on the amine component may then be removed.

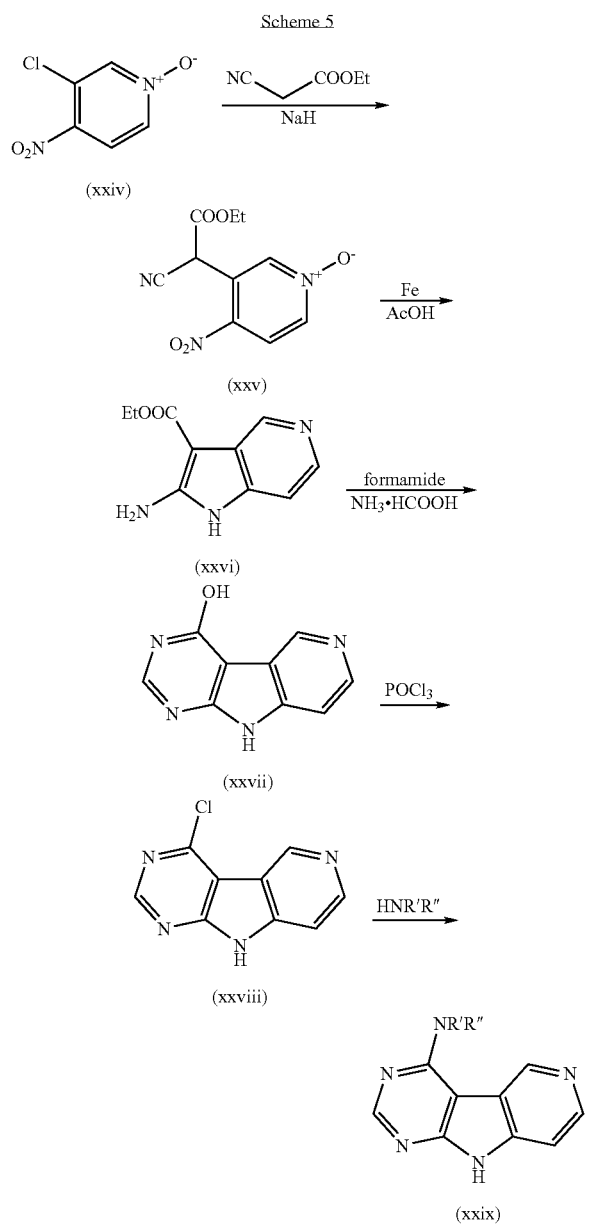

Compositions

One aspect of the present invention pertains to a composition (e.g., a pharmaceutical composition) comprising a TC compound, as described herein, and a pharmaceutically acceptable carrier, diluent, or excipient.

Another aspect of the present invention pertains to a method of preparing a composition (e.g., a pharmaceutical composition) comprising admixing a TC compound, as described herein, and a pharmaceutically acceptable carrier, diluent, or excipient.

Uses

The compounds described herein are useful, for example, in the treatment of diseases and conditions that are ameliorated by the inhibition of CHK1 kinase function, such as, for example, proliferative conditions, cancer, etc.

Use in Methods of Inhibiting CHK1

One aspect of the present invention pertains to a method of inhibiting CHK1 kinase function, in vitro or in vivo, comprising contacting a CHK1 kinase with an effective amount of a TC compound, as described herein.

One aspect of the present invention pertains to a method of inhibiting CHK1 kinase function in a cell, in vitro or in vivo, comprising contacting the cell with an effective amount of a TC compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Suitable assays for determining CHK1 kinase function inhibition are described herein and/or are known in the art.

Use in Methods of Inhibiting Cell Proliferation, Etc.

The TC compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a TC compound, as described herein.

In one embodiment, the method is a method of regulating (e.g., inhibiting) cell proliferation (e.g., proliferation of a cell), in vitro or in vivo, comprising contacting a cell with an effective amount of a TC compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the method is performed in vitro.
In one embodiment, the method is performed in vivo.
In one embodiment, the TC compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a TC compound, as described herein, for use in a method of treatment of the human or animal body by therapy.

In one embodiment, the method of treatment comprises treatment with both (i) a TC compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to (a) a DNA topoisomerase I or II inhibitor, (b) a DNA damaging agent, (c) an antimetabolite or TS inhibitor, or (d) a microtubule targeted agent, as described herein, for use in a method of treatment of the human or animal body by therapy, wherein the method of treatment comprises treatment with both (i) a TC compound, as described herein, and (a) the DNA topoisomerase I or II inhibitor, (b) the DNA damaging agent, (c) the antimetabolite or TS inhibitor, or (d) the microtubule targeted agent.

Use in the Manufacture of Medicaments

Another aspect of the present invention pertains to use of a TC compound, as described herein, in the manufacture of a medicament for use in treatment.

In one embodiment, the medicament comprises the TC compound.

In one embodiment, the treatment comprises treatment with both (i) a medicament comprising a TC compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of (a) a DNA topoisomerase I or II inhibitor, (b) a DNA damaging agent, (c) an antimetabolite or TS inhibitor, or (d) a microtubule targeted agent, as described herein, in the manufacture of a medicament for use in a treatment, wherein the treatment comprises treatment with both (i) a TC compound, as described herein, and (a) the DNA topoisomerase I or II inhibitor, (b) the DNA damaging agent, (c) the antimetabolite or TS inhibitor, or (d) the microtubule targeted agent.

Methods of Treatment

Another aspect of the present invention pertains to a method of treatment comprising administering to a patient in need of treatment a therapeutically effective amount of a TC compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Conditions Treated—Conditions Mediated by CHK1

In one embodiment (e.g., of use in methods of therapy, of use in the manufacture of medicaments, of methods of treatment), the treatment is treatment of a disease or condition that is mediated by CHK1.

Conditions Treated—Conditions Ameliorated by the Inhibition of CHK1 Kinase Function In one embodiment (e.g., of use in methods of therapy, of use in the manufacture of medicaments, of methods of treatment), the treatment is treatment of: a disease or condition that is ameliorated by the inhibition of CHK1 kinase function.

Conditions Treated—Proliferative Conditions and Cancer

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: p53 negative cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:

a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);

a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;

a hematopoietic tumor of myeloid lineage, for example acute and chronic myelogenous leukemias, myelodysplastic syndrome, or promyelocytic leukemia;

a tumour of mesenchymal origin, for example fibrosarcoma or habdomyosarcoma;

a tumor of the central or peripheral nervous system, for example astrocytoma, neuroblastoma, glioma or schwannoma;

melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of: lung cancer, breast cancer, ovarian cancer, colorectal cancer, melanoma, or glioma.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously.

For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Combination Therapies Employing DNA Damaging Agents

As discussed herein, in some embodiments, the TC compound is employed in combination with (e.g., in conjunction with) with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

When both a TC compound and one or more other agents are employed, they may be used (e.g., contacted, administered, etc.) in any order. Furthermore, they may be used (e.g., contacted, administered, etc.) together, as part of a single formulation, or separately, as separate formulations.

For example, in regard to methods of treatment employing both a TC compound and one or more other agents, treatment with (e.g., administration of) the TC compound may be prior to, concurrent with, or may follow, treatment with (e.g., administration of) the one or more other agents, or a combination thereof.

In one embodiment, treatment with (e.g., administration of) a TC compound is concurrent with, or follows, treatment with (e.g., administration of) the one or more other agents.

In one embodiment, the one or more other agents is a DNA topoisomerase I or II inhibitor; for example, Etoposide, Toptecan, Camptothecin, Irinotecan, SN-38, Doxorubicin, Daunorubicin.

In one embodiment, the one or more other agents is a DNA damaging agent; for example, alkylating agents, platinating agents, or compounds that generate free radicals; for example, Temozolomide, Cisplatin, Carboplatin, Mitomycin C, Cyclophosphamide, BCNU, CCNU, Bleomycin.

In one embodiment, the one or more other agents is an antimetabolite or TS inhibitor; for example, 5-fluorouracil, hydroxyurea, Gemcitabine, Arabinosylcytosine, Fludarabine, Tomudex, ZD9331.

In one embodiment, the one or more other agents is a microtubule targeted agent; for example, Paclitaxel, Docetaxel, Vincristine, Vinblastine.

In one embodiment, the one or more other agents is ionising radiation (e.g., as part of radiotherapy).

Other Uses

The TC compounds described herein may also be used as cell culture additives to inhibit CHK1 kinase function, e.g., to inhibit cell proliferation, etc.

The TC compounds described herein may also be used as part of an in vitro assay, for example, in order to determine whether a candidate host is likely to benefit from treatment with the compound in question.

The TC compounds described herein may also be used as a standard, for example, in an assay, in order to identify other compounds, other CHK1 kinase function inhibitors, other anti-proliferative agents, other anti-cancer agents, etc.

Kits

One aspect of the invention pertains to a kit comprising (a) a TC compound as described herein, or a composition comprising a TC compound as described herein, e.g., preferably provided in a suitable container and/or with suitable packaging; and (b) instructions for use, e.g., written instructions on how to administer the compound or composition.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

The written instructions may also include a list of indications for which the active ingredient is a suitable treatment.

Routes of Administration

The TC compound or pharmaceutical composition comprising the TC compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the TC compound to be administered alone, it is preferable to present it as a pharmaceutical formulation (e.g., composition, preparation, medicament) comprising at least one TC compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one TC compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the TC compounds, and compositions comprising the TC compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular TC compound, the route of administration, the time of administration, the rate of excretion of the TC compound, the duration of the treatment, other drugs, compounds, and/or materials used in combination, the severity of the condition, and the species, sex, age, weight, condition, general health, and prior medical history of the patient. The amount of TC compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the TC compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Liquid Chromatography-Mass spectrometry (LC-MS) Methods

LC-MS (1) analyses were performed on a Micromass ZQ mass spectrometer/Waters Alliance 2795 HT HPLC with a Phenomenex Gemini 3 μm, C18, 30 mm×3 mm i.d. column at a temperature of 35° C. and a flow rate of 1.2 mL/minute using the following solvent gradient:
Solvent A: 0.1% Ammonia in acetonitrile.
Solvent B: 0.1% Ammonia, 5% acetonitrile and 0.063% ammonium formate in water.
0.00-2.50 minutes: 5% A/95% B to 95% A/5% B, 1.2 mL/minute
2.50-2.75 minutes: 95% A/5% B, 1.2 mL/minute
2.75-3.65 minutes: 95% A/5% B, 2.0 mL/minute
3.65-4.00 minutes: 95% A/5% B to 5% A/95% B, 2.0 mL/minute
UV detection was at 220-400 nm using a Waters 996 photodiode array UV detector and ionisation was by positive or negative ion electrospray. Molecular weight scan range was 80-1000 amu.

LC-MS (2) analyses were performed on a Micromass ZQ mass spectrometer/Waters Alliance 2795 HT HPLC with a Phenomenex Gemini 5 μm, C18, 30 mm×4.6 mm i.d. column at a temperature of 35° C. and a flow rate of 2 mL/minute using the following solvent gradient:
Solvent A: 0.1% Ammonia in acetonitrile.
Solvent B: 0.1% Ammonia, 5% acetonitrile and 0.063% ammonium formate in water.
0.00-4.25 minutes: 5% A/95% B to 95% A/5% B.
4.25-5.80 minutes: 95% A/5% B.
5.80-5.90 minutes: 95% A/5% B to 5% A/95% B.
5.90-7.00 minutes: 5% A/95% B.

UV detection was at 220-400 nm using a Waters 996 photodiode array UV detector and ionisation was by positive or negative ion electrospray. Molecular weight scan range was 80-1000 amu.

LC-MS (3) analyses were performed on a Micromass LCT/Waters Alliance 2795 HPLC system with a Discovery 5 μm, C18, 50 mm×4.6 mm or 30 mm×4.6 mm i.d. column from Supelco at a temperature of 22° C. and a flow rate of 1 mL/minute using the following solvent gradient:
Solvent A: Methanol.
Solvent B: 0.1% Formic acid in water.
0.0-0.3 minutes: 10% A/90% B.
0.3-0.6 minutes: 10% A/90% B to 20% A/80% B.
0.6-4.5 minutes: 20% A/80% B to 90% A/10% B.
4.5-5.4 minutes: 90% A/10% B.
5.4-5.7 minutes: 90% A/10% B to 10% A/90%.B.
5.7-6.0 minutes: 10% A/90% B.

UV detection was at 254 nm and ionisation was by positive or negative ion electrospray. Molecular weight scan range was 50-1000 amu.

Synthesis 1-1-A

4-Chloro-9H-pyrimido[4,5-b]indole

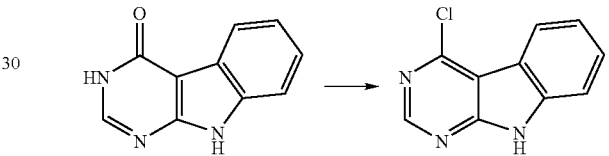

A suspension of 3H-pyrimido[4,5-b]indol-4(9H)-one (0.091 g, 0.491 mmol) in phosphorous oxychloride (8 mL) was refluxed under nitrogen for 24 hours. Phosphorous oxychloride was removed by evaporation and the residue was partitioned between water (20 mL) and chloroform (2×20 mL). The organic extracts were filtered through celite, dried (Na$_2$SO$_4$) and concentrated to give 4-chloro-9H-pyrimido[4,5-b]indole as a yellow solid (0.103 g, 0.50 mmol, quantitative). $^1$H NMR (500 MHz, CDCl$_3$) δ 7.60 (1H, dd, J=8.8 Hz), 7.70 (1H, dd, J=8.8 Hz), 8.43 (1H, d, J=8 Hz), 8.52 (1H, d, J=8 Hz), 8.98 (1H, s); LC-MS (3) R$_t$: 5.59 min; m/z (ESI) 206, 204 [MH$^+$].

Synthesis 1-1-B

[4-(9H-Pyrimido[4,5-b]indol-4-yl)-morpholin-2-ylmethyl]-carbamic acid tert-butyl ester

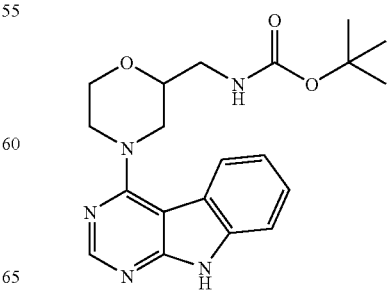

A mixture of 4-chloro-9H-pyrimido[4,5-b]indole (0.045 g, 0.221 mmol), morpholin-2-ylmethyl-carbamic acid tert-butyl ester (0.055 g, 0.25 mmol) and triethylamine (0.10 mL, 0.75 mmol) in DMF (0.70 mL) was heated to 120° C. in a microwave reactor for 1 hour. The cooled solution was partitioned between water (20 mL) and ethyl acetate (20 mL). The organic extract was dried (Na$_2$SO$_4$), filtered and concentrated. Flash column chromatography, eluting with ethyl acetate, gave the title compound as a yellow solid (0.021 g, 0.0548 mmol, 25%). LC-MS (3) R$_t$ 5.57 min; m/z (ESI) 384 [MH$^+$].

Synthesis 1-1-C

C-[4-(9H-Pyrimido[4,5-b]indol-4-yl)-morpholin-2-yl]-methylamine

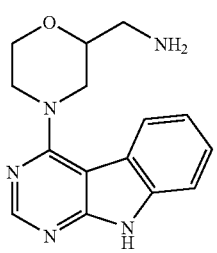

A solution of [4-(9H-pyrimido[4,5-b]indol-4-yl)-morpholin-2-ylmethyl]-carbamic acid tert-butyl ester (0.021 g, 0.548 mmol) and 4M HCl-dioxane (1 mL) in methanol (5 mL) was stirred at room temperature for 2.5 hours. The solution was evaporated to dryness and purified by Ion exchange on SCX-II acidic resin (2 g) eluting with methanol, then 2 M ammonia-methanol. The basic fractions were combined. Preparative silica TLC, eluting with 1% ammonia—9% methanol—90% dichloromethane, gave the title compound (0.007 g, 0.025 mmol, 46%) as a beige powder. $^1$H NMR (500 MHz, CD$_3$OD) δ 2.75-2.80 (2H, m), 3.00-3.06 (1H, m), 3.35-3.40 (1H, m), 3.75-3.85 (1H, m), 3.90 (1H, dd, J=10.10 Hz), 4.10-4.13 (1H, m), 4.19 (1H, d, J=13 Hz), 4.25 (1H, d, J=13 Hz), 7.35 (1H, dd, J=8.8 Hz), 7.47 (1H, dd, J=8.8 Hz), 7.57 (1H, d, J=8 Hz), 7.79 (1H, d, J=8 Hz), 8.46 (1H, s); LC-MS (3) R$_t$ 1.98 min; m/z (ESI) 284 [MH$^+$].

In a manner similar to the one described in Synthesis 1-1, the following compounds were synthesised.

| Synthesis | Structure | (M + H)$^+$ |
|---|---|---|
| 1-2 | 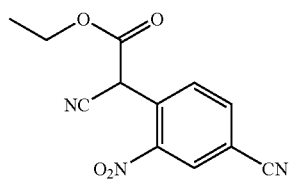 | 284 |
| 1-3 | 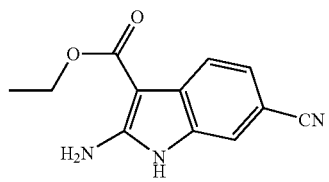 [SMILES: CCOC(=O)c1c(N)[nH]c2cc(C#N)ccc12] | 284 |

Synthesis 2-1-A

Cyano-(4-cyano-2-nitro-phenyl)-acetic acid ethyl ester

To a suspension of sodium hydride (0.96 g, 60% in mineral oil, 24 mmol) in DMF (6 mL) at 0° C. was added ethylcyanoacetate (2.72 g, 24 mmol) in DMF (2 mL) under an atmosphere of nitrogen. The reaction mixture was stirred at room temperature for 30 minutes then 4-fluoro-3-nitro-benzonitrile (2.05 g, 22.7 mmol) in DMF (5 mL) was added dropwise. 1M HCl and ethyl acetate were added to the reaction mixture after 1 hour. The organic layer was washed with water and brine, then dried over sodium sulphate and concentrated to give a brown oil which was purified by flash column chromatography to give the title compound. $^1$H NMR (DMSO-d$_6$) δ 8.79 (1H), 8.38 (1H), 7.95 (1H, d, J=2), 6.38 (1H), 4.21 (2H), 1.19 (3H, t).

Synthesis 2-1-B

2-Amino-6-cyano-1H-indole-3-carboxylic acid ethyl ester

Zinc powder (2.40 g) was added portionwise to a solution of Cyano-(4-cyano-2-nitro-phenyl)-acetic acid ethyl ester (1.15 g, 4.4 mmol) in 10 mL acetic acid at 80° C. The mixture was then heated at 95° C. for 30 minutes. The reaction was then cooled to room temperature, filtered and the catalyst rinsed with acetic acid. The filtrate was concentrated to near dryness then neutralised with saturated sodium bicarbonate solution. The product was then isolated by filtration and washing with ethyl acetate to give the title compound as a tan solid (700 mg, 69%). $^1$H NMR (DMSO) δ 11.07 (1H, s), 7.62 (1H, d, J=8.1), 7.49 (1H, d, J=1.1), 7.33 (1H, dd, J=8.1, 1.5), 7.10 (2H, br, s), 4.24 (2H, q, J=7.3), 1.32 (3H, t, J=7.1); LC-MS (1) $R_t$ 1.84 min; m/z 228 (ES−).

Synthesis 2-1-C

4-Hydroxy-9H-pyrimido[4,5-b]indole-7-carbonitrile

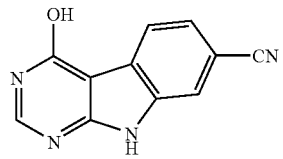 [SMILES: N#Cc1ccc2c(c1)[nH]c1ncnc(O)c12]

A solution of 2-amino-6-cyano-1H-indole-3-carboxylic acid ethyl ester (750 mg, 3.3 mmol) and ammonium formate (193 mg, 3.3 mmol) in 4 mL formamide was heated to 175° C. overnight. The reaction mixture was allowed to cool to room temperature then poured onto water. The resulting precipitate was collected by filtration to give 297 mg of the title compound as a black solid. $^1$H NMR (DMSO) δ 12.7 (1H, s, br), 12.5 (1H, s, br), 8.23 (1H, d, J=4), 8.10 (1H, d, J=8.1), 7.93 (1H, s), 7.61 (1H, dd, J=8.1, 1.4); LC-MS (1) $R_t$ 1.12 min; m/z (ES−) 209.

Synthesis 2-1-D

4-Chloro-9H-pyrimido[4,5-b]indole-7-carbonitrile

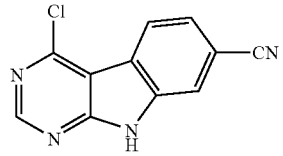 [SMILES: N#Cc1ccc2c(c1)[nH]c1ncnc(Cl)c12]

A solution of 4-hydroxy-9H-pyrimido[4,5-b]indole-7-carbonitrile (215 mg, 1.02 mmol) in 5 mL POCl$_3$ (5 mL) was heated at 100° C. for 18 hours. Upon cooling to room temperature the reaction mixture was evaporated to dryness and the residue treated with saturated sodium bicarbonate solution and ethyl acetate. The organic phase was dried over sodium sulphate and concentrated to the title compound as an orange solid. LC-MS (1) $R_t$ 1.66 min; (100% UV), m/z (ES−) 227/229. The product was used without further purification.

Synthesis 2-1-E 4-(2-Dimethylamino-ethylamino)-9H-pyrimido[4,5-b]indole-7-carbonitrile

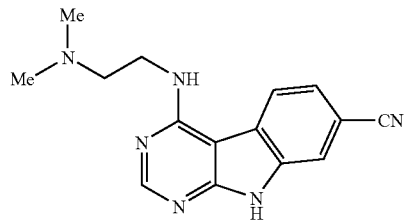 [SMILES: CN(C)CCNc1ncnc2[nH]c3cc(C#N)ccc3c12]

A mixture of 4-chloro-9H-pyrimido[4,5-b]indole-7-carbonitrile (23 mg, 0.10 mmol), 2-dimethylaminoethylamine (27 mg, 0.3 mmol) and N-ethyldiisopropylamine (88 μL, 0.50 mmol) in 1 ml of NMP was heated at 140° C. for 20 minutes using microwave irradiation. The reaction mixture was diluted with 5 mL methanol and applied to a 500 mg MP-TsOH SPE cartridge. After washing the cartridge, the product was eluted using 2 N ammonia in methanol. The eluent was concentrated in vacuo and the residue purified by prep HPLC to give 5.1 mg of the title compound as a white solid. $^1$H NMR (DMSO, δ, ppm) δ 2.3 (6H, s), 2.65 (2H, t, J=6.8 Hz), 3.7-3.8 (2H, m), 7.45 (1H, t, J=6.1 Hz), 7.7 (1H, d, J=8.1 Hz), 7.9 (1H, s), 8.2 (1H, s), 8.4 (1H, s), 8.5 (1H, d, J=8.1 Hz), 12.4 (1H, br s); LC-MS (2) $R_t$ 2.03 min; m/z (ES+) 281.

In a manner similar to the one described in Synthesis 2-1, the following compounds were synthesised.

| Synthesis | Structure | (M + H)⁺ |
|---|---|---|
| 2-2 | ![structure] | 309 |
| 2-3 | ![structure] | 293 |
| 2-4 | ![structure] | 307 |
| 2-5 | ![structure] | 253 |

-continued

| Synthesis | Structure | (M + H)⁺ |
|---|---|---|
| 2-6 | 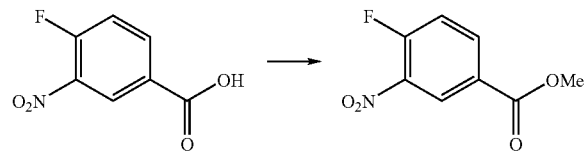 [SMILES: O=C(O)c1ccc(F)c([N+](=O)[O-])c1 ; COC(=O)c1ccc(F)c([N+](=O)[O-])c1] | 267 |

Synthesis 3-1-A

4-Fluoro-3-nitro-benzoic acid methyl ester

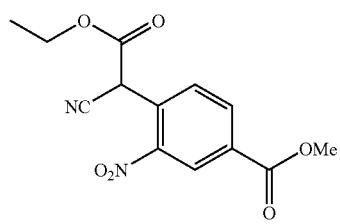

To a solution of 4-fluoro-3-nitro-benzoic acid (5.05 g, 27 mmol) in 50 mL methanol was added 1 mL of 99% sulphuric acid. The mixture was refluxed overnight, allowed to cool and then concentrated in vacuo. The resulting residue was dissolved in ethyl acetate and washed with saturated sodium bicarbonate solution. The organic layer was then dried over sodium sulphate and concentrated in vacuo to give the title product as a white solid (5.15 g, 26 mmol). $^1$H NMR (DMSO) δ 8.50 (1H, d), 8.30-8.27 (1H, m), 7.71 (1H, t), 3.90 (3H, s); LC-MS $R_t$ 1.93 min.

Synthesis 3-1-B 4-(Cyano-ethoxycarbonyl-methyl)-3-nitro-benzoic acid methyl ester

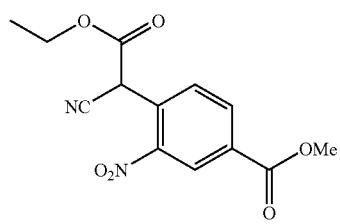

Ethylcyanoacetate (1.14 g, 10.0 mmol, 2 eq) in 1 mL DMF was added at 0° C. to a suspension of sodium hydride (0.4 g, 60% in mineral oil, 5.02 mmol) in 3 mL DMF under an atmosphere of nitrogen. The reaction mixture was stirred at room temperature for 30 minutes before the dropwise addition of 4-fluoro-3-nitro-benzoic acid methyl ester (1.05 g, 22.7 mmol) in 5 mL DMF. After stirring for 2 hours at room temperature, 2 M HCl (20 mL) and ethyl acetate (20 mL) were added to the red solution. The organic layer was washed with water and brine, dried over sodium sulphate and concentrated to give the title compound as an orange oil, which was used without further purification (1.47 g, 5.03 mmol). $^1$H NMR (CDCl$_3$) δ 8.83 (1H, d, J=1.5), 8.38 (1H, dd, J=8.0, 1.8), 7.89 (1H, d, J=8.1), 5.74 (1H, s), 4.30 (2H, q, J=7.1), 4.00 (3H, s), 1.32 (3H, t, J=7.0).

Synthesis 3-1-C

2-Amino-1H-indole-3,6-dicarboxylic acid 3-ethyl ester 6-methyl ester

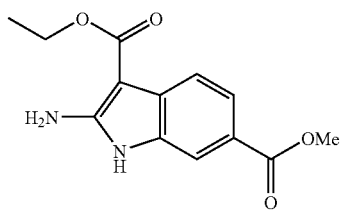 [SMILES: CCOC(=O)c1c(N)[nH]c2cc(C(=O)OC)ccc12]

Zinc powder (4.9 g) was added portion-wise at 80° C. to a solution of 4-(cyano-ethoxycarbonyl-methyl)-3-nitro-benzoic acid methyl ester (4.40 g, 15 mmol) in acetic acid. The mixture was then heated for 3 hours at 95° C. and 3 hours at 100° C. before being allowed to cool to room temperature at which point the reaction mixture was filtered and the insoluble matter rinsed with acetic acid. The filtrate was concentrated to give a brown oil which was subjected to flash silica chromatography using ethyl acetate as eluent. The partially purified oil was taken up into dichloromethane and the product precipitated using hexane to give the title compound as a pale brown solid (1.71 g, 6.5 mmol). LC-MS (1) $R_t$ 1.88 min; m/z 263.

Synthesis 3-1-D

4-Hydroxy-9H-pyrimido[4,5-b]indole-7-carboxylic acid methyl ester

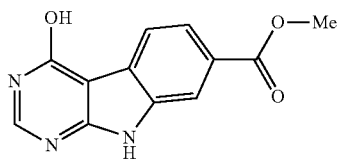 [SMILES: COC(=O)c1ccc2c(c1)[nH]c1ncnc(O)c12]

A suspension of 2-amino-1H-indole-3,6-dicarboxylic acid 3-ethyl ester 6-methyl ester (259 mg, 1 mmol) and ammonium formate (62 mg, 1 mmol) in 2 mL formamide was heated under an atmosphere of nitrogen to 170° C. overnight. On cooling to room temperature, water was added and the resulting precipitate was collected by filtration and dried in a vacuum oven for 4 hours to a constant weight to give the title compound (103 mg, 0.42 mmol). LC-MS (1) $R_t$ 1.27 min; m/z (ES−) 242.

Synthesis 3-1-E

4-Chloro-9H-pyrimido[4,5-b]indole-7-carboxylic acid methyl ester

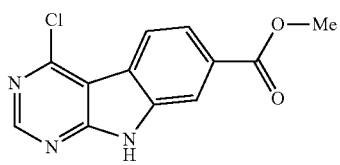 [SMILES: COC(=O)c1ccc2c(c1)[nH]c1ncnc(Cl)c12]

A mixture of 4-hydroxy-9H-pyrimido[4,5-b]indole-7-carboxylic acid methyl ester (215 mg, 0.88 mmol) and POCl₃ (2 mL) was heated at 90° C. for 2 hours. Upon cooling the reaction mixture was concentrated in vacuo to give the title compound and used immediately in the subsequent synthesis. LC-MS (1) R$_t$ 1.79 min; m/z (ES+) 262/264.

Synthesis 3-1-F

4-[2-(tert-Butoxycarbonylamino-methyl)-morpholin-4-yl]-9H-pyrimido[4,5-b]indole-7-carboxylic acid methyl ester

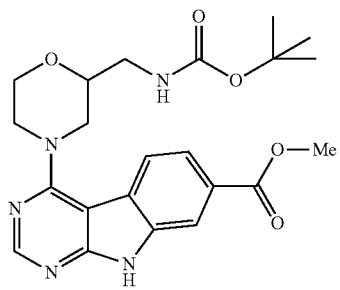 [SMILES: COC(=O)c1ccc2c(c1)[nH]c1ncnc(N3CCOC(CNC(=O)OC(C)(C)C)C3)c12]

A mixture of 4-chloro-9H-pyrimido[4,5-b]indole-7-carboxylic acid methyl ester (231 mg, 0.88 mmol), tert-butyl morpholin-2-yl-methylcarbamate (382 mg, 1.77 mmol), and triethylamine (246 µL, 1.77 mmol) in NMP was irradiated in a microwave at 140° C. for 15 minutes. An additional 246 µL of triethylamine was added to the reaction mixture and the irradiation repeated. The reaction mixture was then added to 5 mL water and the resulting precipitate was collected by filtration and purified by flash chromatography to give the title compound (39 mg, 0.088 mmol). LC-MS (2) R$_t$ 2.67 min; m/z (ES+) 442.

Synthesis 3-1-G

4-[2-(tert-Butoxycarbonylamino-methyl)-morpholin-4-yl]-9H-pyrimido[4,5-b]indole-7-carboxylic acid

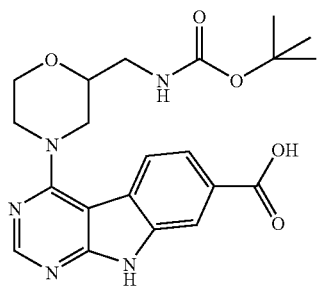 [SMILES: CC(C)(C)OC(=O)NCC1CN(c2ncnc3[nH]c4cc(C(=O)O)ccc4c23)CCO1]

A suspension of 4-[2-(tert-Butoxycarbonylamino-methyl)-morpholin-4-yl]9H-pyrimido[4,5-b]indole-7-carboxylic acid methyl ester (35 mg, 0.079 mmol) in methanol (2 mL) was treated with NaOH (1 mL, 4 M in dioxane, 4 mmol) and left overnight at room temperature. DCM (5 mL) was added to the reaction mixture. The aqueous layer was collected and acidified with 1M HCl, evaporated to dryness and suspended in water. The resulting precipitate was collected by filtration as a white solid (12 mg, 0.028 mmol). LC-MS (1) R$_t$ 1.17 min; m/z (ES−) 426.

Synthesis 3-1-H

[4-(7-Carbamoyl-9H-pyrimido[4,5-b]indol-4-yl)-morpholin-2-ylmethyl]-carbamic acid tert-butyl ester

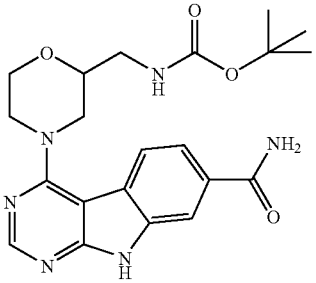 [SMILES: CC(C)(C)OC(=O)NCC1CN(c2ncnc3[nH]c4cc(C(N)=O)ccc4c23)CCO1]

4-[2-(tert-Butoxycarbonylamino-methyl)-morpholin-4-yl]-9H-pyrimido[4,5-b]indole-7-carboxylic acid (6 mg, 0.014 mmol) was stirred in DMF (0.25 mL) at 0° C. Carbonyldiimidazole (2.5 mg, 0.016 mmol) was added and the reaction allowed to proceed to room temperature for 30 minutes. Ammonia (28% aqueous, 0.04 mL) was added. The reaction mixture was concentrated to dryness and then the reaction was repeated to afford a complete conversion. The reaction mixture was concentrated to give the title compound as a yellow solid (5 mg, 0.012 mmol), which was deprotected without further purification. LC-MS (1) R$_t$ 1.48 min; m/z 427 (ES+).

Synthesis 3-1-I 4-(2-Aminomethyl-morpholin-4-yl)-9H-pyrimido[4,5-b]indole-7-carboxylic acid amide

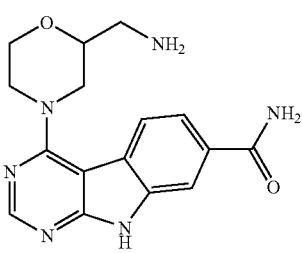 [SMILES: NCC1CN(c2ncnc3[nH]c4cc(C(N)=O)ccc4c23)CCO1]

[4-(7-Carbamoyl-9H-pyrimido[4,5-b]indol-4-yl)-morpholin-2-ylmethyl]-carbamic acid tert-butyl ester (5.5 mg, 0.013 mmol) was suspended in methanol and loaded onto a MP-TsOH SPE cartridge which had been pre-conditioned with methanol. The deprotected product was then eluted off using 2 N ammonia in methanol and concentrated in vacuo to give the title compound as an off-white solid (4 mg, 0.012 mmol). LC-MS (2) R$_t$ 1.08 min; m/z 327 (ES+).

Synthesis 4-1-A

Cyano-(3-nitro-pyridin-4-yl)-acetic acid ethyl ester

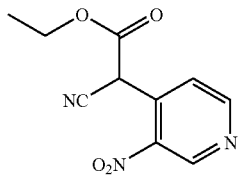

Ethylcyanoacetate (3.75 g, 38 mmol) in 3 mL DMF was added dropwise at 0° C. to a suspension of sodium hydride (1.5 g, 60% in mineral oil, 38 mmol) in DMF (9 mL). The reaction mixture was stirred at room temperature for 30 minutes then cooled to ° C. and 3-nitro-4-chloropyridine (2.63 g, 19 mmol, 1 eq) in DMF (3 mL) added slowly. 2 M HCl (20 mL) and ethyl acetate (20 mL) were added after 2 hours stirring at room temperature and the organic layer was washed with water and brine, before being dried over sodium sulphate and concentrated to give a red/orange oil. The crude oil was triturated with ethyl acetate and the resultant solid collected by filtration to give the title compound (2.88 g, 48%). $^1$H NMR ($d_6$-DMSO) δ 13.2 (s, br), 8.70 (1H, s), 7.88 (1H, dd, J=7.1, 1.0), 4.06 (2H, q, J=7.1), 1.18 (3H, t, J=7.1); LC-MS (1) $R_t$ 1.13 min; m/z (ES−) 190, 234.

Synthesis 4-1-B

2-Amino-1H-pyrrolo[2,3-c]pyridine-3-carboxylic acid ethyl ester

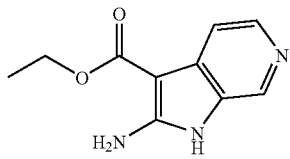

A solution of cyano-(3-nitro-pyridin-4-yl)-acetic acid ethyl ester (2.50 g, 10.6 mmol) in 20 mL acetic acid was heated to 80° C. under nitrogen. Zinc powder was added in 500 mg portions over 20 minutes and the reaction mixture was then heated to 95° C. and stirred for 1 hour. Upon cooling, the insoluble material was removed by filtration and washed with acetic acid. The resulting filtrate was concentrated in vacuo and the residue treated with saturated sodium bicarbonate solution to give a light brown solid which was collected by filtration and dried in vacuo to a constant weight to give the title compound (2.02 g, 93%). $^1$H NMR (DMSO) δ 11.0 (1H, s, br), 8.31 (1H, br), 8.0 (1H, br), 7.41 (1H, d, J=4.7), 7.0 (2H, br s), 4.23 (2H, q, J=7.1), 1.32 (3H, t, J=7.1).

Synthesis 4-1-C

9H-Pyrido[4',3':4,5]pyrrolo[2,3-d]pyrimidin-4-ol

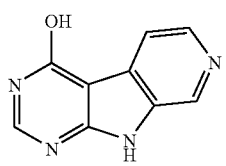 [SMILES: Oc1ncnc2[nH]c3cnccc3c12]

A mixture of 2-Amino-1H-pyrrolo[2,3-c]pyridine-3-carboxylic acid ethyl ester (1.80 g, 8.8 mmol) and ammonium formate (0.62 g, 9.8 mmol) in formamide (10 mL) was heated at 170° C. for 18 hours. 1 M HCl was added to the cooled reaction mixture and the resulting suspension was filtered to remove insolubles. The filtrate was then adjusted to pH 7 with saturated sodium bicarbonate solution. The resulting precipitate was collected by filtration and dried to a constant weight in a vacuum oven to give the title compound (0.74 g, 4.0 mmol). $^1$H NMR (DMSO) δ 12.5 (s, br), 8.83 (1H, s), 8.37 (1H, d, J=4.0), 8.26 (1H, s), 7.89 (1H, d, J=4.0); LC-MS (1) $R_t$ 0.75 min; m/z 185 (ES−).

Synthesis 4-1-D

4-Chloro-9H-pyrido[4',3':4,5]pyrrolo[2,3-d]pyrimidine

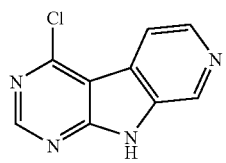

A mixture of 9H-pyrido[4',3':4,5]pyrrolo[2,3-d]pyrimidin-4-ol (264 mg, 1.4 mmol) and triethylamine (750 μL) in 5 mL POCl$_3$ was heated at 75° C. for 18 hours. Toluene was added to the cooled reaction mixture and the solvents were then removed in vacuo to give the title compound as a brown oil (290 mg). LC-MS (1) $R_t$ 1.25 min; m/z (ES+) 205/207.

Synthesis 4-1-E

4-Morpholin-4-yl-9H-pyrido[4',3':4,5]pyrrolo[2,3-d]pyrimidine

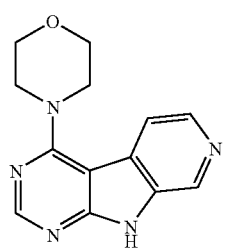 [SMILES: c1cc2c(cn1)[nH]c1ncnc(N3CCOCC3)c12]

A mixture of 4-chloro-9H-pyrido[4',3':4,5]pyrrolo[2,3-d]pyrimidine (18 mg, 0.09 mmol), morpholine (23 μL, 0.26 mmol) and triethylamine (62 μL, 0.44 mmol) in 1 mL of NMP was irradiated in a microwave reactor at 150° C. for 20 minutes. The reaction mixture was evaporated to dryness and the residue purified by prep HPLC to give 7.6 mg of a white solid. $^1$H NMR (DMSO, 6, ppm) δ 3.65-3.75 (8H, m), 7.70 (1H, d, J=5.5 Hz), 8.45 (1H, d, J=5.5 Hz), 8.55 (1H, s), 8.85 (1H, s), 12.50 (1H, br s); LC-MS (2) $R_t$ 1.46 min; m/z (ES+) 256.

In a manner similar to the one described in Synthesis 4-1, the following compounds were synthesised.

| Synthesis | Structure | (M + H)⁺ |
|---|---|---|
| 4-2 | 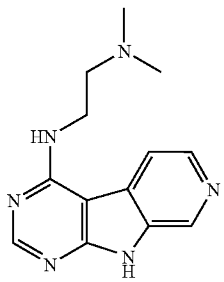 [SMILES: CN(C)CCNc1ncnc2[nH]c3cnccc3c12] | 257 |
| 4-3 | 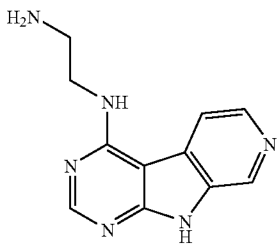 [SMILES: NCCNc1ncnc2[nH]c3cnccc3c12] | 229 |
| 4-4 | 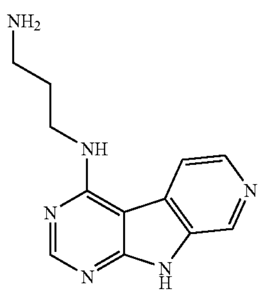 [SMILES: NCCCNc1ncnc2[nH]c3cnccc3c12] | 243 |
| 4-5 | 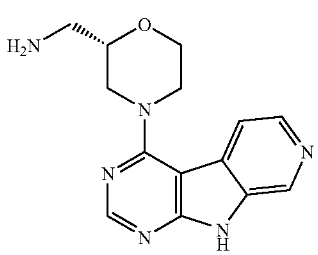 [SMILES: NC[C@H]1CN(c2ncnc3[nH]c4cnccc4c23)CCO1] | 285 |
| 4-6 | 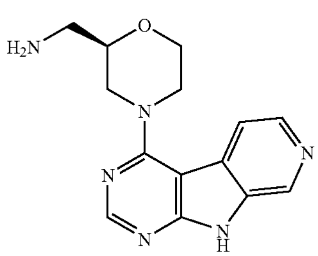 [SMILES: NC[C@@H]1CN(c2ncnc3[nH]c4cnccc4c23)CCO1] | 285 |

-continued

| Synthesis | Structure | (M + H)+ |
|---|---|---|
| 4-7 | (3-chlorophenyl)acetamide linked via -NH-CH2CH2-NH- to pyrimido-pyrrolo-pyridine | 382 |
| 4-8 | 4-fluorobenzamide linked via -NH-CH2CH2-NH- to pyrimido-pyrrolo-pyridine | 351 |
| 4-9 | 4-benzylmorpholin-2-yl-methylamino linked to pyrimido-pyrrolo-pyridine | 375 |
| 4-10 | 4-aminopiperidin-1-yl linked to pyrimido-pyrrolo-pyridine | 269 |
| 4-11 | 4-(aminomethyl)piperidin-1-yl linked to pyrimido-pyrrolo-pyridine | 283 |

-continued
| Synthesis | Structure | (M + H)⁺ |
|---|---|---|
| 4-12 | 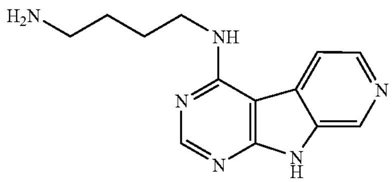 [SMILES: NCCCCNc1ncnc2[nH]c3cnccc3c12] | 257 |
| 4-13 | 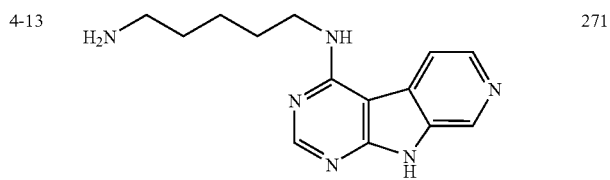 | 271 |
| 4-14 | 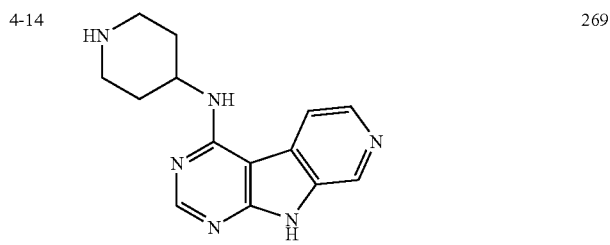 | 269 |
| 4-15 | 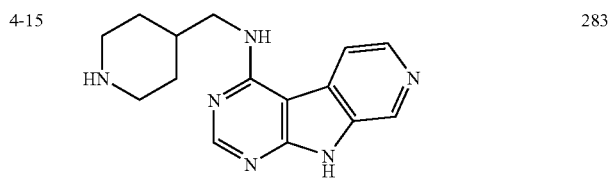 | 283 |
| 4-16 | 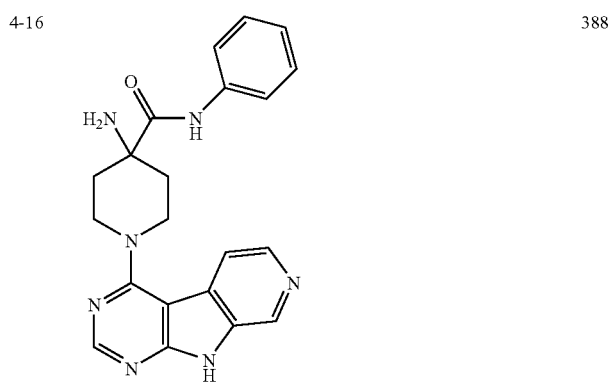 | 388 |
| 4-17 | 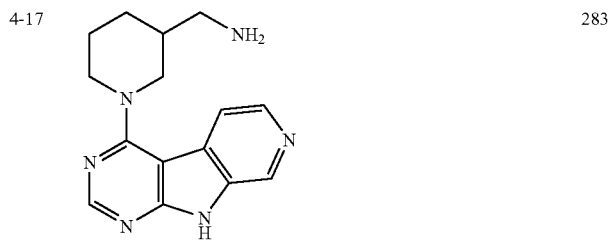 | 283 |

-continued

| Synthesis | Structure | (M + H)+ |
|---|---|---|
| 4-18 | 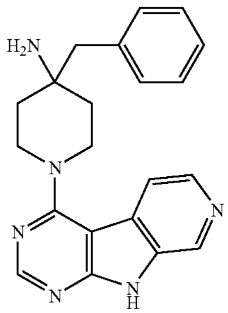 [SMILES: NC1(Cc2ccccc2)CCN(c2ncnc3[nH]c4cnccc4c23)CC1] | 359 |
| 4-19 | 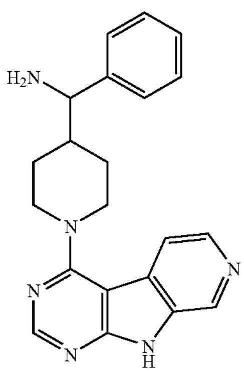 [SMILES: NC(c1ccccc1)C1CCN(c2ncnc3[nH]c4cnccc4c23)CC1] | 359 |
| 4-20 | 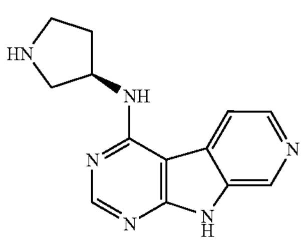 [SMILES: c1cc2c(cn1)[nH]c1ncnc(N[C@@H]3CCNC3)c12] | 255 |
| 4-21 | 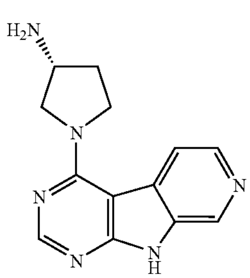 [SMILES: N[C@@H]1CCN(c2ncnc3[nH]c4cnccc4c23)C1] | 255 |

Synthesis 5-1-A

Cyano-(4-nitro-1-oxy-pyridin-3-yl)-acetic acid ethyl ester

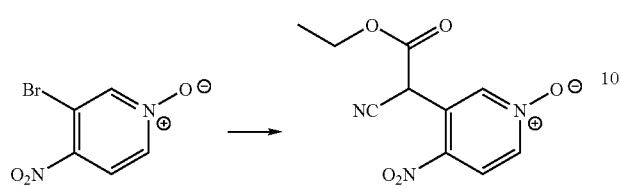

Ethyl cyanoacetate (0.486 mL, 4.57 mmol) was added dropwise at 0° C. to a suspension of 0.11 g (4.57 mmol) of 60% sodium hydride in 10 mL THF. Subsequent addition of 3-bromo-4-nitropyridine N-oxide (1 g, 4.57 mmol) in 5 mL THF resulted in a deep purple colour. The reaction mixture was concentrated and the residue (1.15 g) was used without any further purification. LCMS (1): $R_t$ 0.98 min; m/z 250 [M−H]$^+$

Synthesis 5-1-B

2-Amino-1H-pyrrolo[3,2-c]pyridine-3-carboxylic acid ethyl ester

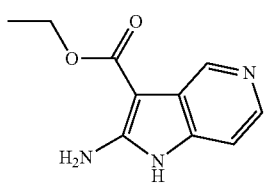

Iron powder (1.28 g, 23 mmol) was carefully added at 100° C. to a solution of cyano-(4-nitro-1-oxy-pyridin-3-yl)-acetic acid ethyl ester in 20 mL of 3:1 acetic acid/water. The reaction mixture was heated and stirred for 1 hour. The reaction mixture was adsorbed onto silica and chromatographed using 10% MeOH/5% 7N NH$_3$ in MeOH/85% DCM as eluent to give 600 mg of the title compound. LCMS (1): $R_t$ 1.15 min; m/z 206 [M+H]$^+$.

Synthesis 5-1-C 9H-1,3,6,9-Tetraaza-fluoren-4-ol

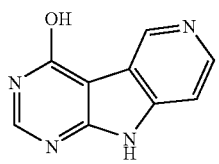 [SMILES: Oc1ncnc2[nH]c3ccncc3c12]

2-Amino-1H-pyrrolo[3,2-c]pyridine-3-carboxylic acid ethyl ester (600 mg, 3 mmol) and ammonium formate (185 mg, 3 mmol) were suspended in 10 mL formamide and heated at 175° C. for 5 hours. Water was added to the cooled reaction mixture and the resulting precipitate collected and dried in vacuo. Unprecipitated product was recovered from the filtrate by using a MP-TsOH SPE cartridge and eluting with 7 N ammonia to give a combined mass of 330 mg of the title compound. LCMS (1): $R_t$ 0.67 min; m/z 188 [M+H]$^+$.

Synthesis 5-1-D

4-Chloro-9H-1,3,6,9-tetraaza-fluorene

A suspension of 9H-1,3,6,9-Tetraaza-fluoren-4-ol (330 mg) and 500 µL of triethylamine were stirred vigorously overnight at 100° C. in 10 mL phosphorous oxychloride. The reaction mixture was then concentrated in vacuo and a small amount of the title compound was isolated by triturating the residue with water. The filtrate was concentrated in vacuo to give 363 mg of title compound which was used without further purification. LCMS (1): $R_t$ 1.11 min; m/z 205 [M+H]$^+$.

Synthesis 5-1-E

C-[4-(9H-1,3,6,9-Tetraaza-fluoren-4-yl)-morpholin-2-yl]-methylamine

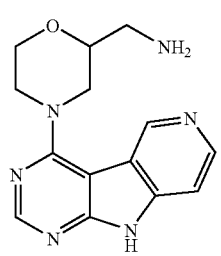

A mixture of 4-chloro-9H-1,3,6,9-tetraaza-fluorene (363 mg) and tert-butyl morpholin-2-yl-methyl carbamate (384 mg) in 4 mL NMP was heated at 140° C. for 20 minutes using microwave irradiation. Concentration and purification by preparative HPLC gave the required Boc-protected intermediate (LCMS (2): $R_t$ 1.88 min; m/z 386 [M+H]$^+$) which was then dissolved in 2:1 DCM/methanol and treated with 5 mL TFA. Upon completion of the deprotection reaction, the product was extracted by purification on a MP-TsOH cartridge, eluting with 3.5 N ammonia in methanol. The eluent was concentrated and the brown residue triturated with ether and dried in vacuo to give 5.8 mg of the title compound. $^1$H NMR (400 MHz, dmso) δ 2.60-2.80 (m, 2H), 2.95-3.05 (m, H), 3.30-3.40 (m, H), 3.55-3.65 (m, H), 3.65-3.75 (m, H), 4.00-

4.05 (m, H), 4.15-4.20 (m, H), 4.35-4.40 (m, H), 7.50 (d, H, J=5.6 Hz), 8.50 (d, H, J=5.6 Hz), 8.55 (s, 2H), 8.95 (s, H).

Synthesis 6-1

Methyl 4-(2-(aminomethyl)morpholino)-9H-pyrimido[4,5-b]indole-7-carboxylate

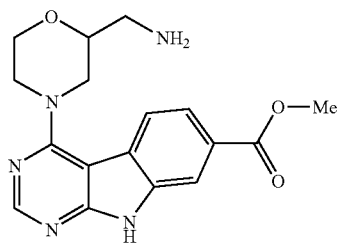 [SMILES: COC(=O)c1ccc2c(c1)[nH]c1ncnc(N3CCOC(CN)C3)c12]

20 mg (0.045 mmol) of 4-[2-(tert-butoxycarbonylaminomethyl)-morpholin-4-yl]-9H-pyrimido[4,5-b]indole-7-carboxylic acid methyl ester (from Synthesis 3-1-F) was dissolved in methanol and deprotected on a MP-TsOH cartridge. The product was eluted with 2 N ammonia in methanol and concentrated in vacuo to give 11.6 mg (0.034 mmol, 75%) of the title compound as a beige solid. LC-MS (1) $R_t$ 1.68 min; m/z (ES+) 342. $^1$H NMR (ppm, MeOD) δ 8.41 (1H, d, J=0.8 Hz), 8.08 (1H, s), 7.88 (1H, dd, J=8.5, 1.5 Hz), 7.80 (1H, d, J=8.3 Hz), 4.21 (1H, d, J=12.6 Hz), 4.13 (1H, d, J=13.1 Hz), 4.06 (1H, dd, J=11.6, 2.5 Hz), 3.93 (3H, s), 3.81 (1H, td, J=11.9, 2.0 Hz), 3.71-3.69 (1H, m), 3.34 (2H, d, J=0.8 Hz), 3.00 (1H, dd, J=12.6, 10.8 Hz), 2.77 (1H, s), 2.76 (1H, d, J=2.5 Hz).

Biological Methods

Measurement of Inhibition of CHK1 Kinase Function

CHK1 kinase function was measured in a DELFIA® assay in order to monitor phosphorylation of a CDC25C peptide using a specific phospho antibody.

The enzyme reaction was carried out in polypropylene plates (Greiner) using a reaction mix (25 μL) containing enzyme and peptide mix (CHK1, 1 nM; Biotin-KKKVSRS-GLYRSPSMPENLNRPR, 1 μM or 15 μL), ATP (30 μM or 5 μL) and either DMSO (2.5%) or test compound (5 μL) diluted to a give a range of concentrations (from 0 to 100 μM in 2.5% DMSO, final concentrations) in assay buffer (40 mM Tris, 40 mM NaCl, 2 mM $MgCl_2$, 1 mM DTT and 0.1% Tween 20). The reaction mixture was incubated for 30 minutes at room temperature and then stopped by the addition of buffer (125 μL) containing 40 mM EDTA, 0.05% Tween 20, 0.1% BSA in TBS (10× concentrate, Sigma). An aliquot (100 μL) of the stopped reaction mixture was transferred to a black neutravidin-coated plate (Perbio) and incubated for 1 hour on a shaker (Titertek, Flow Laboratories) at room temperature. The plates were washed four times with wash buffer (25 mM Tris (pH 8), 150 mM NaCl, and 0.1% Tween 20) (WellWash4, Thermo Life Sciences) and incubated for 1 hour as before with an antibody mixture (100 μL) consisting of anti-phospho CDC25C (1.25 nM, #9528, Cell Signalling Technology) and europium-labelled anti-rabbit IgG (0.3 μg/mL, AD0105, PerkinElmer Life Sciences) diluted in DELFIA assay buffer (PerkinElmer Life Sciences). The plates were washed a further four times with wash buffer before the addition of enhancement solution (100 μL/well, PerkinElmer Life Sciences). The plate was read on a Victor$^2$ 1420 multilabel counter (Perkin Elmer Life Sciences) using a time-resolved measurement mode reading fluorescence at 615 nm.

Measurement of Cytotoxicity

HT29 colon carcinoma cells were obtained from ATCC (Rockville, Md., USA). Cells were grown in DMEM supplemented with 10% foetal calf serum and containing L-glutamine 5 mM, glucose, penicillin, and streptomycin. Cells were grown at 37° C. in a dry 5% $CO_2$ atmosphere. Cytotoxicity assays were carried out in 96-well plates using quadruplicate wells for each dose. Cells were seeded at 1.6× $10^3$ per well in 160 μL medium and were allowed to attach for 36 hours prior to treatment. Test compounds were dissolved in DMSO at 10 mM and serially diluted in culture medium to 5× final concentration prior to addition in a volume of 40 μl per well. Cells were left for 4 doublings (96 hours) in the presence of the test compounds and then fixed in 10% TCA for 30 minutes, washed in water, and dried. The fixed cells were stained with Sulfurhodamine B (SRB, 0.4% in 1% acetic acid, Sigma, Dorset, UK) for 30 minutes, washed in 1% acetic acid, and dried. SRB was resolubilised in 10 mM Tris base and the OD was measured at 490 nm. Results were expressed relative to untreated controls and the concentration of compound required to inhibit growth by 50% (SRB $IC_{50}$) was calculated.

Mitosis Inhibition Assay (MIA)

Checkpoint abrogation by CHK1 kinase function inhibitors in combination with genotoxic agents was assessed using a europium based ELISA assay designed to quantify the number of cells trapped in mitosis after treatment with a genotoxic agent (to induce G2 arrest) followed by a test compound in combination with nocodazole to abrogate this arrest.

HT29 cells were seeded at $10^4$ cells per well into 96 well plates in a volume of 160 μL and left to attach for 36 hours. Etoposide (10 mM stock in DMSO) was diluted in medium to 250 μM and then 40 μL was added to appropriate wells to give a final concentration of 50 μM and incubated for 1 hour. This treatment had previously been optimised to induce a G2 arrest in 80% of cells 16 hours following treatment. After genotoxic drug exposure, the medium was removed and replaced with fresh medium (160 μL). Cells were either untreated (untreated control or etoposide pre-treatment alone), exposed to nocodazole following etoposide pre-treatment or nocodazole alone (100 ng/mL final concentration), or exposed to increasing concentrations of test compound (200 μM-0.01 nM final concentration) in combination with nocodazole (100 ng/mL final concentration). Test compounds were added in 40 μL using quadruplicate wells for each dose. After 21 hours exposure, the medium was removed and cells were fixed in 4% formaldehyde in phosphate buffered saline (PBS, pH 7.4, pre-cooled to 4° C.) for 30 minutes at 4° C., followed by 100% methanol (pre-cooled to −20° C.) for 10 minutes at ambient temperature. Wells were washed with PBS and blocked with 5% dried milk (Marvel) in Tris-buffered saline (TBS, pH 7.4) at 37° C. for 30 minutes. Each well was washed three times with water containing 0.1% tween 20. Primary antibody (MPM-2, Upstate cat#05-368, 1 μg/mL in 5% milk in TBS) was added to each well and incubated overnight with shaking at 4° C. Primary antibody was removed and wells were washed with water containing 0.1% Tween 20. The secondary antibody (europium labelled anti-mouse, Perkin-Elmer cat# AD0124, 333 ng/mL in assay buffer Perkin-Elmer cat#1244-111) was added to each well and incubated at 37° C. for 1 hour. Each well was washed with water 0.1% containing tween 20 and treated with enhancement solution (Perkin-Elmer cat#1244-105). Europium emissions were counted on a Wallac, Victor$^2$ counter (Perkin-Elmer, Bucks UK). Appropriate controls were included and results were expressed as the concentration of test compound required to allow 50% of cells to enter mitosis (MIA IC$_{50}$).

Biological Data

Biological data were obtained using the CHK1 kinase function inhibition assay described above for the following 33 compounds: 1-1 through 1-3, 2-1 through 2-6, 3-1, 4-1 through 4-21, 5-1, and 6-1.

For the CHK1 kinase function inhibition assay, the IC$_{50}$ (μM) values are as follows:

at least 5 of the compounds have an IC50 of 1 μM or less.
at least 23 of the compounds have an IC50 of 10 μM or less.
all 33 of the compounds have an IC50 of 100 μM or less.

One compound, compound 1-1, has an IC50 value of 3.15 μM.

One compound, compound 2-2, has an IC50 value of 3.7 μM.

One compound, compound 4-3, has an IC50 value of 1.7 μM.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Balaint and Vousden, 2001, "Activation and activities of the p53 tumour suppressor protein," *Br. J. Cancer*, Vol. 85, pp. 1813-1823.

Bartek and Lukas, 2003, "Chk1 and Chk2 kinases in checkpoint control and cancer," *Cancer Cell*, Vol. 3, pp. 421-429.

Carson and Lois, 1995, "Cancer progression and p53," *Lancet*, Vol. 346, pp. 1009-1011.

Dixon and Norbury, 2002, "Therapeutic exploitation of checkpoint defects in cancer cells lacking p53 function," *Cell Cycle*, Vol. 1, pp. 362-368.

Greenblatt et al., 1994, "Mutations in the p53 tumor suppressor gene: clues to cancer etiology and molecular pathogenesis," *Cancer Res.*, Vol. 54, pp. 4855-4878.

Hoehn et al., 1973, "Sulfur Derivatives of Pyrazolo[3,4-b] Pyridines, U.S. Pat. No. 3,773,778, published 20 Nov. 1973.

Liu et al., 2000, "Chk1 is an essential kinase that is regulated by Atr and required for the G(2)/M DNA damage checkpoint," *Genes Dev.*, Vol. 14, pp. 1448-1459.

Sanchez et al., 1997, "Conservation of the Chk1 checkpoint pathway in mammals: linkage of DNA damage to Cdk regulation through Cdc25," *Science*, Vol. 277, pp. 1497-1501.

Sorensen et al., 2005, "Cell-cycle checkpoint kinase Chk1 is required for mammalian homologous recombination repair," *Nat. Cell Biol.*, Vol 7, pp. 195-201.

Tao and Lin, 2006, "Chk1 inhibitors for novel cancer treatment," *Anti-Cancer Agents in Medicinal Chemistry*, Vol. 6, pp. 377-388.

Ugarkar et al., 2000, "Adenosine Kinase Inhibitors. 1. Synthesis, Enzyme Inhibition, and Antiseizure Activity of 5-Iodotubercidin Analogues," *Journal of Medicinal Chemistry*, Vol. 43, pp. 2883-2893.

Wang et al., 1996, "UCN-01: a potent abrogator of G2 checkpoint function in cancer cells with disrupted p53," *J. Natl. Cancer Inst.*, Vol. 8, pp. 956-965.

Weinert and Hartwell, 1989, "Control of G2 delay by the rad9 gene of *Saccharomyces cerevisiae*," *J. Cell Sci. Suppl.*, Vol. 12, pp. 145-148.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer. Ther.*, Vol. 5, pp. 1935-1943.

Zachos et al., 2003, "Chk1-deficient tumour cells are viable but exhibit multiple checkpoint and survival defects," *EMBO J.*, Vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, Vol. 99, pp. 14795-14800.

The invention claimed is:

1. A compound of the following formula, or a pharmaceutically acceptable salt thereof:

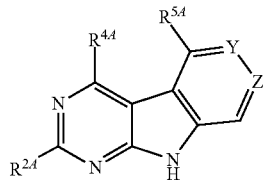

wherein:
either: Y is $CR^{6A}$ and Z is N;
or: Y is N and Z is $CR^{7A}$;
—$R^{4A}$ is independently -$Q^1$, -$Q^2$, -$Q^3$, or -$Q^4$;
—$R^{2A}$ is independently —H or -$G^1$;
—$R^{5A}$ is independently —H or -$G^2$;
—$R^{6A}$ is independently —H or -$G^3$; and
—$R^{7A}$ is independently —H or -$G^3$;
and wherein:
-$Q^1$ is independently —$NH_2$, —$NHR^{W1}$, or —$NR^{W1}_2$;
wherein:
each —$R^{W1}$ is independently:
—$R^{X1}$, —$R^{X2}$, —$R^{X3}$, —$R^{X4}$, —$R^{X5}$, —$R^{X6}$, —$R^{X7}$, —$R^{X8}$,
-$L^X$-$R^{X4}$, -$L^X$-$R^{X5}$, -$L^X$-$R^{X6}$, -$L^X$-$R^{X7}$, or -$L^X$-$R^{X8}$;
wherein:
each —$R^{X1}$ is saturated aliphatic $C_{1-6}$alkyl;
each —$R^{X2}$ is aliphatic $C_{2-6}$alkenyl;
each —$R^{X3}$ is aliphatic $C_{2-6}$alkynyl;
each —$R^{X4}$ is saturated $C_{3-6}$cycloalkyl;
each —$R^{X5}$ is $C_{3-6}$cycloalkenyl;
each —$R^{X6}$ is non-aromatic $C_{3-7}$heterocyclyl;
each —$R^{X7}$ is $C_{6-10}$carboaryl;
each —$R^{X8}$ is $C_{5-10}$heteroaryl;
each -$L^X$- is saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{5-10}$heteroaryl, and $C_{1-3}$alkylene is optionally substituted with one or more substituents —$R^{X9}$, wherein each —$R^{X9}$ is independently:
—F, —Cl, —Br, —I,
—$R^{Y1}$,
—$CF_3$,
—OH,
—$OR^{Y1}$,
—$OCF_3$,
—SH,
—$SR^{Y1}$,
—CN,
—$NO_2$,
—$NH_2$, —$NHR^{Y1}$, —$NR^{Y1}{}_2$, —$NR^{Y2}R^{Y3}$,
—C(=O)OH,
—C(=O)$OR^{Y1}$,
—C(=O)$NH_2$, —C(=O)$NHR^{Y1}$, —C(=O)$NR^{Y1}{}_2$,
—C(=O)$NR^{Y2}R^{Y3}$,
-$L^Y$-OH, -$L^Y$-$OR^{Y1}$,
-$L^Y$-$NH_2$, -$L^Y$-$NHR^{Y1}$, -$L^Y$-$NR^{Y1}{}_2$, or -$L^Y$-$NR^{Y2}R^{Y3}$;
wherein:
each —$R^{Y1}$ is independently saturated aliphatic $C_{1-4}$alkyl, phenyl, or benzyl;
each -$L^Y$- is saturated aliphatic $C_{1-5}$alkylene; and
in each group —$NR^{Y2}R^{Y3}$, $R^{Y2}$ and $R^{Y3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

-$Q^2$ is —$NR^{W2}R^{W3}$, wherein $R^{W2}$ and $R^{W3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

-$Q^3$ is:

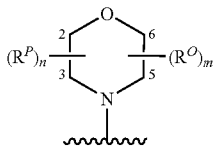

wherein:
m is independently 0 or 1;
n is independently 0, 1 or 2;
each —$R^P$ is independently saturated aliphatic $C_{1-3}$alkyl or —$CF_3$;
—$R^Q$ is independently:
-$L^R$-$NH_2$, -$L^R$-$NHR^R$, -$L^R$-$NR^R{}_2$,
-$L^R$-OH, -$L^R$-$OR^R$,
—C(=O)OH, —C(=O)$OR^R$,
—C(=O)$NH_2$, —C(=O)$NHR^R$, —C(=O)$NR^R{}_2$,
-$L^R$-C(=O)OH, -$L^R$-C(=O)$OR^R$,
-$L^R$-C(=O)$NH_2$, -$L^R$-C(=O)$NHR^R$, -$L^R$-C(=O)$NR^R{}_2$, or
-$L^R$-CN;
wherein:
each -$L^R$- is saturated aliphatic $C_{1-3}$alkylene; and
each —$R^R$ is saturated aliphatic $C_{1-3}$alkyl;

-$Q^4$ is independently:
—NH-$L^T$-$NH_2$, —NH-$L^T$-$NHR^{T1}$, —NH-$L^T$-$NR^{T1}{}_2$, —NH-$L^T$-$NR^{T2}R^{T3}$, —$NR^{T1}$-$L^T$-$NH_2$, —$NR^{T1}$-$L^T$-$NHR^{T1}$, —$NR^{T1}$-$L^T$-$NR^{T1}{}_2$, —NR-$L^T$-$NR^{T2}R^{T3}$;
—NH-$L^T$-NHC(=O)$R^{T1}$, —NH-$L^T$-N($R^{T1}$)C(=O)$R^{T1}$,
—N($R^{T1}$)-$L^T$-NHC(=O)$R^{T1}$, or —N($R^{T1}$)-$L^T$-N($R^{T1}$)C(=O)$R^{T1}$,
wherein:
each -$L^T$- is saturated aliphatic $C_{1-6}$alkylene;
each —$R^{T1}$ is independently:
—$R^{U1}$, —$R^{U2}$, —$R^{U3}$, —$R^{U4}$, —$R^{U5}$, —$R^{U6}$, —$R^{U7}$, —$R^{U8}$,
wherein:
each —$R^{U1}$ is saturated aliphatic $C_{1-6}$alkyl;
each —$R^{U2}$ is aliphatic $C_{2-6}$alkenyl;
each —$R^{U3}$ is aliphatic $C_{2-6}$alkynyl;
each —$R^{U4}$ is saturated $C_{3-6}$cycloalkyl;
each —$R^{U5}$ is $C_{3-6}$cycloalkenyl;
each —$R^{U6}$ is non-aromatic $C_{3-7}$heterocyclyl;
each —$R^{U7}$ is $C_{6-10}$-carboaryl;
each —$R^{U8}$ is $C_{5-10}$heteroaryl;
each -$L^U$- is saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$-carboaryl, $C_{5-10}$heteroaryl, and $C_{1-3}$alkylene is optionally substituted with one or more substituents —$R^{U9}$, wherein each —$R^{U9}$ is independently:
—F, —Cl, —Br, —I,
—$R^{v1}$,
—$CF_3$,
—OH,
—$OR^{v1}$,
—$OCF_3$,
—SH,
—$SR^{v1}$,
—CN,
—$NO_2$,
—$NH_2$, —$NHR^{v1}$, —$NR^{v1}{}_2$, —$NR^{V2}R^{V3}$,
—C(=O)OH,
—C(=O)$OR^{v1}$,
—C(=O)$NH_2$, —C(=O)$NHR^{v1}$, —C(=O)$NR^{v1}{}_2$,
—C(=O)$NR^{V2}R^{V3}$,
-$L^V$-OH, -$L^V$-$OR^{v1}$,
-$L^V$-$NH_2$, -$L^V$-$NHR^{v1}$, -$L^V$-$NR^{v1}{}_2$, or -$L^V$-$NR^{V2}R^{V3}$;
wherein:
each —$R^{v1}$ is independently saturated aliphatic $C_{1-4}$alkyl, phenyl, or benzyl;
each -$L^V$- is saturated aliphatic $C_{1-5}$alkylene; and
in each group —$NR^{V2}R^{V3}$, $R^{V2}$ and $R^{V3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O; and
in each group —$NR^{T2}R^{T3}$, $R^{T2}$ and $R^{T3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

and wherein:

-$G^1$ is independently:
- —F, —Cl, —Br, —I,
- —$R^{A1}$,
- —$CF_3$,
- —OH,
- -$L^A$-OH,
- —$OR^{A1}$,
- -$L^A$-$OR^{A1}$,
- —$OCF_3$,
- —SH,
- —$SR^{A1}$,
- —CN,
- —$NO_2$,
- —$NH_2$, —$NHR^{A1}$, —$NR^{A1}{}_2$, —$NR^{A2}R^{A3}$,
- -$L^A$-$NH_2$, -$L^A$-$NHR^{A1}$, -$L^A$-$NR^{A1}{}_2$, -$L^A$-$NR^{A2}R^{A3}$,
- —C(=O)OH,
- —C(=O)$OR^{A1}$,
- —C(=O)$NH_2$, —C(=O)$NHR^{A1}$, —C(=O)$NR^{A1}{}_2$, —C(=O)$NR^{A2}R^{A3}$,
- —NHC(=O)$R^{A1}$, —$NR^{A1}$C(=O)$R^{A1}$,
- —NHC(=O)$OR^{A1}$, —$NR^{A1}$C(=O)$OR^{A1}$,
- —OC(=O)$NH_2$, —OC(=O)$NHR^{A1}$, —OC(=O)$NR^{A1}{}_2$,
- —OC(=O)$R^{A1}$,
- —C(=O)$R^{A1}$,
- —NHC(=O)$NH_2$, —NHC(=O)$NHR^{A1}$,
- —NHC(=O)$NR^{A1}{}_2$, —NHC(=O)$NR^{A2}R^{A3}$,
- —$NR^{A1}$C(=O)$NH_2$, —$NR^{A1}$C(=O)$NHR^{A1}$,
- —$NR^{A1}$C(=O)$NR^{A1}{}_2$, —$NR^{A1}$C(=O)$NR^{A2}R^{A3}$,
- —NHS(=O)$_2R^{A1}$, —$NR^{A1}$S(=O)$_2R^{A1}$,
- —S(=O)$_2NH_2$, —S(=O)$_2NHR^{A1}$, —S(=O)$_2NR^{A1}{}_2$, —S(=O)$_2NR^{A2}R^{A3}$,
- —S(=O)$R^{A1}$,
- —S(=O)$_2R^{A1}$,
- —OS(=O)$_2R^{A1}$, or
- —S(=O)$_2OR^{A1}$, wherein:
each -$L^A$- is saturated aliphatic $C_{1-5}$alkylene;
in each group —$NR^{A2}R^{A3}$, $R^{A2}$ and $R^{A3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{A1}$ is independently:
- —$R^{B1}$, —$R^{B2}$, —$R^{B3}$, —$R^{B4}$, —$R^{B5}$, —$R^{B6}$, —$R^{B7}$, —$R^{B8}$,
- -$L^B$-$R^{B4}$, -$L^B$-$R^{B5}$, -$L^B$-$R^{B6}$, -$L^B$-$R^{B7}$, or -$L^B$-$R^{B8}$;

wherein:
- each —$R^{B1}$ is saturated aliphatic $C_{1-6}$alkyl;
- each —$R^{B2}$ is aliphatic $C_{2-6}$alkenyl;
- each —$R^{B3}$ is aliphatic $C_{2-6}$alkynyl;
- each —$R^{B4}$ is saturated $C_{3-6}$cycloalkyl;
- each —$R^{B5}$ is $C_{3-6}$cycloalkenyl;
- each —$R^{B6}$ is non-aromatic $C_{3-7}$heterocyclyl;
- each —$R^{B7}$ is $C_{6-10}$carboaryl;
- each —$R^{B8}$ is $C_{5-10}$heteroaryl;
- each -$L^B$- is saturated aliphatic $C_{1-3}$alkylene;

and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{5-10}$heteroaryl, and $C_{1-3}$alkylene is optionally substituted with one or more substituents —$R^{B9}$, wherein each —$R^{B9}$ is independently:
- —F, —Cl, —Br, —I,
- —$R^{C1}$,
- —$CF_3$,
- —OH,
- —$OR^{C1}$,
- —$OCF_3$,
- —SH,
- —$SR^{C1}$,
- —CN,
- —$NO_2$,
- —$NH_2$, —$NHR^{C1}$, —$NR^{C1}{}_2$, —$NR^{C2}R^{C3}$,
- —C(=O)OH,
- —C(=O)$OR^{C1}$,
- —C(=O)$NH_2$, —C(=O)$NHR^{C1}$, —C(=O)$NR^{C1}{}_2$, —C(=O)$NR^{C2}R^{C3}$,
- -$L^C$-OH, -$L^C$-$OR^{C1}$,
- -$L^C$-$NH_2$, -$L^C$-$NHR^{C1}$, -$L^C$-$NR^{C1}{}_2$, or -$L^C$-$NR^{C2}R^{C3}$;

wherein:
each —$R^{C1}$ is independently saturated aliphatic $C_{1-4}$alkyl, phenyl, or benzyl;
each -$L^C$- is saturated aliphatic $C_{1-5}$alkylene; and
in each group —$NR^{C2}R^{C3}$, $R^{C2}$ and $R^{C3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

-$G^2$ is independently:
- —F, —Cl, —Br, —I,
- —$R^{E1}$,
- —$CF_3$,
- —OH,
- -$L^E$-OH,
- —$OR^{E1}$,
- -$L^E$-$OR^{E1}$,
- —$OCF_3$,
- —SH,
- —$SR^{E1}$,
- —CN,
- —$NO_2$,
- —$NH_2$, —$NHR^{E1}$, —$NR^{E1}{}_2$, —$NR^{E2}R^{E3}$,
- -$L^E$-$NH_2$, -$L^E$-$NHR^{E1}$, -$L^E$-$NR^{E1}{}_2$, -$L^E$-$NR^{E2}R^{E3}$,
- —C(=O)OH,
- —C(=O)$OR^{E1}$,
- —C(=O)$NH_2$, —C(=O)$NHR^{E1}$, —C(=O)$NR^{E1}{}_2$, —C(=O)$NR^{E2}R^{E3}$,
- —NHC(=O)$R^{E1}$, —$NR^{E1}$C(=O)$R^{E1}$,
- —NHC(=O)$OR^{E1}$, —$NR^{E1}$C(=O)$OR^{E1}$,
- —OC(=O)$NH_2$, —OC(=O)$NHR^{E1}$, —OC(=O)$NR^{E1}{}_2$,
- —OC(=O)$R^{E1}$,
- —C(=O)$R^{E1}$,
- —NHC(=O)$NH_2$, —NHC(=O)$NHR^{E1}$,
- —NHC(=O)$NR^{E1}{}_2$, —NHC(=O)$NR^{E2}R^{E3}$,
- —$NR^{E1}$C(=O)$NH_2$, —$NR^{E1}$C(=O)$NHR^{E1}$,
- —$NR^{E1}$C(=O)$NR^{E1}{}_2$, —$NR^{E1}$C(=O)$NR^{E2}R^{E3}$,
- —NHS(=O)$_2R^{E1}$, —$NR^{E1}$S(=O)$_2R^{E1}$,
- —S(=O)$_2NH_2$, —S(=O)$_2NHR^{E1}$, —S(=O)$_2NR^{E1}{}_2$, —S(=O)$_2NR^{E2}R^{E3}$,
- —S(=O)$R^{E1}$,
- —S(=O)$_2R^{E1}$,
- —OS(=O)$_2R^{E1}$, or
- —S(=O)$_2OR^{E1}$, wherein:
  each -$L^E$- is saturated aliphatic $C_{1-5}$alkylene;
in each group —$NR^{E2}R^{E3}$, $R^{E2}$ and $R^{E3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{E1}$ is independently:
  —$R^{F1}$, —$R^{F2}$, —$R^{F3}$, —$R^{F4}$, —$R^{F5}$, —$R^{F6}$, —$R^{F7}$, —$R^{F8}$,
  -$L^F$-$R^{F4}$, -$L^F$-$R^{F5}$, -$L^F$-$R^{F6}$, -$L^F$-$R^{F7}$ or -$L^F R^{F8}$;
wherein:
  each —$R^{F1}$ is saturated aliphatic $C_{1-6}$alkyl;
  each —$R^{F2}$ is aliphatic $C_{2-6}$alkenyl;
  each —$R^{F3}$ is aliphatic $C_{2-6}$alkynyl;
  each —$R^{F4}$ is saturated $C_{3-6}$cycloalkyl;
  each —$R^{F5}$ is $C_{3-6}$cycloalkenyl;
  each —$R^{F6}$ is non-aromatic $C_{3-7}$heterocyclyl;
  each —$R^{F7}$ is $C_{6-10}$carboaryl;
  each —$R^{F8}$ is $C_{5-10}$heteroaryl;
  each -$L^F$- is saturated aliphatic $C_{1-3}$alkylene;
and wherein:
  each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{5-10}$heteroaryl, and $C_{1-3}$alkylene is optionally substituted with one or more substituents —$R^{F9}$, wherein each —$R^{F9}$ is independently:
    —F, —Cl, —Br, —I,
    —$R^{G1}$,
    —$CF_3$,
    —OH,
    —$OR^{G1}$,
    —$OCF_3$,
    —SH,
    —$SR^{G1}$,
    —CN,
    —$NO_2$,
    —$NH_2$, —$NHR^{G1}$, —$NR^{G1}{}_2$, —$NR^{G2}R^{G3}$,
    —C(=O)OH,
    —C(=O)$OR^{G1}$,
    —C(=O)$NH_2$, —C(=O)$NHR^{G1}$, —C(=O)$NR^{G1}{}_2$,
    —C(=O)$NR^{G2}R^{G3}$,
    -$L^G$-OH, -$L^G$-$OR^{G1}$,
    -$L^G$-$NH_2$, -$L^G$-$NHR^{G1}$, -$L^G$-$NR^{G1}{}_2$, or -$L^G$-$NR^{G2}R^{G3}$;
  wherein:
    each —$R^{G1}$ is independently saturated aliphatic $C_{1-4}$alkyl, phenyl, or benzyl;
    each -$L^G$- is saturated aliphatic $C_{1-5}$alkylene; and
  in each group —$NR^{G2}R^{G3}$, $R^{G2}$ and $R^{G3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
-$G^3$ is independently:
  —F, —Cl, —Br, —I,
  —$R^{H1}$,
  —$CF_3$,
  —OH,
  -$L^H$-OH,
  —$OR^{H1}$,
  -$L^H$-$OR^{H1}$,
  —$OCF_3$,
  —SH,
  —$SR^{H1}$,
  —CN,
  —$NO_2$,
  —$NH_2$, —$NHR^{H1}$, —$NR^{H1}{}_2$, —$NR^{H2}R^{H3}$,
  -$L^H$-$NH_2$, -$L^H$-$NHR^{H1}$, -$L^H$-$NR^{H1}{}_2$, -$L^H$-$NR^{H2}R^{H3}$,
  —C(=O)OH,
  —C(=O)$OR^{H1}$,
  —C(=O)$NH_2$, —C(=O)$NHR^{H1}$, —C(=O)$NR^{H1}{}_2$,
  —C(=O)$NR^{H2}R^{H3}$,
  —NHC(=O)$R^{H1}$, —$NR^{H1}$C(=O)$R^{H1}$,
  —NHC(=O)$OR^{H1}$, —$NR^{H1}$C(=O)$OR^{H1}$,
  —OC(=O)$NH_2$, —OC(=O)$NHR^{H1}$, —OC(=O)$NR^{H1}{}_2$,
  —OC(=O)$R^{H1}$,
  —C(=O)$R^{H1}$,
  —NHC(=O)$NH_2$, —NHC(=O)$NHR^{H1}$,
  —NHC(=O)$NR^{H1}{}_2$, —NHC(=O)$NR^{H2}R^{H3}$,
  —$NR^{H1}$C(=O)$NH_2$, —$NR^{H1}$C(=O)$NHR^{H1}$,
  —$NR^{H1}$C(=O)$NR^{H1}{}_2$, —$NR^{H1}$C(=O)$NR^{H2}R^{H3}$,
  —NHS(=O)$_2R^{H1}$, —$NR^{H1}$S(=O)$_2R^{H1}$,
  —S(=O)$_2NH_2$, —S(=O)$_2NHR^{H1}$, —S(=O)$_2NR^{H1}{}_2$,
  —S(=O)$_2NR^{H2}R^{H3}$,
  —S(=O)$R^{H1}$,
  —S(=O)$_2R^{H1}$,
  —OS(=O)$_2R^{H1}$, or
  —S(=O)$_2OR^{H1}$,
wherein:
  each -$L^H$- is saturated aliphatic $C_{1-5}$alkylene;
  in each group —$NR^{H2}R^{H3}$, $R^{H2}$ and $R^{H3}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O; and
  each —$R^{H1}$ is independently:
    —$R^{J1}$, —$R^{J2}$, —$R^{J3}$, —$R^{J4}$, —$R^{J5}$, —$R^{J6}$, —$R^{J7}$, —$R^{J8}$,
    -$L^J$-$R^{J4}$, -$L^J$-$R^{J5}$, -$L^J$-$R^{J6}$, -$L^J$-$R^{J7}$, or -$L^J$-$R^{J8}$;
  wherein:
    each —$R^{J1}$ is saturated aliphatic $C_{1-6}$alkyl;
    each —$R^{J2}$ is aliphatic $C_{2-6}$alkenyl;
    each —$R^{J3}$ is aliphatic $C_{2-6}$alkynyl;
    each —$R^{J4}$ is saturated $C_{3-6}$cycloalkyl;
    each —$R^{J5}$ is $C_{3-6}$cycloalkenyl;
    each —$R^{J6}$ is non-aromatic $C_{3-7}$heterocyclyl;
    each —$R^{J7}$ is $C_{6-10}$carboaryl;
    each —$R^{J8}$ is $C_{5-10}$heteroaryl;
    each -$L^J$- is saturated aliphatic $C_{1-3}$alkylene;
  and wherein:
    each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-7}$heterocyclyl, $C_{6-10}$carboaryl, $C_{5-10}$heteroaryl, and $C_{1-3}$alkylene is optionally substituted with one or more substituents —$R^{J9}$, wherein each —$R^{J9}$ is independently:
      —F, —Cl, —Br, —I,
      —$R^{K1}$,
      —$CF_3$,
      —OH,
      —$OR^{K1}$,
      —$OCF_3$,
      —SH,
      —$SR^{K1}$,
      —CN, —NO₂,
—NH₂, —NHR^{K1}, —NR^{K1}₂, NR^{K2}R^{K3},
—C(=O)OH,
—C(=O)OR^{K1},
—C(=O)NH₂, —C(=O)NHR^{K1}, —C(=O)NR^{K1}₂, —C(=O)NR^{K2}R^{K3},
-L^{K}-OH, -L^{K}-OR^{K1},
-L^{K}-NH₂, -L^{K}-NHR^{K1}, -L^{K}-NR^{K1}₂, or -L^{K}-NR^{K2}R^{K3};

wherein:
each —R^{K1} is independently saturated aliphatic $C_{1-4}$alkyl, phenyl, or benzyl;
each -L^{K}- is saturated aliphatic $C_{1-5}$alkylene; and
in each group —NR^{K2}R^{K3}, R^{K2} and R^{K3}, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

2. A compound according to claim 1, wherein:
Y is $CR^{6A}$ and Z is N;
$R^{6A}$ is —H;
—$R^{2A}$ is —H; and
—$R^{5A}$ is —H.

3. A compound according to claim 1, wherein:
Y is N and Z is $CR^{7A}$;
—$R^{7A}$ is —H;
—$R^{2A}$ is —H; and
—$R^{5A}$ is —H.

4. A compound according to claim 1, wherein —$R^{4A}$ is -Q¹.
5. A compound according to claim 2, wherein —$R^{4A}$ is -Q¹.
6. A compound according to claim 3, wherein —$R^{4A}$ is -Q¹.
7. A compound according to claim 1, wherein —$R^{4A}$ is -Q².
8. A compound according to claim 2, wherein —$R^{4A}$ is -Q².
9. A compound according to claim 3, wherein —$R^{4A}$ is -Q².
10. A compound according to claim 1, wherein —$R^{4A}$ is -Q³.
11. A compound according to claim 2, wherein —$R^{4A}$ is -Q³.
12. A compound according to claim 3, wherein —$R^{4A}$ is -Q³.
13. A compound according to claim 1, wherein —$R^{4A}$ is -Q⁴.
14. A compound according to claim 2, wherein —$R^{4A}$ is -Q⁴.
15. A compound according to claim 3, wherein —$R^{4A}$ is -Q⁴.

16. A compound selected from the following compounds, or a pharmaceutically acceptable salt thereof:

(4-1)
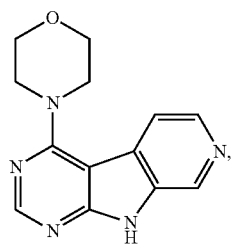

(4-2)
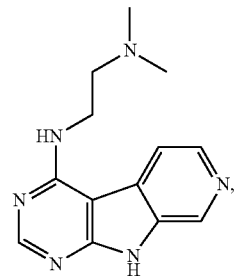

(4-3)
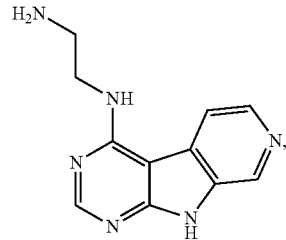

(4-4)
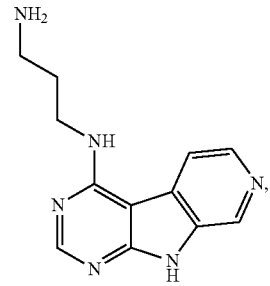

(4-5)
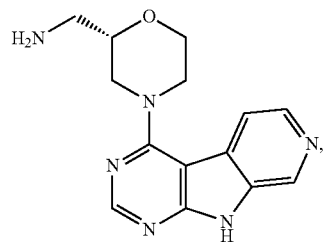

(4-6)
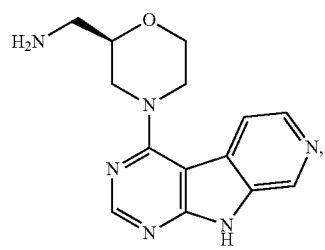

(4-7)
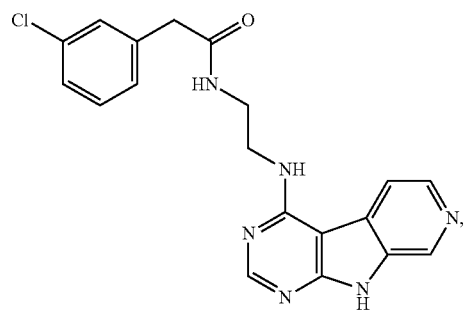

(4-8)
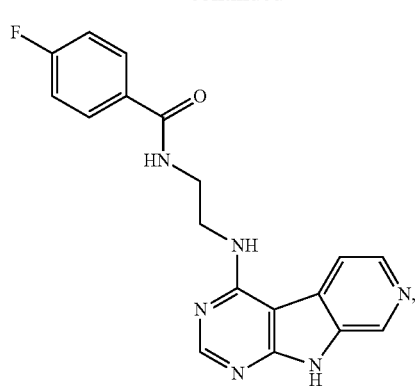
(4-9)
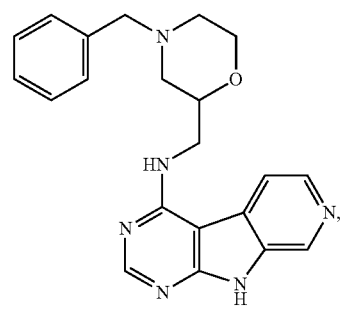
(4-10)
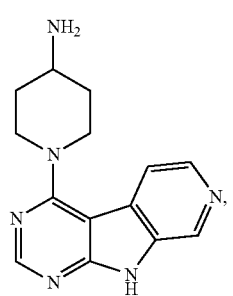
(4-11)
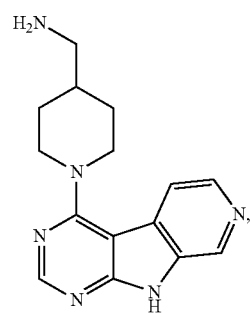
(4-12)
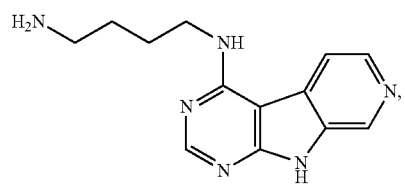
(4-13)
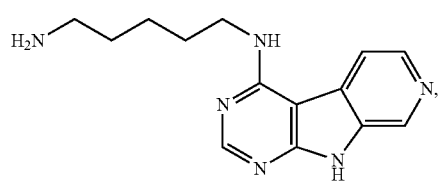
(4-14)
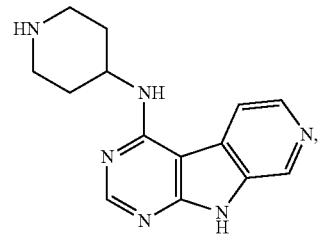
(4-15)
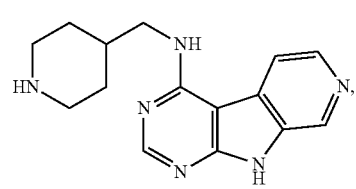
(4-16)
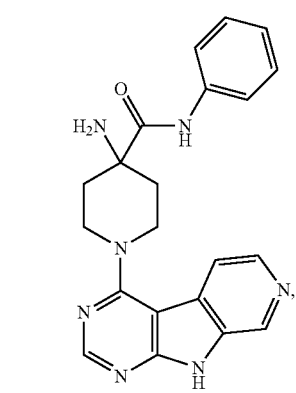
(4-17)
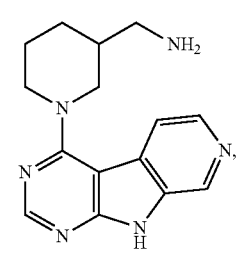
(4-18)
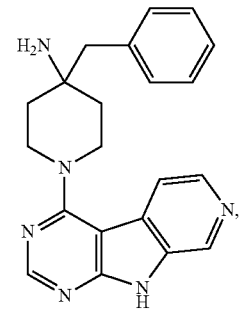

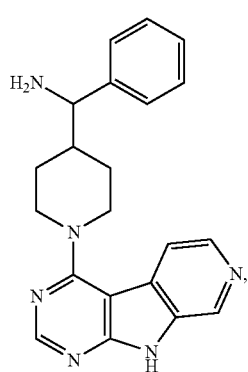
(4-19)
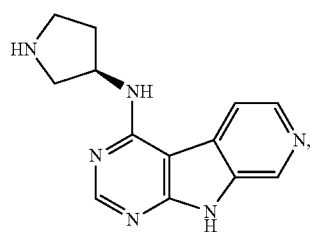
(4-20)
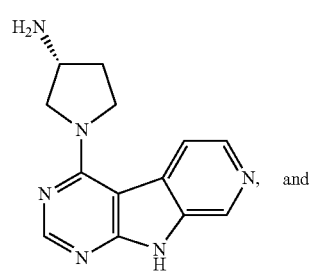
(4-21)
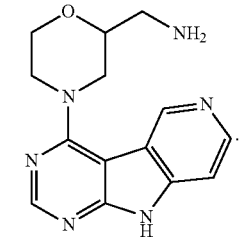
(5-1)
17. A pharmaceutical composition comprising a compound according to claim 1, and a pharmaceutically acceptable carrier or diluent.
18. A method of preparing a pharmaceutical composition comprising the step of admixing a compound according to claim 1, and a pharmaceutically acceptable carrier or diluent.
* * * * *

UNITED STATES PATENT AND TRADEMARK OFFICE
CERTIFICATE OF CORRECTION

PATENT NO.        : 8,618,121 B2                                           Page 1 of 1
APPLICATION NO. : 12/665961
DATED             : December 31, 2013
INVENTOR(S)       : Collins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 730 days.

Signed and Sealed this
Twenty-second Day of September, 2015

Michelle K. Lee
*Director of the United States Patent and Trademark Office*